(12) United States Patent
Dougherty et al.

(10) Patent No.: US 11,504,224 B2
(45) Date of Patent: *Nov. 22, 2022

(54) IMPLANT PLACEMENT SYSTEMS AND ONE-HANDED METHODS FOR TISSUE FIXATION USING SAME

(71) Applicant: Tenjin LLC, Brazoria, TX (US)

(72) Inventors: Christopher P. Dougherty, Rogers, AR (US); Gary R. Heisler, Brazoria, TX (US); Robert A. Van Wyk, St. Pete Beach, FL (US)

(73) Assignee: TENJIN LLC, Brazoria, TX (US)

( * ) Notice: Subject to any disclaimer, the term of this patent is extended or adjusted under 35 U.S.C. 154(b) by 924 days.

This patent is subject to a terminal disclaimer.

(21) Appl. No.: 16/294,663

(22) Filed: Mar. 6, 2019

(65) Prior Publication Data

US 2019/0290420 A1    Sep. 26, 2019

Related U.S. Application Data

(63) Continuation-in-part of application No. PCT/US2017/050222, filed on Sep. 6, 2017, which is
(Continued)

(51) Int. Cl.
*A61F 2/08* (2006.01)
*A61B 17/00* (2006.01)
(Continued)

(52) U.S. Cl.
CPC ...... *A61F 2/0811* (2013.01); *A61B 17/00234* (2013.01); *A61B 17/0401* (2013.01);
(Continued)

(58) Field of Classification Search
CPC ............... A61F 2/0811; A61B 17/0483; A61B 17/0485; A61B 17/0401;
(Continued)

(56) References Cited

U.S. PATENT DOCUMENTS 5,100,417 A   3/1992   Cerier
5,152,765 A   10/1992  Ross
(Continued)

OTHER PUBLICATIONS

Product Brochure for "SpeedBridge™ and SpeedFix™ Knotless Rotator Cuff Repair using the SwiveLock® C and FiberTape®: Surgical Technique", Arthrex. Inc., 2013.
(Continued)

*Primary Examiner* — Todd J Scherbel
(74) *Attorney, Agent, or Firm* — Smith Patent, LLC; Chalin A. Smith

(57) ABSTRACT

Described herein is a simplified placement system and method for a tissue graft anchor by which a surgeon may introduce one or more sutures into a hole in a boney tissue, apply a precise amount of tension to the sutures to advance a soft tissue graft to a desired location, and then advance the anchor into the bone, preferably while maintaining the requisite pre-determined suture tension and without introducing spin to the suture. Particularly preferred embodiments allow for the one-handed operation. To that end, embodiments in which relative axial movement between the inner tensioning device and outer driver device is optionally physically constrained, for example by means of cooperating and/or compressive elements disposed in the respective hub and handle portions, are described herein.

20 Claims, 91 Drawing Sheets

Related U.S. Application Data a continuation-in-part of application No. 15/429,527, filed on Feb. 10, 2017, now Pat. No. 9,907,548, and a continuation-in-part of application No. 15/256,838, filed on Sep. 6, 2016, now Pat. No. 9,782,250, which is a continuation-in-part of application No. 15/012,060, filed on Feb. 1, 2016, now Pat. No. 9,566,060, which is a continuation-in-part of application No. 14/972,662, filed on Dec. 17, 2015, now Pat. No. 9,795,374, which is a continuation of application No. 14/636,389, filed on Mar. 3, 2015, now Pat. No. 9,226,817.

(60) Provisional application No. 61/999,405, filed on Jul. 26, 2014, provisional application No. 61/998,766, filed on Jul. 7, 2014, provisional application No. 61/998,391, filed on Jun. 26, 2014, provisional application No. 61/966,744, filed on Mar. 3, 2014.

(51) Int. Cl.
*A61B 17/04* (2006.01)
*A61B 17/06* (2006.01)
*A61B 90/00* (2016.01)

(52) U.S. Cl.
CPC ...... *A61B 17/0483* (2013.01); *A61B 17/0485* (2013.01); *A61F 2/0805* (2013.01); *A61B 17/0482* (2013.01); *A61B 17/06061* (2013.01); *A61B 2017/0088* (2013.01); *A61B 2017/00305* (2013.01); *A61B 2017/00309* (2013.01); *A61B 2017/00314* (2013.01); *A61B 2017/00353* (2013.01); *A61B 2017/00424* (2013.01); *A61B 2017/00477* (2013.01); *A61B 2017/00526* (2013.01); *A61B 2017/044* (2013.01); *A61B 2017/0409* (2013.01); *A61B 2017/0412* (2013.01); *A61B 2017/0414* (2013.01); *A61B 2017/0445* (2013.01); *A61B 2017/0458* (2013.01); *A61B 2017/0464* (2013.01); *A61B 2017/0496* (2013.01); *A61B 2017/06042* (2013.01); *A61B 2090/034* (2016.02); *A61B 2090/064* (2016.02); *A61F 2002/0841* (2013.01); *A61F 2002/0858* (2013.01); *A61F 2002/0888* (2013.01)

(58) Field of Classification Search
CPC .. A61B 2017/00477; A61B 2017/0496; A61B 2017/06042; A61B 2017/0414; A61B 2017/0445; A61B 2002/0841; A61B 2002/0858; A61B 2002/0888; A61B 2002/0088; A61B 2090/034; A61B 2090/064

See application file for complete search history.

(56) References Cited

U.S. PATENT DOCUMENTS

| | | |
|---|---|---|
| 5,217,486 A | 6/1993 | Rice |
| 5,466,243 A | 11/1995 | Schmieding |
| 5,584,860 A | 12/1996 | Goble |
| 5,827,291 A | 10/1998 | Fucci |
| 5,948,000 A | 9/1999 | Larsen |
| 5,957,953 A | 9/1999 | Dipoto |
| 5,993,459 A | 11/1999 | Larsen |
| 6,319,252 B1 | 11/2001 | McDevitt |
| 6,416,324 B1 | 7/2002 | Day |
| 6,544,281 B2 | 4/2003 | El Attrache et al. |
| 6,641,597 B2 | 11/2003 | Burkhart |
| 6,712,838 B2 | 3/2004 | D'Aversa et al. |
| 7,063,702 B2 | 6/2006 | Michelson |
| 7,322,978 B2 | 1/2008 | West |
| 7,329,264 B2 | 2/2008 | Merves |
| 7,329,271 B2 | 2/2008 | Koyfman et al. |
| 7,357,810 B2 | 4/2008 | Koyfman et al. |
| 7,585,311 B2 | 9/2009 | Green |
| 8,100,942 B1 | 1/2012 | Green et al. |
| 8,202,295 B2 | 6/2012 | Kaplan |
| 8,435,264 B2 | 5/2013 | Sojka |
| 8,465,522 B2 | 6/2013 | Burkhart |
| 8,690,915 B2 | 4/2014 | Hootstein |
| 8,709,040 B2 | 4/2014 | Anderhub |
| 8,758,367 B2 | 6/2014 | Philippon |
| 8,814,905 B2 | 8/2014 | Sengun et al. |
| 8,858,596 B2 | 10/2014 | Robison |
| 9,095,331 B2 | 8/2015 | Hernandez |
| 9,226,817 B2 | 1/2016 | Dougherty |
| 9,370,351 B2 | 6/2016 | Sojka |
| 9,386,976 B2 | 7/2016 | Mayer |
| 9,572,563 B2 | 2/2017 | Berelsman |
| 9,649,104 B2 | 5/2017 | Lunn |
| 9,782,250 B2 * | 10/2017 | Dougherty ............ A61F 2/0805 |
| 10,149,752 B2 * | 12/2018 | Dougherty ............ A61F 2/0811 |
| 10,548,711 B2 * | 2/2020 | Dougherty ......... A61B 17/0483 |
| 2006/0100627 A1 | 5/2006 | Stone et al. |
| 2009/0306671 A1 | 12/2009 | McCormack et al. |
| 2009/0312794 A1 | 12/2009 | Nason |
| 2009/0312795 A1 | 12/2009 | Barbieri |
| 2014/0277128 A1 | 9/2014 | Moore et al. |
| 2016/0367357 A1 | 12/2016 | Dougerty et al. |
| 2016/0374795 A1 | 12/2016 | Dougerty et al. |
| 2017/0000476 A1 | 1/2017 | Dougerty et al. |
| 2017/0150960 A1 | 6/2017 | Dougerty et al. |

OTHER PUBLICATIONS

Product Brochure for "Healix Knotless™ Anchor", DePuy Mitek, Inc., 2012.

"Optimized Sports Medicine Solutions", Parcus Medical, LLC. 2013.

"ReclX STT™Knotless Anchor System", Stryker® Corporation, 2010.

"PopLok 3.5 & 4.5 MM", ConMed Corporation, 2015.

"Value Analysis Brief—Healix Advance™ Knotless Anchor", DePuy Synthes Mitek Sports Medicine, a division of DePuy International Limited, a Johnson & Johnson company, pp. 1-5, 2013.

"Healix Advance™ Knotless Anchor for rotator cuff repair", DePuy Mitek Inc., Johnson & Johnson Medical Limited, pp. 1-4, 2015.

"Healix Knotless™ Suture Anchor", DePuy Mitek, pp. 1-7, Feb. 2012.

\* cited by examiner

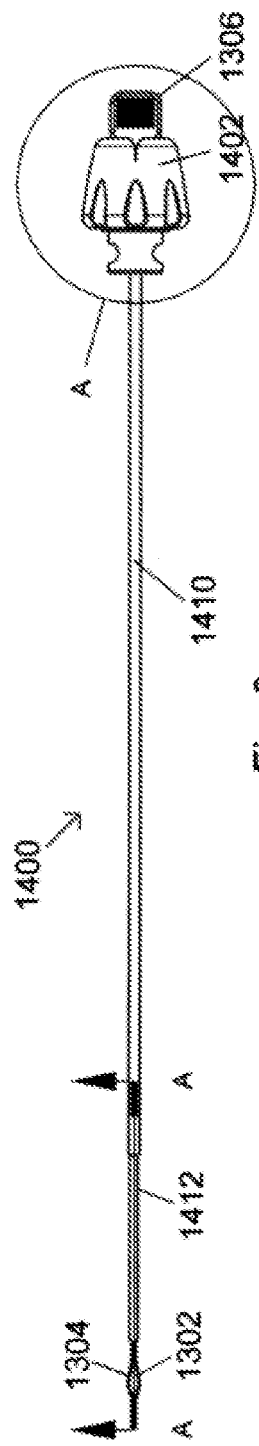
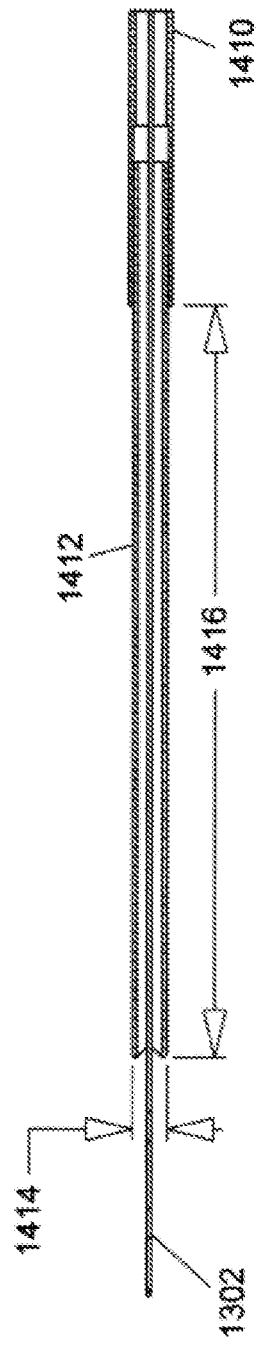
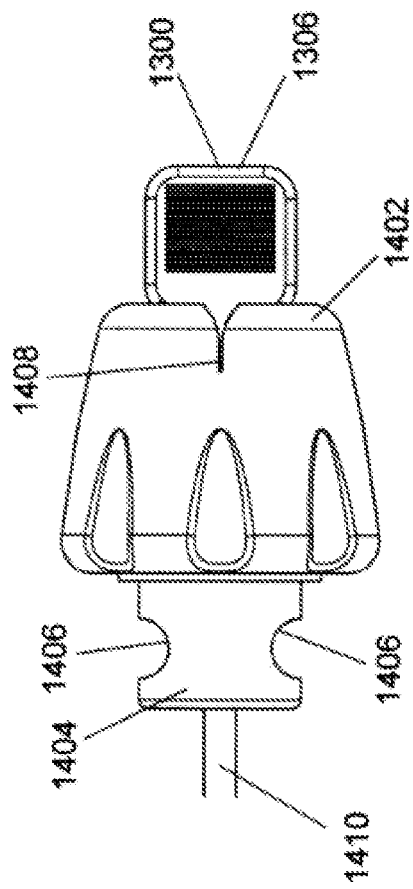
Fig. 3
Fig. 4
Fig. 5

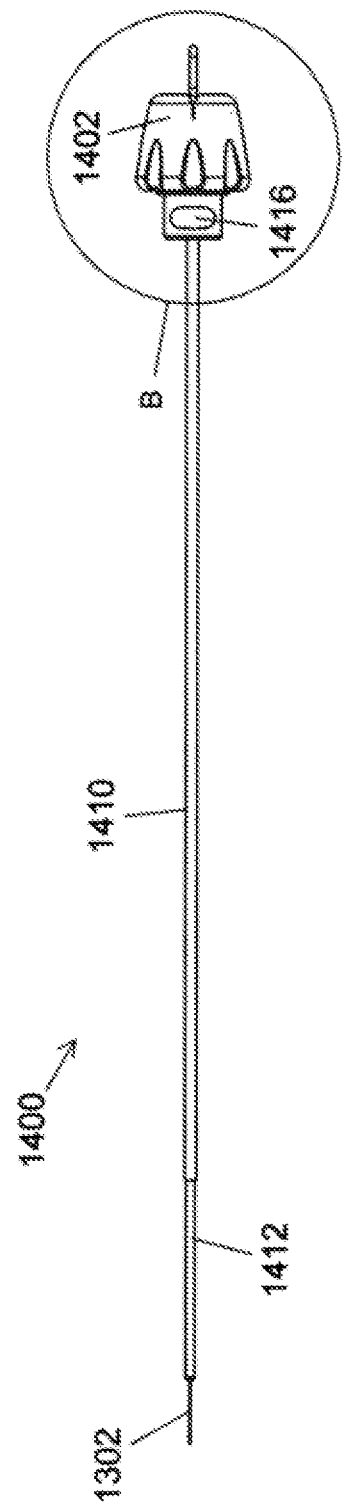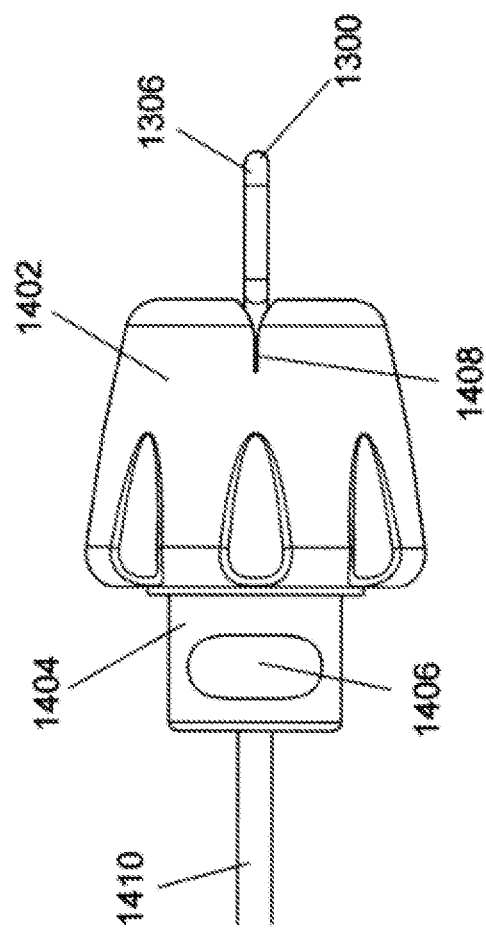
Fig. 6
Fig. 7

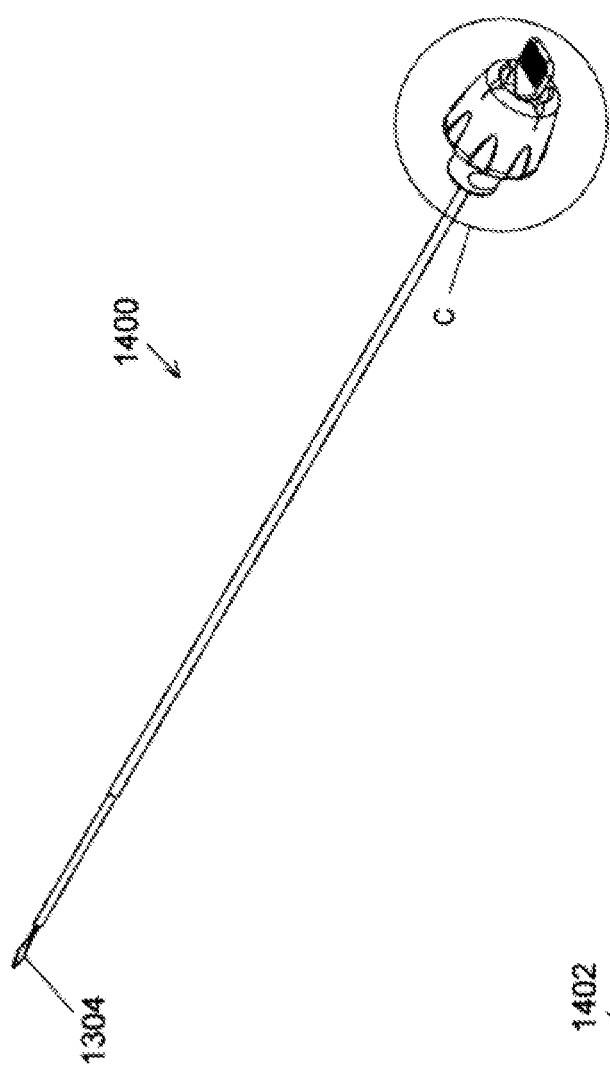
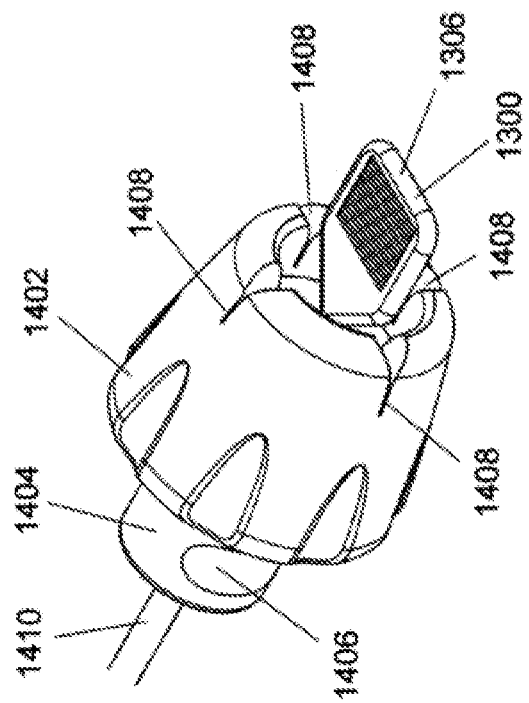

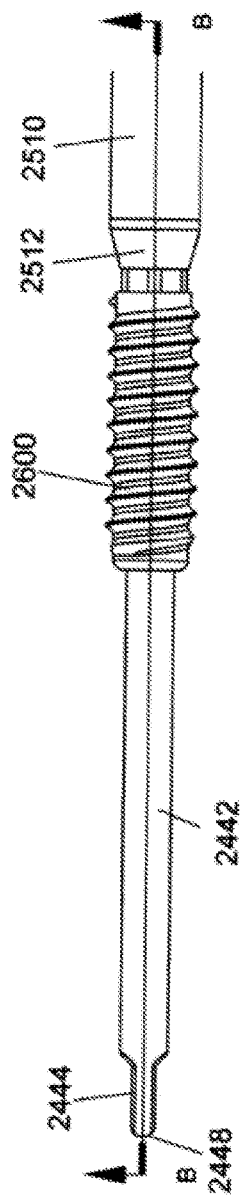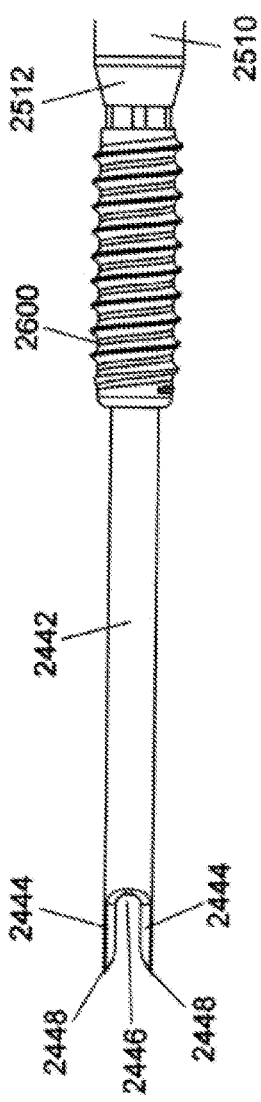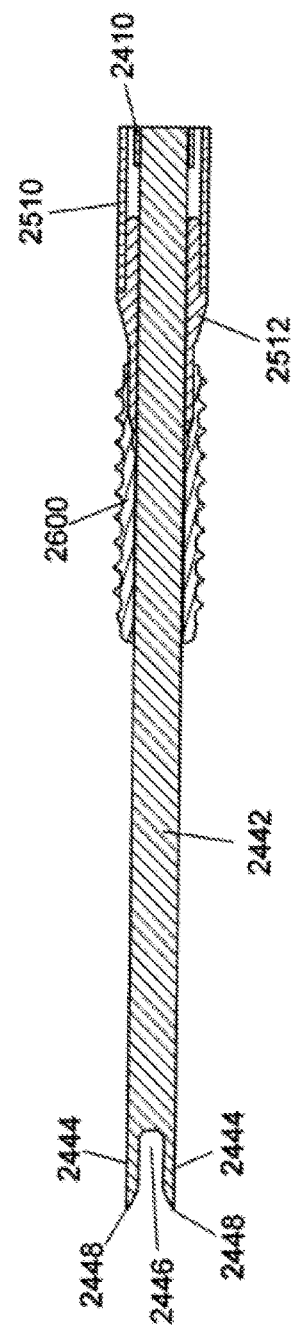

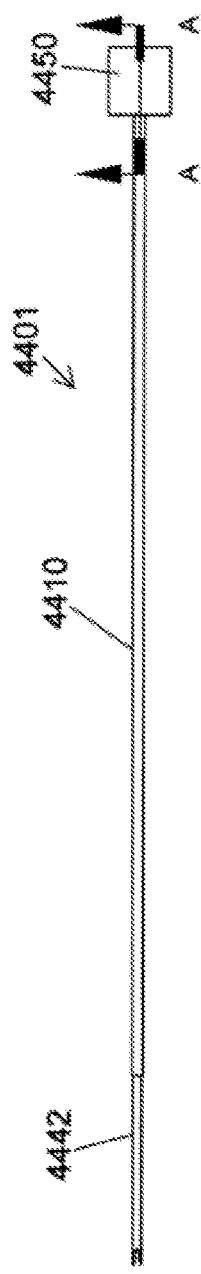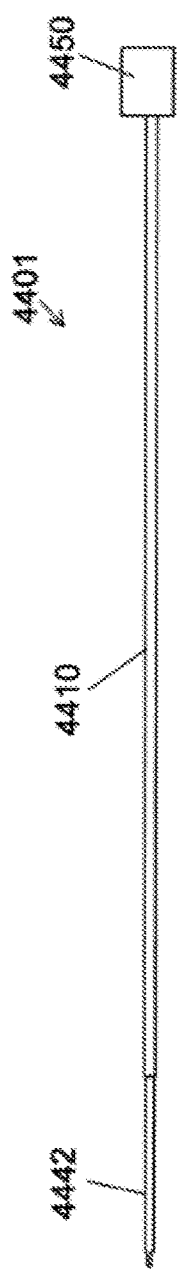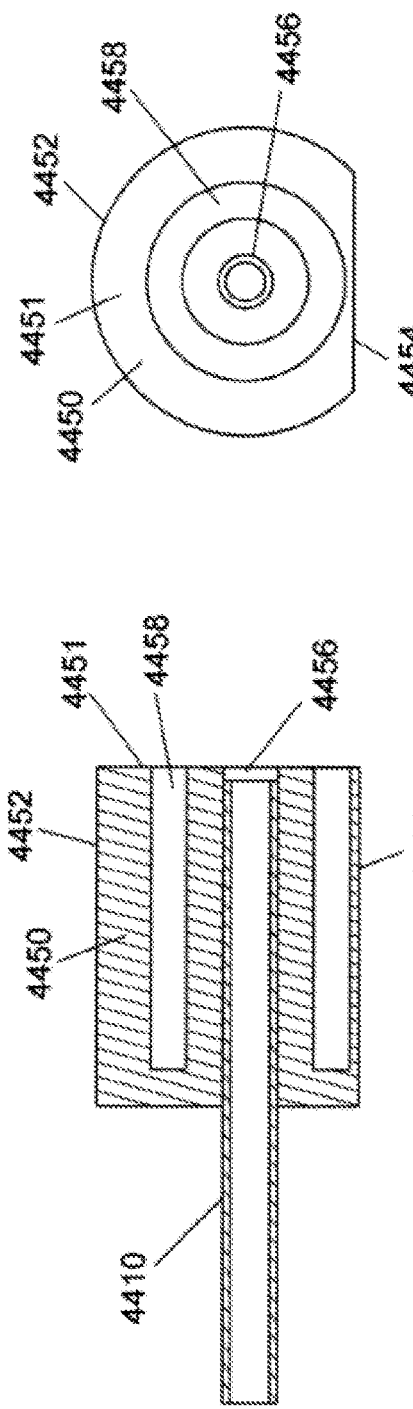

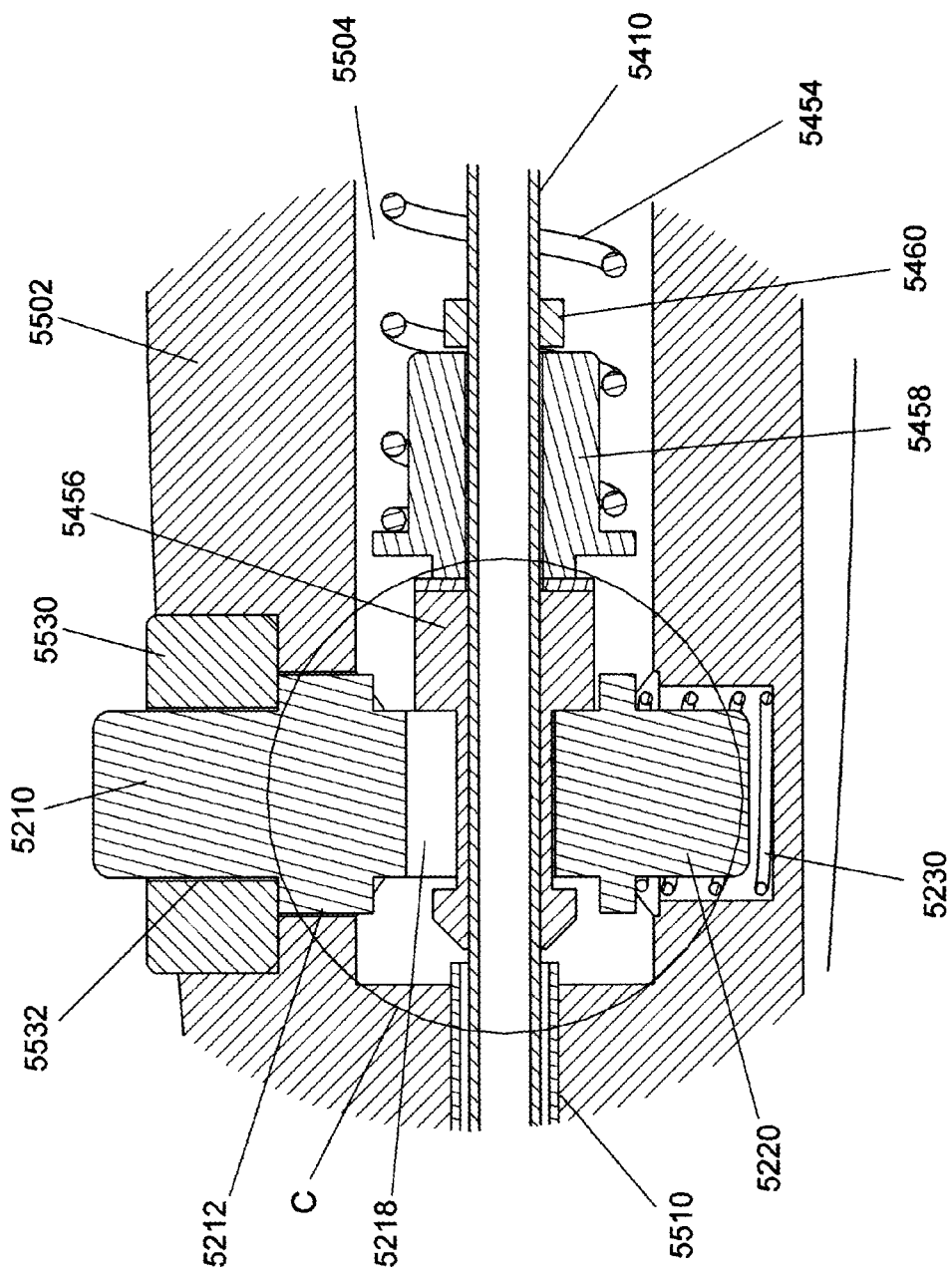

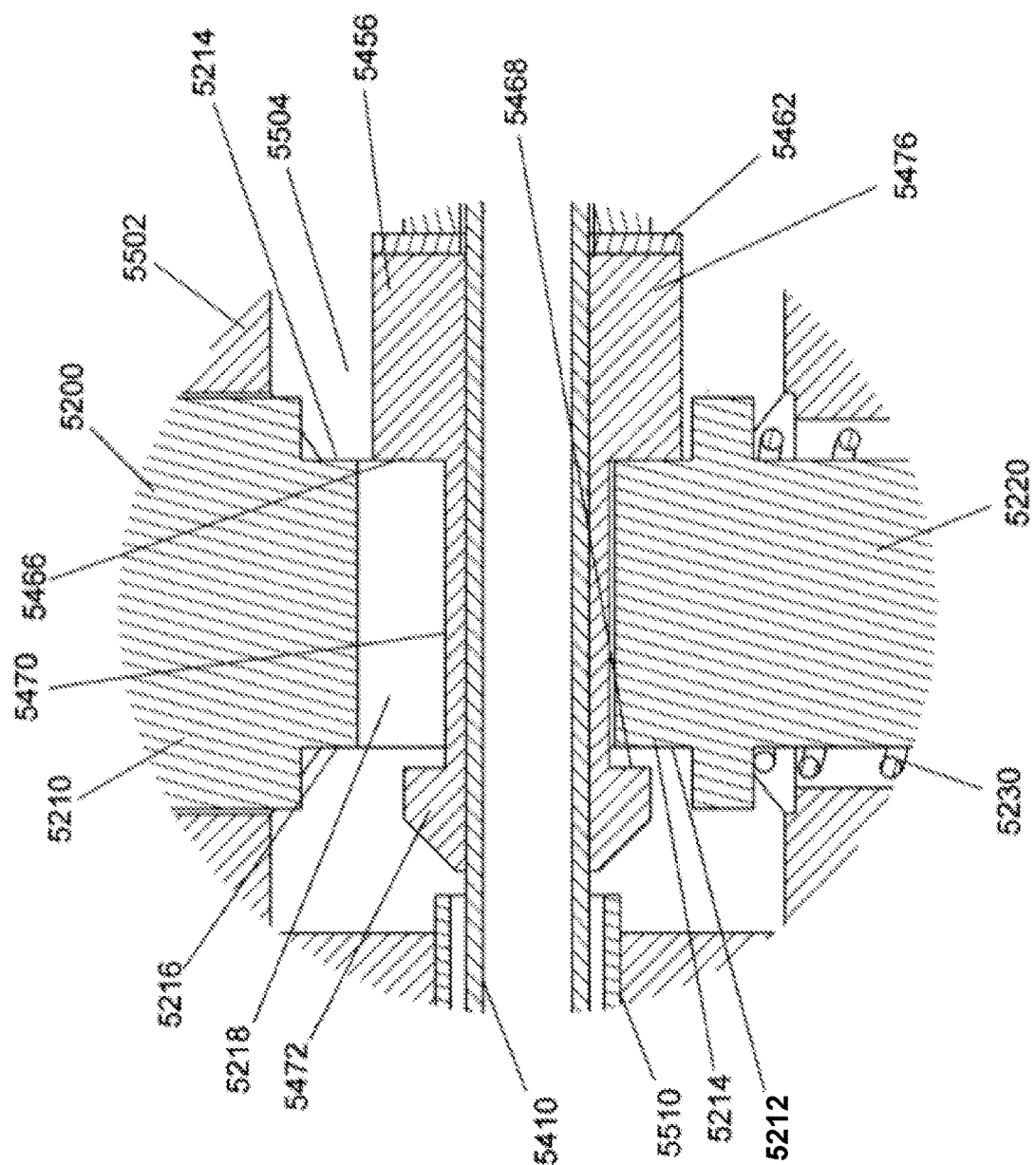

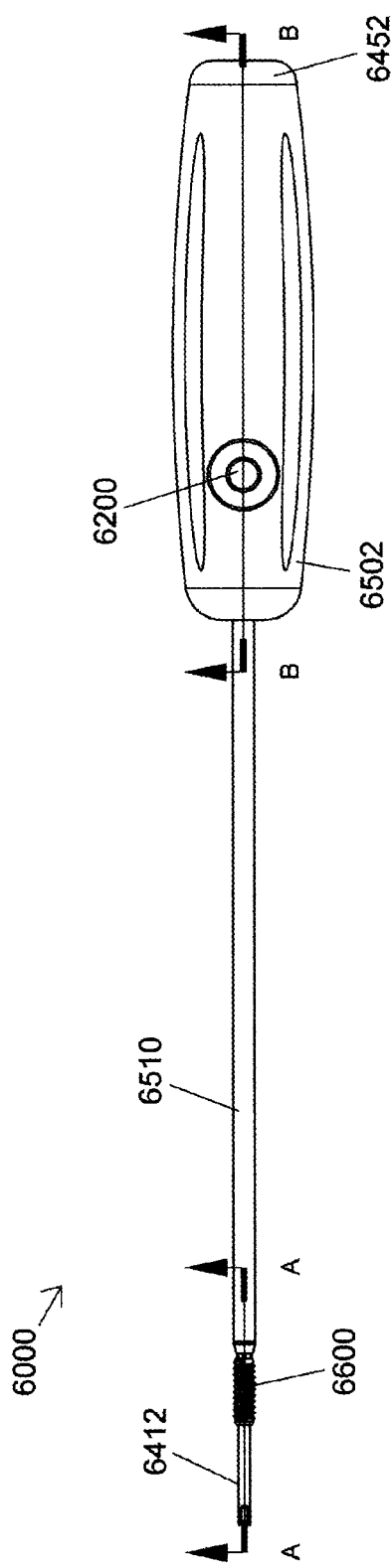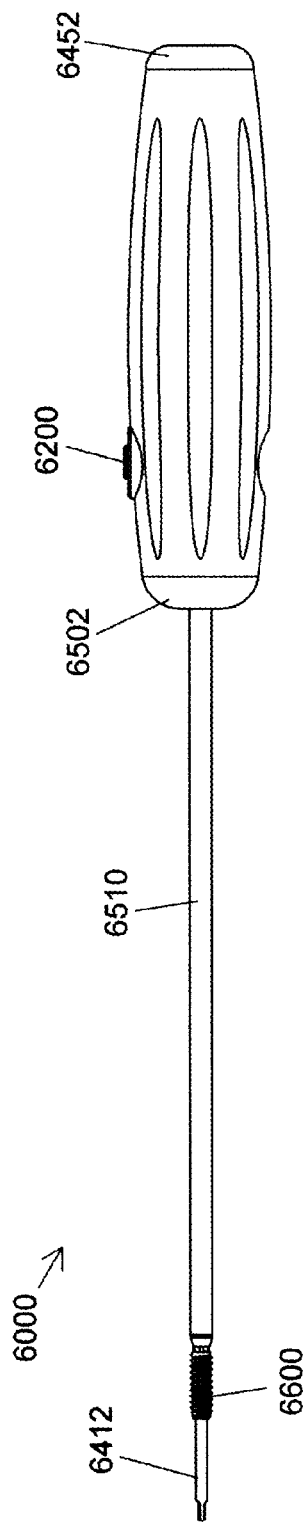
Fig. 107
Fig. 108

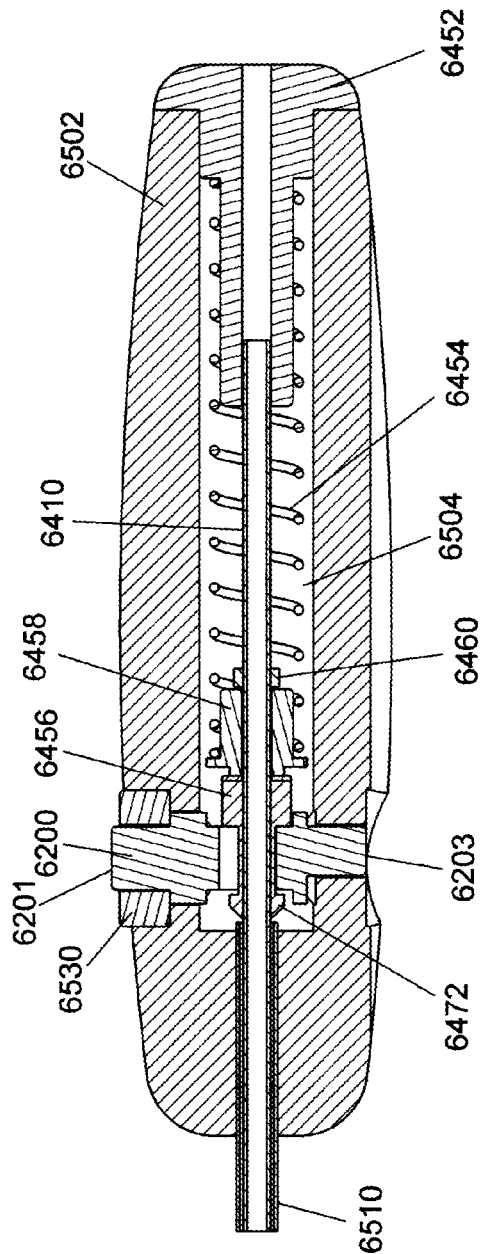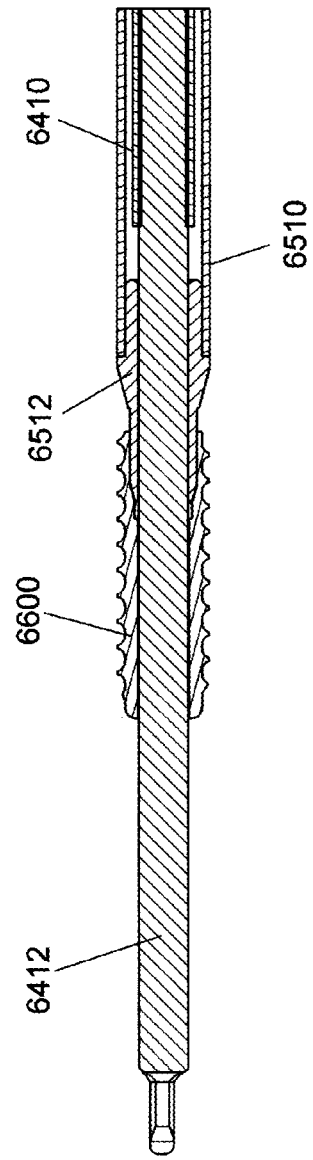
Fig. 109
Fig. 110

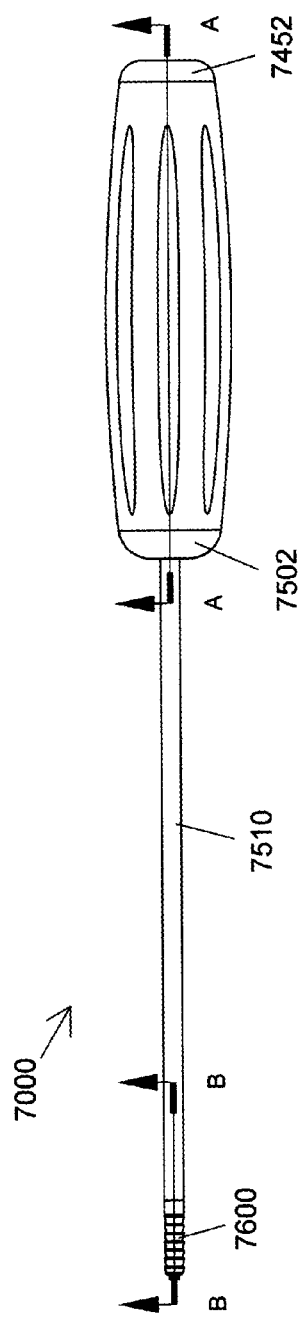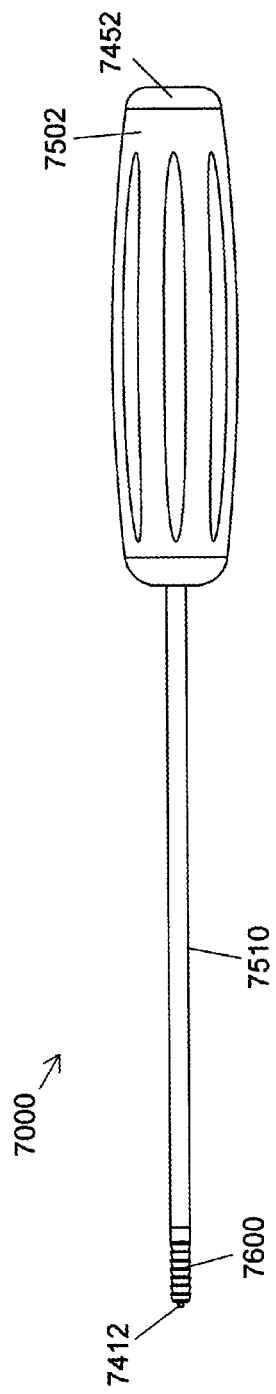
Fig. 123
Fig. 124

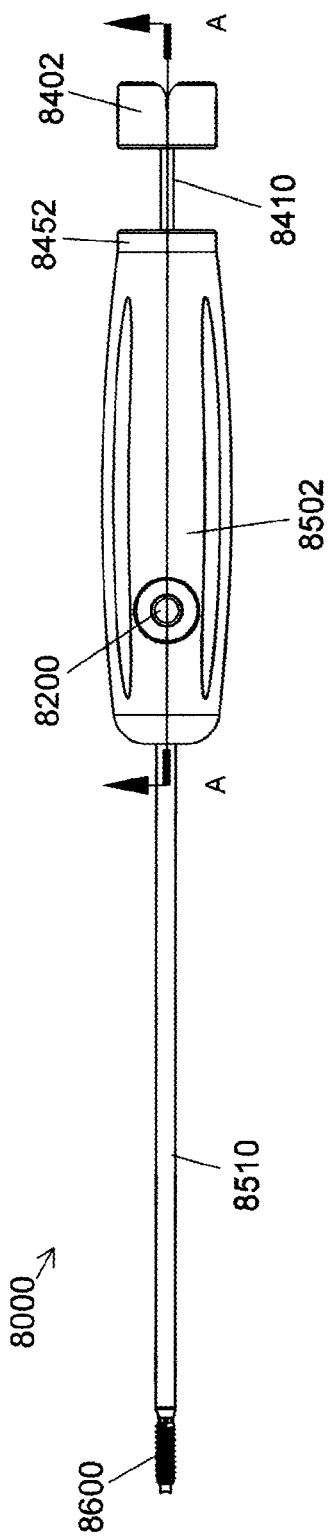
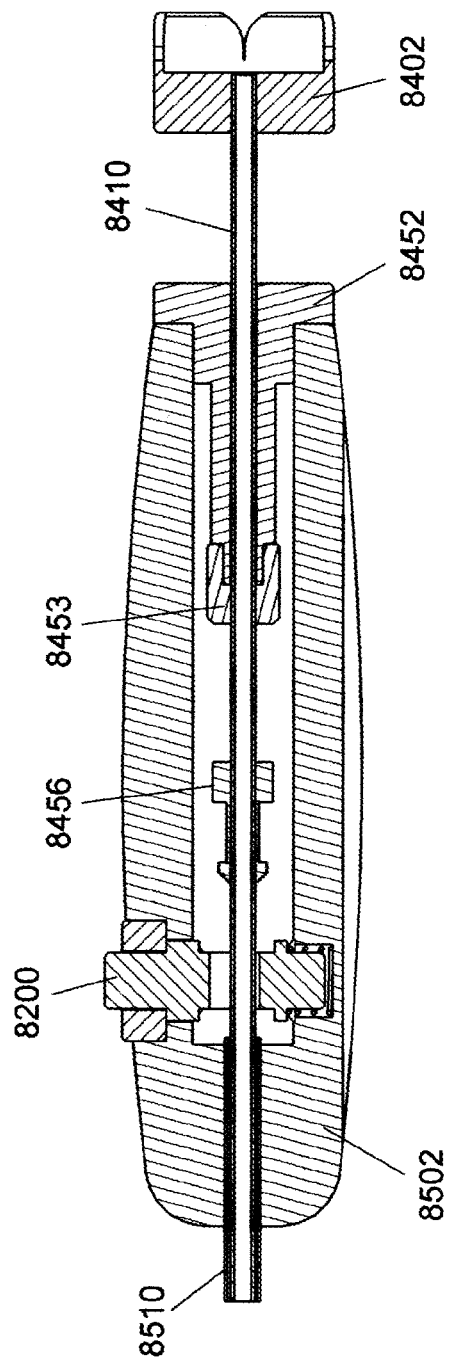
Fig. 132
Fig. 133

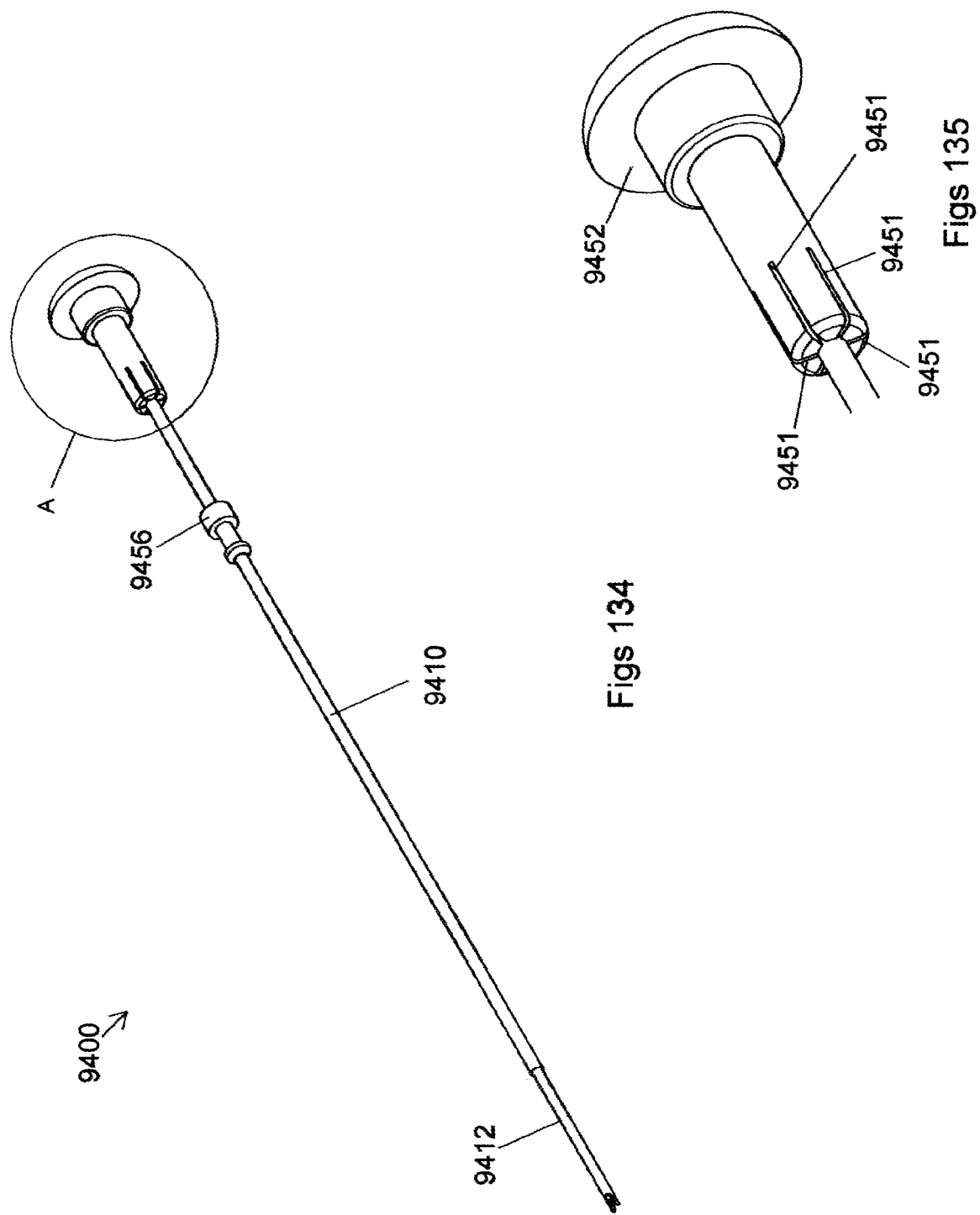

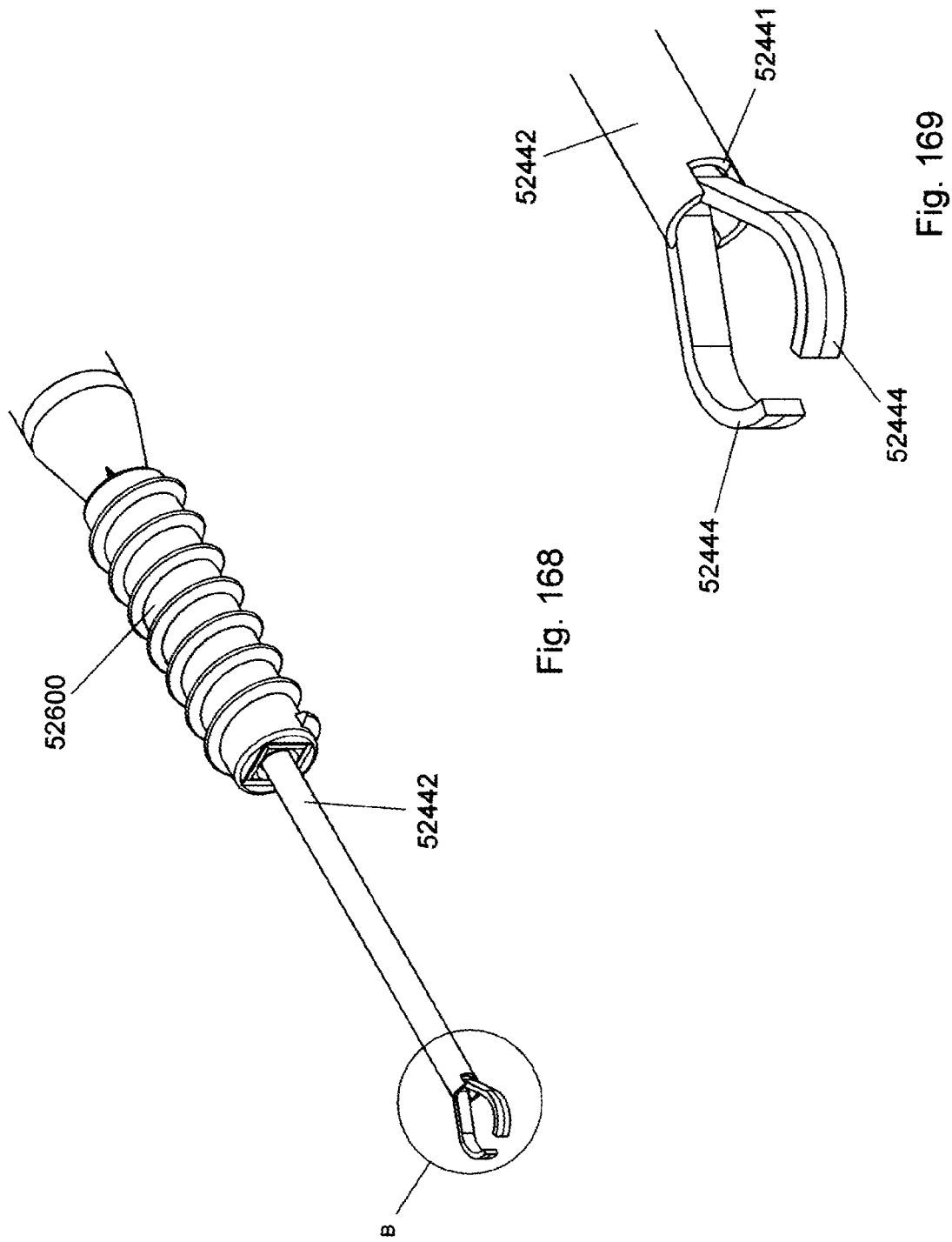

IMPLANT PLACEMENT SYSTEMS AND ONE-HANDED METHODS FOR TISSUE FIXATION USING SAME

PRIORITY

This application is a continuation-in-part of PCT Application No. PCT/US2017/050222 filed Sep. 6, 2017, which, in turn, claims priority to U.S. patent application Ser. No. 15/256,838 filed Sep. 6, 2016 (now U.S. Pat. No. 9,782,250 issued Oct. 10, 2017), which is a continuation-in-part of U.S. patent application Ser. No. 15/012,060 filed Feb. 1, 2016 (now U.S. Pat. No. 9,566,060 issued Feb. 14, 2017), which, in turn, is a continuation-in-part of U.S. patent application Ser. No. 14/972,662 filed Dec. 17, 2015 (now U.S. Pat. No. 9,795,374 issued Oct. 24, 2017), which, in turn, is a continuation of U.S. patent application Ser. No. 14/636,389 filed Mar. 35, 2015 (now U.S. Pat. No. 9,226,817 issued Jan. 5, 2016), which, in turn, claims the benefit of U.S. Provisional Application Ser. No. 61/966,744 filed Mar. 3, 2014; 61/998,391 filed Jun. 26, 2014; 61/998,766 filed Jul. 7, 2014; and 61/999,405 filed Jul. 26, 2014. The afore-mentioned PCT Application No. PCT/US2017/05022, to which the instant application claims priority as a continuation-in part, also claims priority to U.S. patent application Ser. No. 15/429,527 filed Feb. 10, 2017 (now U.S. Pat. No. 9,907,548 issued Mar. 6, 2018). The contents of the afore-noted priority applications are hereby incorporated by reference in their entirety.

TECHNICAL FIELD OF THE INVENTION

The present invention relates generally to the field of endoscopic and arthroscopic surgery and suture anchor systems and devices for use therein. More particularly, the invention relates to a knotless suture anchor device utilized to secure soft tissue to bone or a boney surface to preclude the need to tie surgical knots to secure the tissue in place with the device. Specifically, the invention relates to a simplified anchor system and method by which the surgeon may introduce one or more sutures into a hole in the bone, apply tension to the sutures to advance the soft tissue to a desired location, and then advance the anchor into the bone while maintaining the suture tension and graft position.

BACKGROUND OF THE INVENTION

The use of implants to affix tissue grafts to bone is well known in the orthopedic arts. Common procedures in which such implants are used include, for example, the repair of rotator cuff tears, the repair of torn ligaments in the knee, among others. In these procedures, a socket is drilled or punched in the bone at the attachment site and a graft is secured to the bone using an implant placed in the socket. The graft may be secured to the implant by sutures, or, alternatively, an end of the graft may be placed in the socket and secured directly by an implant.

In rotator cuff repair, implants commonly referred to as "anchors" are used. These anchors occur in two types: conventional anchors in which the suture is passed through the cuff after anchor placement, and "knotless" anchors in which the suture is passed through the cuff prior to anchor placement. In the former case, the graft is secured in place by tying knots in the suture after it has been passed through the cuff so as to secure the cuff in the desired location. Conversely, as the name implies, when a knotless anchor is used, the sutures are passed through the cuff and through a feature of the anchor such that when the anchor is inserted into the socket, the suture position is secured by the anchor. Accordingly, the tying of knots is not required. This is particularly advantageous when performing endoscopic (arthroscopic) repairs since the tying of knots arthroscopically through a small diameter cannula can be difficult for some surgeons and, moreover, there is an opportunity for tangling of the sutures.

Many anchors, both conventional and knotless, are supplied to the surgeon mounted on a driver—a device that the surgeon uses to place the anchor in the prepared socket in the bone. In the case of threaded anchors, the driver has a form like that of a screwdriver, and indeed functions in the same manner. The proximal portion of the device forms a handle that is grasped by the surgeon. Distal to the handle, an elongate distal portion has formed at its distal end features for transmitting torque to an implant. Some anchors, generally metallic anchors such as, for instance, the Revo® Suture Anchor by Conmed Corporation (Utica, N.Y.) and Ti-Screw Suture Anchor by Biomet Corporation (Warsaw, Ind.), have a protruding (male) proximal portion with a cross-section suitable for transmitting torque (typically hexagonal or square) and a transverse eyelet formed therein. The driver for such devices has a complimentary socket (female) formed in its distal end and a cannulation that extends from the interior of the socket to the proximal handle portion of the device. Sutures loaded into the eyelet of the anchor extend through the driver cannulation (or "lumen") and are removably secured to the handle so as to retain the anchor in the socket of the driver. Such anchors are referred to in the orthopedic arts as "pre-loaded", meaning that sutures come loaded into an anchor that is ready for placement by the surgeon using the associated driver.

Other threaded anchors have a socket (female) formed in their proximal ends. Once again, the socket has a cross-section suitable for transmitting torque that is typically polygonal, usually square or hexagonal. Typical of these are the V-LoX™ family of titanium suture anchors by Parcus Medical (Sarasota, Fla.) and the ALLthread™ anchors by Biomet Corporation (Warsaw, Ind.). The drivers for such devices have a protruding (male) torque-transmitting feature complementary to the socket (female) formed in the proximal end of the anchor. These drivers may be cannulated to accommodate sutures that are preloaded into the anchor in the manner previously described, with the sutures being either for the purpose of securing tissue after anchor placement, or for the purpose of removably securing the anchor to the driver, wherein the sutures are released from the driver after the anchor is placed in the bone and subsequently removed and discarded so as to allow removal of the driver from the anchor. The depth of the socket in the proximal end of the implant must be sufficient to enable transmission of the requisite torque needed for anchor placement without deforming or fracturing the implant. As the maximum depth of the torque-transmitting portion is generally limited only by the configuration of the anchor, it is considered to be matter of design choice. Indeed, the implant may have a cannulation that extends axially through the implant as well as a torque-transmitting cross-section forming a substantial proximal portion or the entirety of the implant's length. Implants of the Bio-Tenodesis Screw™ System by Arthrex, Inc have a cannulation with a constant torque-transmitting cross-section, and are used with a driver having a torque-transmitting portion that extends beyond the distal end of the anchor, wherein the portion of the driver extending beyond the anchor and a suture loop in the driver cannulation are used together to insert the end of a graft into a prepared socket prior to placement of the implant.

Knotless suture anchor fixation is a common way of repairing soft tissue that has been torn from bone. Illustrative examples of such "knotless" anchors include the Allthread™ Knotless Anchors by Biomet Incorporated (Warsaw, Ind.), the SwiveLock® Knotless Anchor system by Arthrex, Incorporated (Naples, Fla.), the HEALIX Knotless™ Anchors by Depuy/Mitek, Incorporated (Raynham, Mass.) and the Knotless Push-In Anchors such as the Knotless PEEK CF Anchor by Parcus Medical (Sarasota, Fla.). The procedure requires drilling or punching of holes into a properly prepared boney surface. After suture has been passed through soft tissue, the suture anchor is introduced into the socket and driven into the socket using a mallet or by screwing the anchor into the socket using a driver device. These driver devices typically resemble a screwdriver in form, having a proximal handle portion for applying torque or percussive force, and an elongate rigid distal portion having at its distal end a torque or percussive force-transmitting configuration. In the case of torque-transmitting drivers used with threaded anchors, the distal end of the driver typically has an elongate hexagonal or square distally extending portion that, through coupling with a lumen in the anchor having a complementary cross-section, transmits torque to the anchor. The lumen may extend through anchor so that the distal portion of the driver protrudes from the distal end of the anchor and rotates with the anchor during anchor placement.

Because the suture is drawn into the prepared socket along with the anchor during anchor placement, it is essential that a suitable length of suture extends between the graft and the anchor so that when the anchor is suitably positioned within the socket, the graft is properly positioned. Determining the proper length of suture to allow between the anchor and the graft so as to achieve optimal graft positioning is complicated since suture(s) may twist (a process referred to in the orthopedic arts as "suture spin") during anchor placement, thereby shortening the effective length and changing the final graft position and/or undesirably increasing the suture tension.

U.S. Pat. No. 6,544,281 to ElAttrache et al. describes a cannulated anchor placement system having a rotating inner member (which acts as the driver) and a stationary outer member, wherein the rotating inner member serves to drive the threaded anchor. The rotating "driver" extends past the distal end of the anchor and is inserted into a prepared socket in the boney surface. A suture loop formed distal to the distal end of the driver "captures" or "secures" sutures attached to a graft or the graft itself to the distal end of the driver. The distal end of the driver is then inserted into the socket to a proper depth for anchor placement thereby drawing the graft to the desired position prior to placement of the anchor. The anchor is then threaded into the socket to the predetermined depth. This system constitutes an improvement over other commercially available alternatives. However, because the graft or sutures are secured to or pass through the distal end of the rotating inner (or "driver"), torque is transmitted not only to the anchor but also to the graft or sutures attached thereto by the suture loop. Accordingly, twisting of the sutures or graft frequently occurs, thereby changing the resulting suture tension and/or the graft position (a process referred to in the orthopedic arts as "graft shift").

U.S. Pat. No. 8,663,279 by Burkhart et al. describes a knotless anchor system similar in construction to that of ElAttrache et al. A "swivel" implant having formed therein an eyelet is releasably and pivotably mounted to the distal end of a driver distal portion that extends distally beyond the distal end of an anchor. After sutures are passed through the graft, they are threaded into the eyelet of the swivel implant at the distal end of the driver. The distal end of the driver with the swivel implant is then inserted into the socket. By pulling on the suture tails, the graft is moved into position and secured by screwing the anchor into the socket. However, because the sutures/graft are secured to the driver by means of the swivel eyelet implant, the torque that may be transmitted to the sutures/graft is limited. However, torque transmission is not eliminated since the swivel implant is retained in the driver distal end by a suture loop under tension, which extends through the cannula of the driver to the driver's proximal end where the suture ends are cleated. While an improvement over the ElAttrache anchor system, suture spin is not eliminated in all cases, and indeed, cannot be since the suture-retaining implant is mounted to the driver, which rotates during anchor placement. As such, some level of torque transmission due to friction between the driver distal end and the swivel eyelet implant is inevitable.

Other knotless anchors such as the ReelX STT™ Knotless Anchor System by Stryker® Corporation (Kalamazoo, Mich.) and PopLok® Knotless Anchors by ConMed Corporation (Utica, N.Y.) have complex constructions and require that the surgeon perform a sequence of steps to achieve a successful anchor placement with the desired suture tension and proper cuff position. The sequence of steps adds to procedure time and creates opportunities for failure of the placement procedure if a step is not performed properly.

Accordingly, there is a need in the orthopedic arts for a knotless anchor system that allows the surgeon to establish the graft position, and, while maintaining that position, place the anchor without changing the suture tension or causing a shift in the graft position due to suture spin. Furthermore, if the anchor is threaded, placement of the anchor in the socket must occur without spinning of the suture.

In cases where a graft, such as a biceps tendon, is to be directly affixed to a bone by insertion of the graft into a socket (a technique referred to in the art as "bio-tenodesis"), it is essential that the graft be fully inserted into the socket so as to be engaged by the full length of the implant. It is also important that the position of the graft be maintained during anchor insertion. Further, it is essential that the alignment of the implant (referred to in this case as an "interference screw") be coaxial, or if slightly shifted, parallel to the axis of the socket. It is also desirable that the sutures used to draw the graft into the socket do not spin or twist during anchor placement as this may change the position and tension of the graft from that intended by the surgeon. In sum, there is a also need in the suture arts for an interference screw and implant placement system in which graft position within the socket is maintained throughout the implant placement process, and in which suture spin or twisting is prevented.

SUMMARY OF THE INVENTION

A primary objective of the present invention is to provide improved means and methods of attaching soft tissues (i.e., "grafts") to bone in situ. The embodiments of the present invention described hereinbelow relate to a system and method for the placement of a simple one-piece cannulated anchor or for producing a matrix of implants for the anchoring of a graft to bone. Any graft fixation system that uses an implant placement system with an optionally cannulated, non-rotating tensioning device (i.e., the relatively fixed "inner assembly") positioned within a cannulation or "lumen" of a cannulated driver (i.e., the relatively movable "outer assembly") to tension sutures in a prepared socket for the placement of a simple one-piece cannulated anchor are contemplated by the present invention. Illustrative aspects and embodiments of the present invention in accordance with the foregoing objective are as follows:

In a first aspect, the present invention provides prosthetic implants and systems for their placement in a target boney surface for the knotless securing of a soft tissue graft thereto. The present invention contemplates a novel placement system including a non-rotating, cannulated tensioning device ("inner assembly") positioned within a rotationally and axially movable cannulated driver ("outer assembly"). In a preferred embodiment, a tubular distal element of the tensioning device extends distally beyond the distal end of the cannulated driver. A cannulated threaded implant (or "anchor") is removably mounted to the torque-transmitting distal portion of the driver. Sutures placed in the graft are drawn into the distal end of the elongate distal portion of the cannulated tensioning device, which extends beyond the distal end of the implant. If a threaded implant is used, the distal end of the cannulated driver preferably includes torque-transmitting features that, together with complementary features formed in the proximal portion of the implant or anchor, allow the transmission of torque thereto. If an interference plug-type anchor is used, the distal end of the driver is preferably configured to transmit axial force to the anchor, the proximal end of which has a suitably complementary configuration to enable secure attachment.

In operation, sutures placed in the graft are drawn into the distal end of the tensioning device. The elongate distal portion of tensioning device is inserted into a properly prepared socket in the target boney surface so that the distal end of the tensioning device, with its sutures is positioned at the bottom of the socket. Tension is then applied to the sutures by pulling on their proximal ends, which extend beyond the proximal portion of the tensioning device, to move the graft into the desired position, namely into the prepared socket adjacent to the distal element of the tensioning device. The desired tension may be maintained by cleating proximal portions of the suture(s) into slots optionally formed in the handle of the tensioning device. The anchor (or interference screw) may then be screwed, threaded or otherwise driven into the socket, thereby trapping the sutures or graft between the anchor exterior surface and the socket wall. Critically, twisting of the suture(s) or graft(s) is prevented by means of the non-rotating distal tubular portion of the tensioning device that remains distal to the anchor distal end during anchor placement. In addition, the tension on the sutures and the position of the graft are maintained during placement of the anchor throughout the procedure. After anchor placement, the driver and tensioning device are withdrawn, removed from the site, at which point the sutures may be trimmed to complete the procedure.

In contrast to the Burkhart and ElAttrache anchor systems, suture tensioning and establishment of the graft position are not accomplished using the driver's distal end or using an implant positioned in the driver's distal end. Rather, suture tension and graft position are established and maintained by the distal portion of a non-rotating tensioning device ("inner assembly") that extends beyond the driver ("outer assembly") and anchor distal ends. Because of this, the transmission of torque to the sutures and/or graft by the driver present in the Burkhart and ElAttrache systems is eliminated, along with its associated suture or graft spin.

The system and method of the present invention provide a simplification over other currently available anchoring methods and hardware in that fewer steps are required and moreover the anchor has a simple, single-piece construction. The anchor system is scalable and, due to its simple construction, may be used with anchors smaller than those permitted using other currently available systems. The composition and construction in the anchor may be readily modified simply by changing the material from which it is constructed, by increasing or reducing the diameter or length of the anchor, by increasing or decreasing the wall thickness of the anchor, by modifying the profile of the exterior, or by any combination of these means. All such modifications are contemplated as within the scope of the present invention.

In another aspect, the present invention provides a method for affixing a soft tissue graft to a target boney surface, the method including the steps of:

a. providing a placement system having a cannulated, non-rotating tensioning device ("inner assembly") and a cannulated driver ("outer assembly"), wherein the tensioning device is positioned within the cannulation or "lumen" of the driver device, b. positioning a cannulated anchor onto the distal torque-transmitting portion of the driver, over a distally extending element of the tensioning device, c. producing a suitably configured hole (i.e., "socket") in a prepared boney surface at a desired target location using a drill, tap, punch or equivalent hole-producing device, d. drawing sutures from the graft into the lumen of the tensioning device, e. inserting the distal end of the tensioning device into the socket, f. applying tension to the sutures to draw the graft to a desired position, g. placing the anchor (or interference screw) in the socket, h. withdrawing the placement system, i. trimming the suture tails, and j. optionally repeating steps (c) through (i) as required.

In an alternate embodiment of the present invention, identical in all aspects to the previous embodiment except as subsequently described, the tubular distal portion of the tensioning device is replaced by a rod having formed at its distal end a sharpened fork portion. Two (or more) parallel, axially extending tines form the fork, the tines being spaced apart so that sutures may slide freely through the channel(s) formed between the tines. An anchor placement system commensurate with such an embodiment is used in the following manner: First, a cannulated threaded implant is removably mounted to the torque-transmitting distal portion of the driver. Sutures placed in the graft are then positioned in the channel(s) of the distal fork portion of the tensioning device. The elongate distal portion of the tensioning device with the sutures positioned within its distal channel is then inserted into a prepared socket so that the distal end of the tensioning device with its sutures is positioned at the bottom of the socket. Tension is then applied to the sutures by pulling on their proximal ends to draw the graft into the desired position. The desired tension and graft position may be maintained by cleating the suture proximal portions in slots optionally formed in the handle of the tensioning device. The anchor is then screwed, threaded or otherwise axially driven into the socket by the driver, thereby trapping the sutures or graft between the anchor exterior surface and the socket wall. Twisting of the sutures or the graft is prevented by the non-rotating distal fork portion of the tensioning device that remains distal to the anchor distal end during anchor placement. The tension on the sutures and the position of the graft are maintained during placement of the anchor. After anchor placement, the driver and tensioning device are removed from the site and the sutures trimmed to complete the procedure.

In certain embodiments that are particularly applicable to small diameter implants, the tensioning device may be cannulated and coupled with an elongate element formed from a suitable shape memory metal and/or superelastic polymeric material that, in a first configuration, is provided with a suture retention loop at its distal end. The distal end of the elongate element extends out of and distally away from the distal end of the cannulated tensioning device so as to be accessible to free suture ends. In operation, one or more sutures are loaded into the distal retention loop. The sutures are then tensioned and secured as previously described, through cooperation of the cannulated tensioning device, cannulated anchoring implant and torque-transmitting driver device. After the implant is properly placed, the elongate element may be readily transformed into a second relatively linear configuration and axially withdrawn from the tensioning lumen. As noted elsewhere, the elongate element may preferably take the form of a nitinol wire.

An implant placement system of the present embodiment may also include a mechanism for releasably preventing relative axial and rotational movement between the driver ("outer assembly") and the tensioning device ("inner assembly"), such means optionally positioned within the cannulation (or "lumen") of the driver. In a first condition, used during tensioning of the suture, relative axial and rotational motion is of the driver relative to the tensioning device is prevented. In a second condition, used during placement of the anchor, the driver may be advanced axially on the tensioning device to bring the anchor to the socket, and rotated to screw the anchor into the socket, with the tensioning device remaining stationery so as to maintain suture tension and prevent twisting of the sutures.

In a particularly preferred embodiment, prevention of relative motion is provided by a removable key having one or more protrusions, coupled with features formed on the handles of the tensioning device and driver such that, when the features are in alignment, engagement by the one or more protrusions of the key prevents relative axial or rotational movement between the torque-transmitting driver and the tensioning device. Removal of the key allows the driver to be advanced distally and rotated relative to the tensioning device. Other embodiments are anticipated in which other means are used to releasably prevent relative motion.

Certain preferred embodiments of the present invention are configured for one-handed operation by the surgeon. In these embodiments, a suitable tensioning device is an inner assembly that is irremovably (i.e., permanently) affixed to and/or positioned within an associated driver device ("outer assembly"), wherein the driver is axially movable between a first proximal position and a second distal position relative to the tensioning device. In the first proximal position, the distal portion of the tensioning device extends distally beyond the implant so as to allow tensioning of sutures and positioning of a graft as described previously herein as well as in related co-pending applications incorporated herein by reference. Advancing the driver distally toward its second, distal position brings the implant to the prepared socket in preparation for placement. Thereafter, the implant is threaded or axially driven into the socket. Distal motion by the driver device ("outer assembly") relative to the tensioning device ("inner assembly") may be resisted by a spring within the driver handle or, alternatively, by other motion resistive means such as, for instance, a friction producing element. However produced, the resistance to distal motion is sufficient to ensure that the distal end of the tensioning device remains in contact with the bottom of the socket to maintain graft position and to prevent rotation of the tensioning device during anchor placement.

In yet another aspect, like the previous in all other respects except as subsequently described, the suture attached to the graft is positioned within the distal fork and tensioned such that a first end of the graft is adjacent to the fork, with the tension optionally being maintained by cleating of the sutures on the tensioning device handle. The distal portion of the tensioning device with the graft is inserted into the prepared socket. The anchor is then threaded or driven into the socket as previously described, thereby directly trapping a portion of the graft that is adjacent to the first end of the graft between the anchor exterior surface and a first portion of the socket wall, with the attached sutures disposed between the anchor exterior surface and a second, laterally opposed portion of the socket wall.

In a variation of the previous aspect, the graft may be pierced by the sharpened, distally extending "tines" of the distal fork. The distal portion of the tensioning element with the graft is inserted into the prepared socket. Once again, the anchor is then threaded or driven into the socket, thereby directly trapping a proximal portion of the graft between the anchor exterior surface and a portion of the socket wall.

In another variation of the previous aspect, the graft is pierced by the sharpened distally extending "tines" of the distal fork a predetermined distance from the graft distal end such that, when the distal portion of the tensioning element with the graft is inserted into the prepared socket, the proximal end of the graft protrudes above the opening of the socket. The anchor is then threaded or driven into the socket so as to once again directly trap the graft proximal portion between the anchor exterior surface and first and second laterally opposed portions of the socket wall.

In another variation of the previous two aspects, the distal fork is replaced by a single, sharpened, protruding portion configured for penetration of a graft. Optionally, a "washer" formed of a suitable material is removably mounted on the sharpened protruding portion to limit the depth of penetration of the sharpened portion into the graft. When the anchor is placed, this depth-limiting washer remains in the socket positioned distal to the anchor, between the anchor and the graft.

In another variation of the present invention, the distal fork is configured not for tissue penetration, but rather for the retention of sutures placed therein during tensioning, with the distally extending portions forming a suture-retaining, split loop that defines a distal gap that allows for the placement of sutures therein and their exit after anchor placement. In certain preferred embodiments the distally extending portions are formed of a resilient polymeric material or are formed of elastically deformable wires, such that the portions may be inwardly deflected during withdrawal of the placement system after anchor placement.

In still yet another aspect, identical in form to the devices and insertion systems previously herein described, the tensioning device has a proximal handle portion that is an assembly of first and second rigid elements with an elastic element positioned therebetween. Applying a distal force to a first rigid element of the handle of the tensioning device causes deflection of the elastic element proportional to the tension in the graft attached to the distal fork. This allows the practitioner to measure the tension in the graft. By establishing the tension in the graft to a predetermined value prior to placement of the anchor, the tension may then be maintained at the predetermined value during anchor placement.

In sum, any graft fixation system that couples a non-rotating inner member (herein referred to interchangeably as "tensioning device" and "inner assembly") with a movable outer member (herein referred to interchangeably as "driver", "driver device", and "outer assembly") to tension sutures in a prepared socket for the placement of a simple, one-piece cannulated anchor is considered to fall within the scope of the present invention.

These and other aspects are accomplished in the invention herein described, directed to a system and method for producing one or a plurality of implants for the anchoring of a graft to bone. Further objects and features of the invention will become more fully apparent when the following detailed description is read in conjunction with the accompanying figures and examples. To that end, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 3 is a plan view of a tensioning device illustrative of an implant placement system of the present invention.

FIG. 4 is an expanded sectional view of the tensioning device of FIG. 3 at location A-A.

FIG. 5 is an expanded view of the proximal hub portion of the tensioning device of FIG. 3 at location A.

FIG. 6 is a side elevational view of the objects of FIG. 3.

FIG. 7 is an expanded view of the objects of FIG. 6 at location B.

FIG. 8 is a perspective view of the tensioning device of FIG. 3.

FIG. 9 is an expanded view of the objects of FIG. 8 at location C.

FIG. 36 is an expanded plan view of the distal portion of the elements of FIG. 33.

FIG. 37 is a side elevational view of the objects of FIG. 36.

FIG. 38 is a sectional view of the objects of FIG. 36 at location B-B.

FIG. 64 is a plan view of a distal assembly for the tensioning device in an alternate embodiment of an implant placement system contemplated by the present invention, one that includes a force-indicating inner tensioning assembly.

FIG. 65 is a side elevational view of the objects of FIG. 64.

FIG. 66 is a sectional view of the objects of FIG. 64 at location A-A.

FIG. 67 is an expanded proximal axial view of the objects of FIG. 64.

FIG. 98B is an expanded view of the objects of FIG. 98A at location A.

FIG. 98C is an expanded view of the objects of FIG. 98B at location C.

FIG. 107 is a plan view of the implant placement system of FIG. 106.

FIG. 108 is a side elevational view of the objects of FIG. 106.

FIG. 109 is an expanded sectional view of the objects of FIG. 107 at location B-B.

FIG. 110 is an expanded sectional view of the objects of FIG. 107 at location A-A.

FIG. 112 is a plan view of the objects of FIG. 111.

FIG. 113 is a side elevational view of the objects of FIG. 111.

FIG. 114 is an expanded sectional view of the objects of FIG. 112 at location B-B.

FIG. 115 is an expanded sectional view of the objects of FIG. 112 at location A-A.

FIG. 116 is a perspective view of the exploded assembly of an alternate embodiment implant placement system of the present invention.

FIG. 117 is a perspective view of an alternate embodiment of an implant placement system of the present invention, one formed from the elements and assemblies of FIG. 116 with the distal portion of the inner tensioning assembly protruding beyond the implant in preparation for implant placement.

FIG. 118 is a plan view of the objects of FIG. 117.

FIG. 119 is a side elevational view of the objects of FIG. 117.

FIG. 120 is an expanded sectional view of the objects of FIG. 118 at location B-B.

FIG. 121 is an expanded sectional view of the objects of FIG. 118 at location A-A.

FIG. 122 is a perspective view of the implant placement system of FIG. 117 with the outer driver assembly and implant advanced on the inner tensioning assembly as when an implant is fully place in a socket.

FIG. 123 is a plan view of the objects of FIG. 122.

Figure 122:
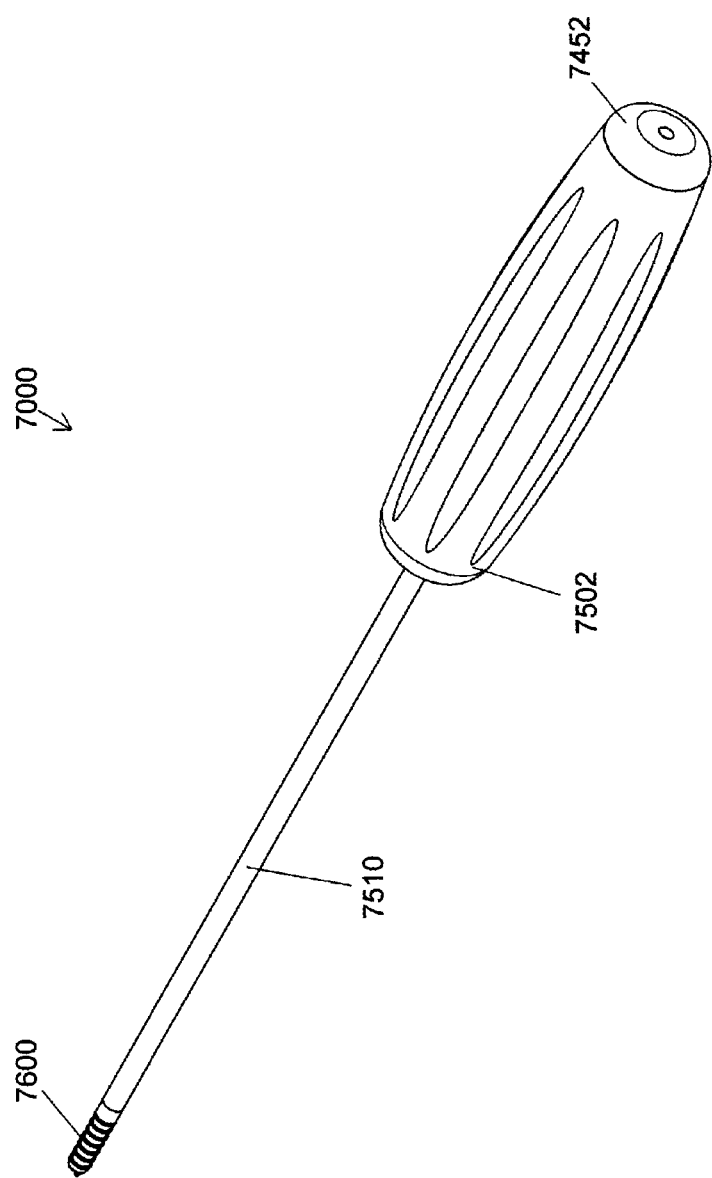

FIG. 124 is a side elevational view of the objects of FIG. 122.

Figure 125:
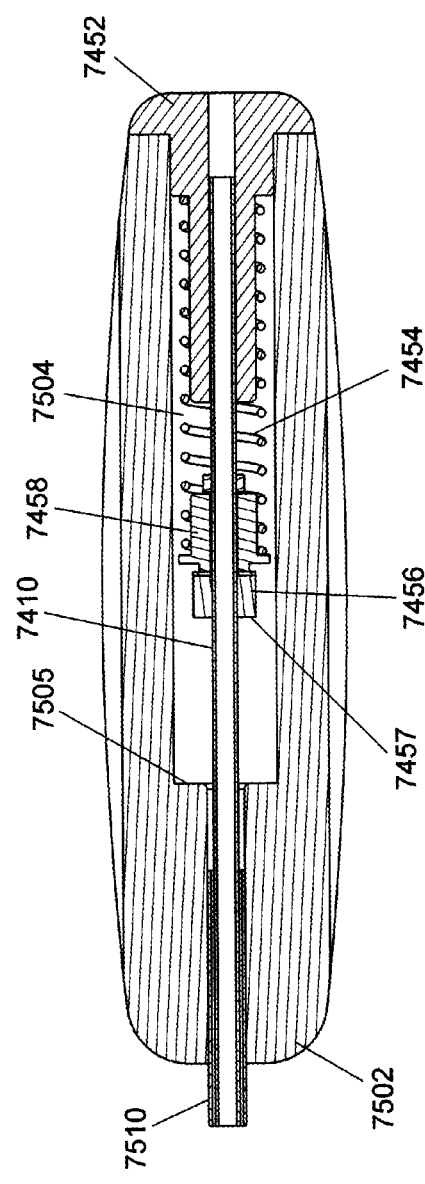

FIG. 125 is an expanded sectional view of the objects of FIG. 123 at location A-A.

Figure 126:
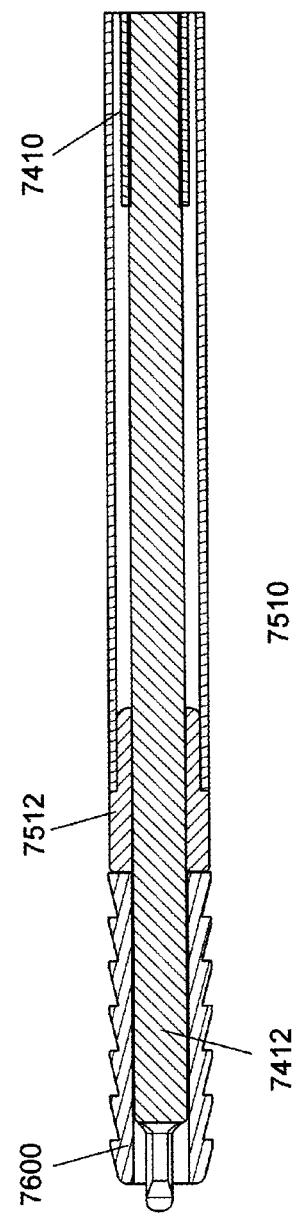

FIG. 126 is an expanded sectional view of the objects of FIG. 123 at location B-B.

Figure 127:
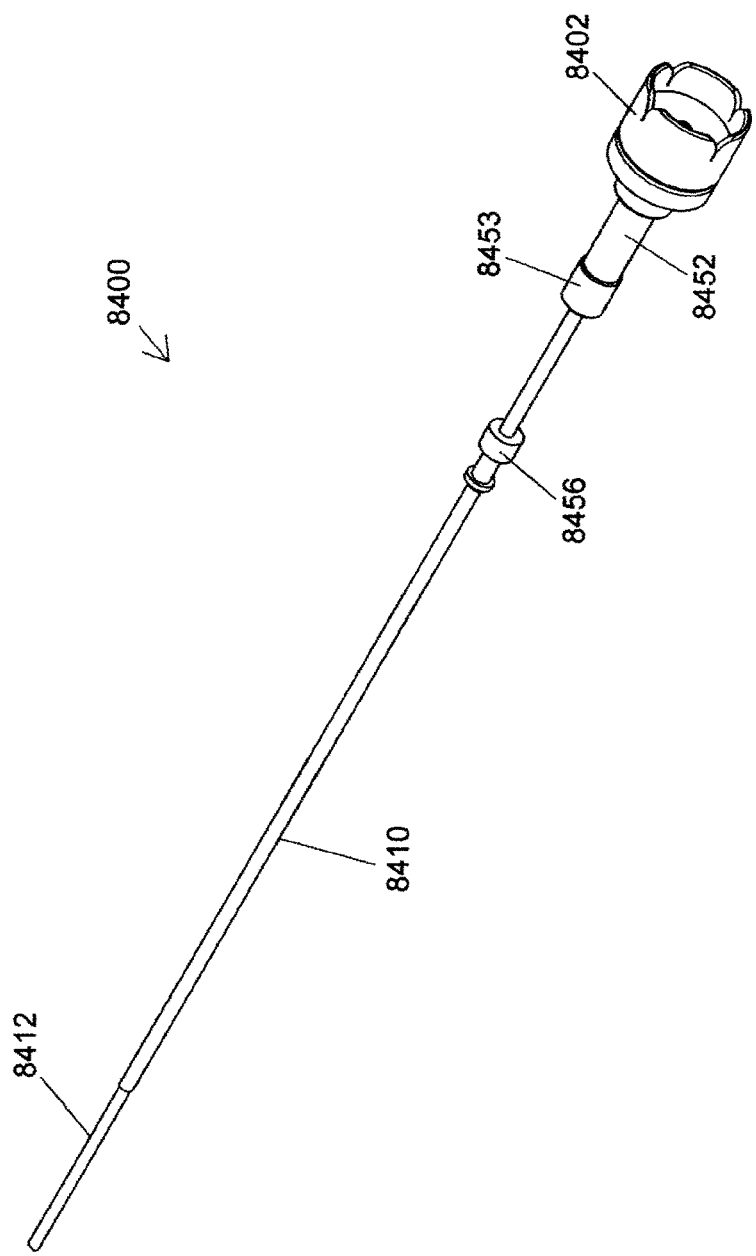

FIG. 127 is a perspective view of a inner tensioning assembly suitable for use in an alternate embodiment of an implant placement system of the present invention.

Figure 128:
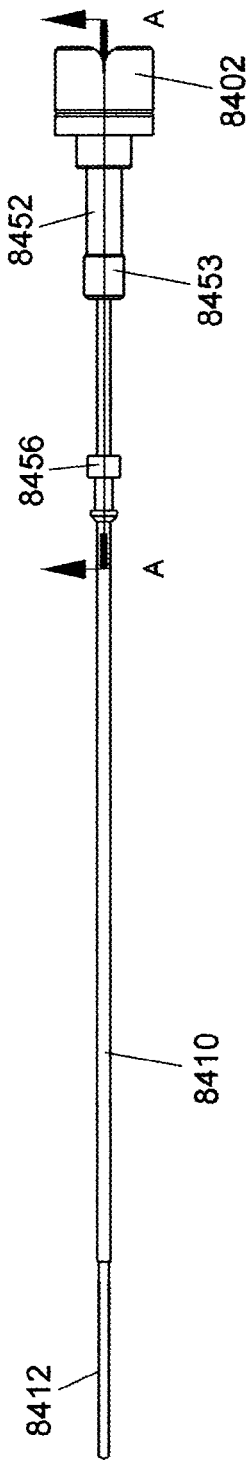

FIG. 128 is a plan view of the objects of FIG. 127.

Figure 129:
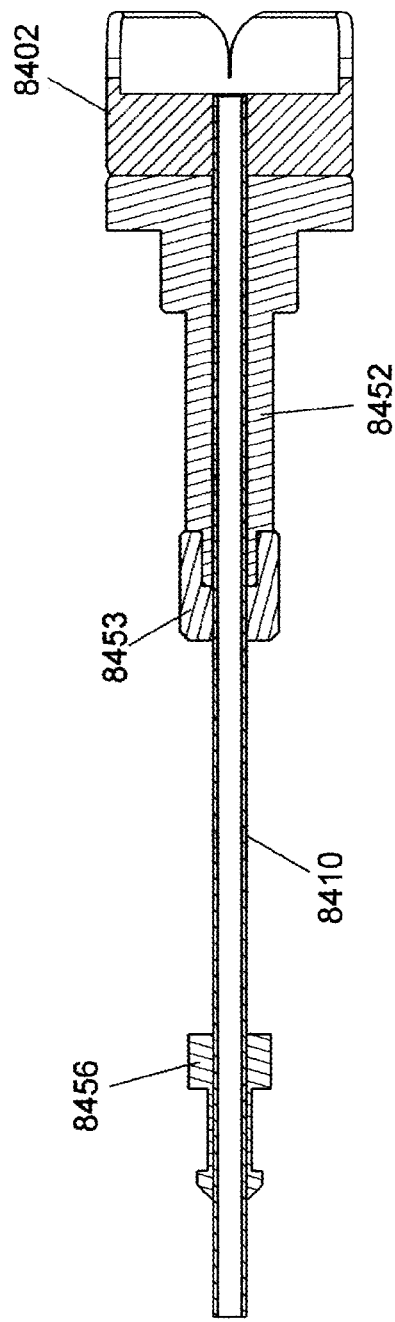

FIG. 129 is an expanded sectional view of the objects of FIG. 128 at location A-A.

Figure 130:
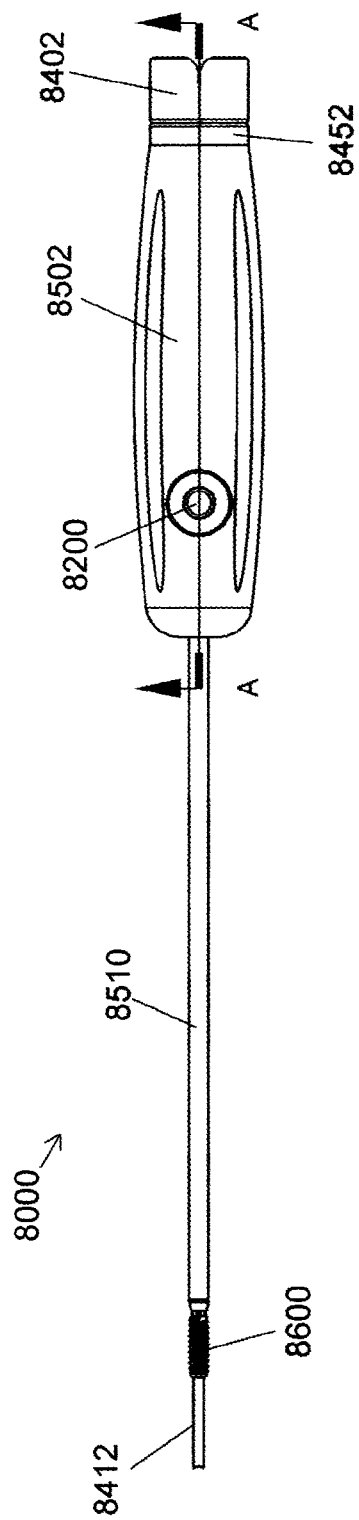

FIG. 130 is a plan view of an alternate embodiment of an implant placement system of the present invention that incorporates the inner tensioning assembly of FIG. 127 and with the outer driver assembly in its proximal position.

Figure 131:
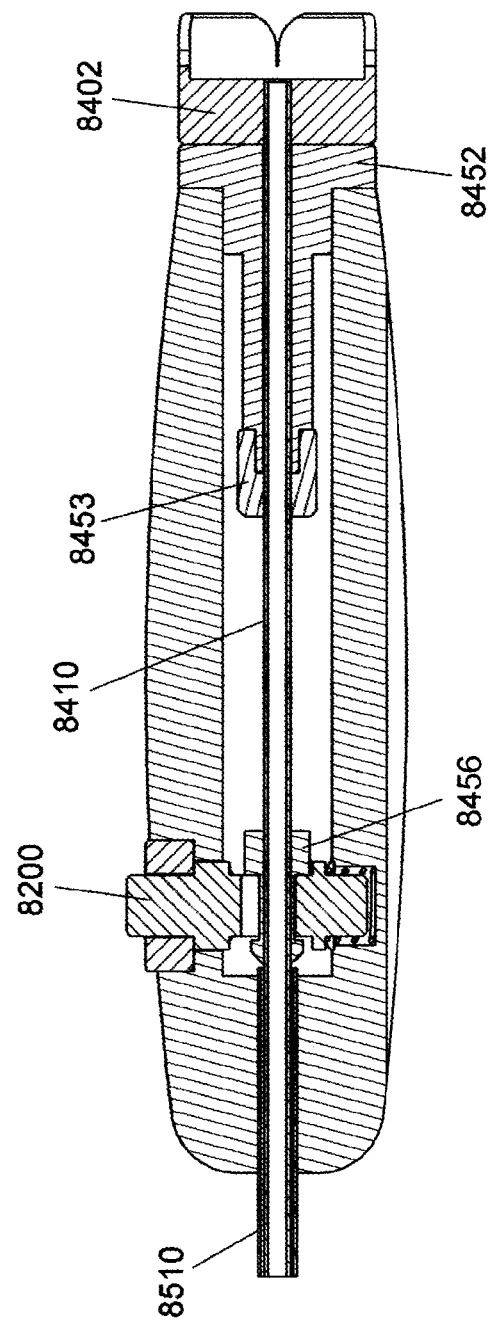

FIG. 131 is an expanded sectional view of the objects of FIG. 130 at location A-A.

FIG. 132 is a plan view of the implant placement system of FIG. 130 with the outer driver assembly in its distal position.

FIG. 133 is an expanded sectional view of the objects of FIG. 132 at location A-A.

FIG. 134 is a perspective view of the inner assembly for an alternate embodiment of an implant placement system in accordance with the present invention.

FIG. 135 is an expanded view of the objects of FIG. 134 at location A.

Figure 136:
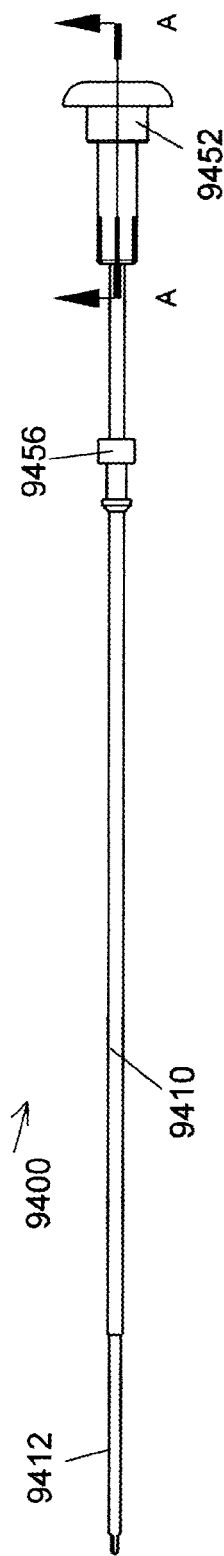

FIG. 136 is a plan view of the objects of FIG. 134.

Figure 137:
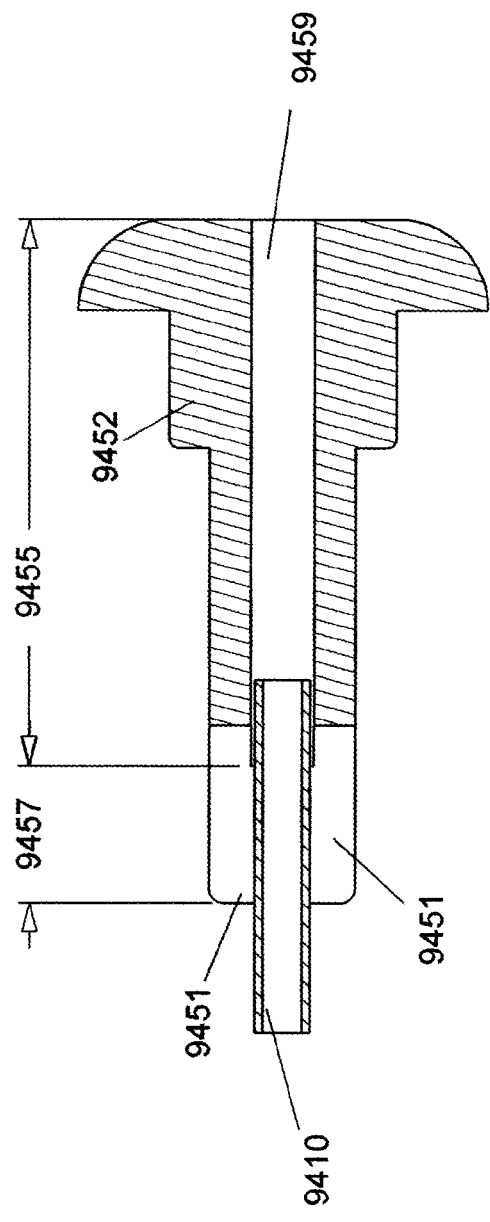

FIG. 137 is an expanded sectional view of the objects of FIG. 136 at location A-A.

Figure 138:
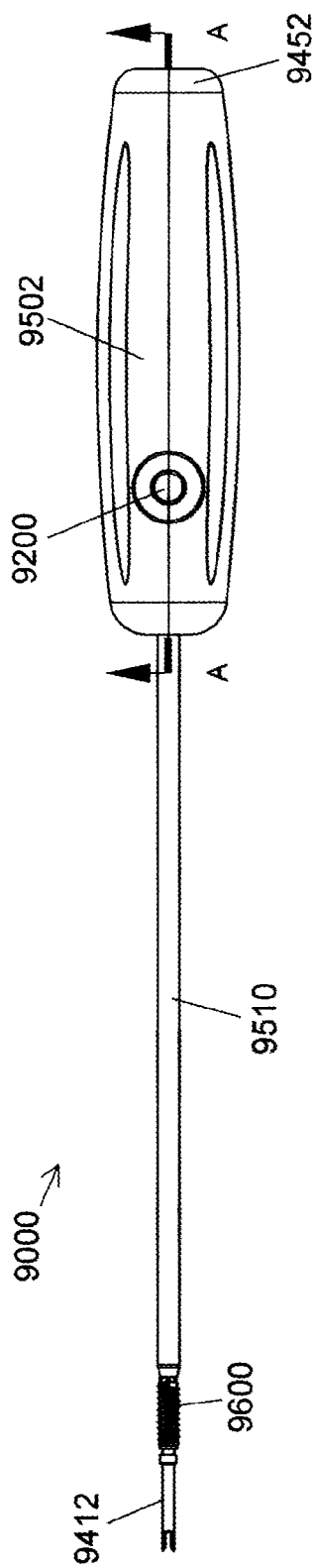

FIG. 138 is a plan view of an alternate embodiment of an implant placement system of the present invention that incorporates the inner assembly of FIG. 134.

Figure 139:
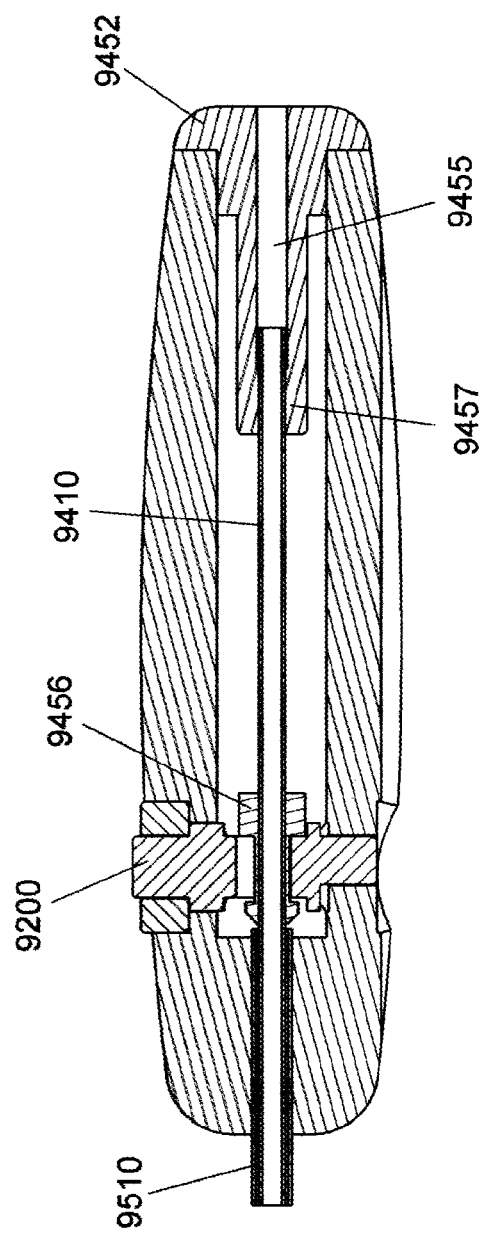

FIG. 139 is an expanded sectional view of the objects of FIG. 138 at location A-A.

Figure 140:
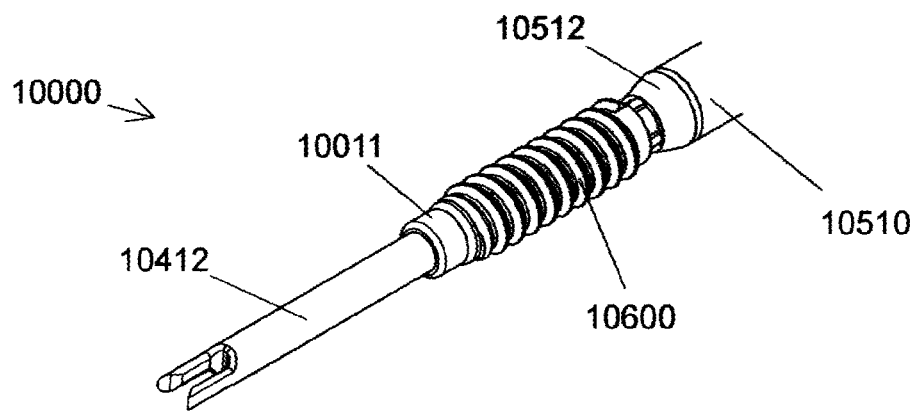

FIG. 140 is a perspective view of the distal portion of an alternate embodiment of an implant placement system in accordance with the present invention.

Figure 141:
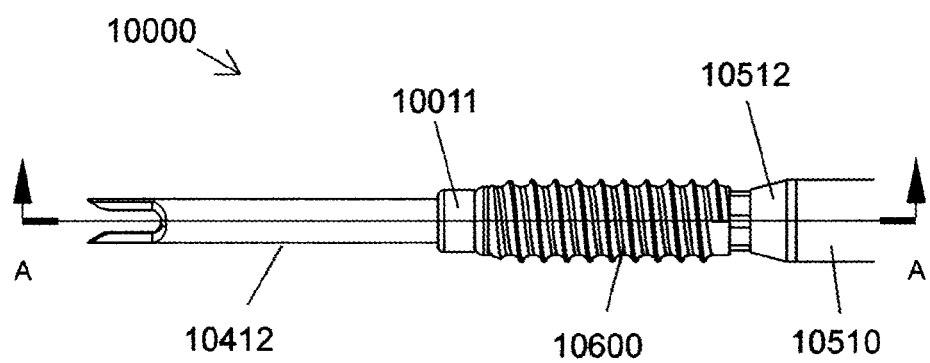

FIG. 141 is a plan view of the objects of FIG. 140.

Figure 142:
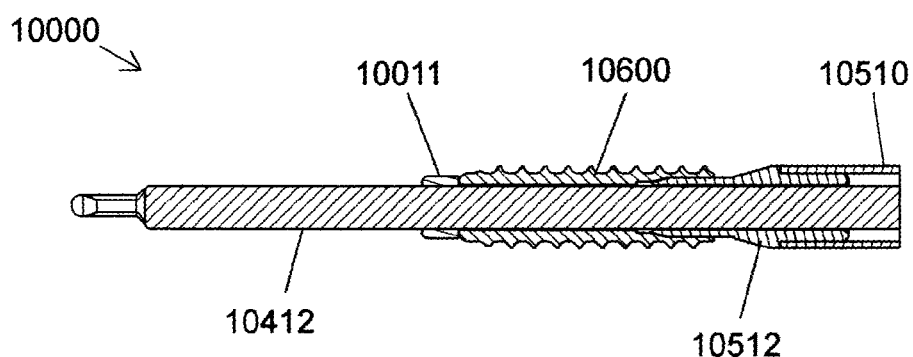

FIG. 142 is a sectional view of the objects of FIG. 140 at location A-A.

Figure 143:
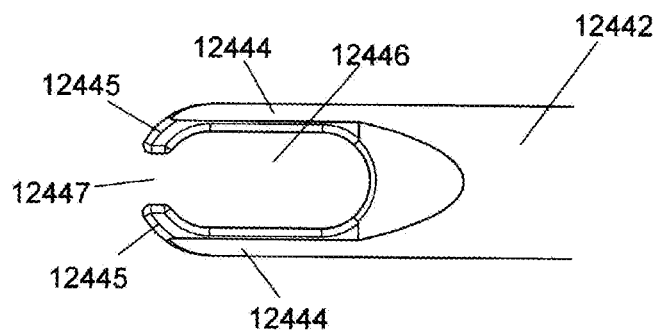

FIG. 143 is an expanded plan view of a modified distal end of a tensioning device for use in an alternate embodiment of an implant placement system in accordance with the present invention.

Figure 144:
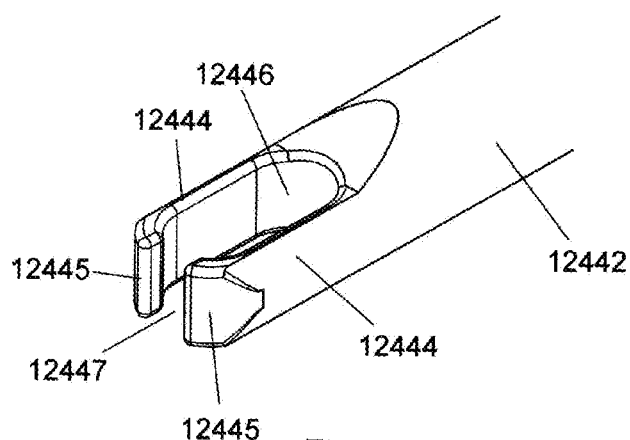

FIG. 144 is a distal perspective view of the objects of FIG. 143.

Figure 145:
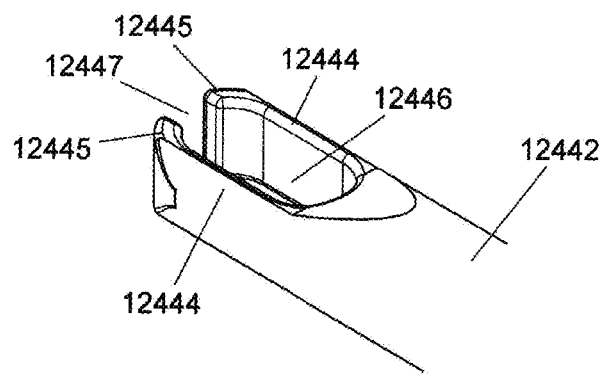

FIG. 145 is a proximal perspective view of the objects of FIG. 143.

Figure 146:
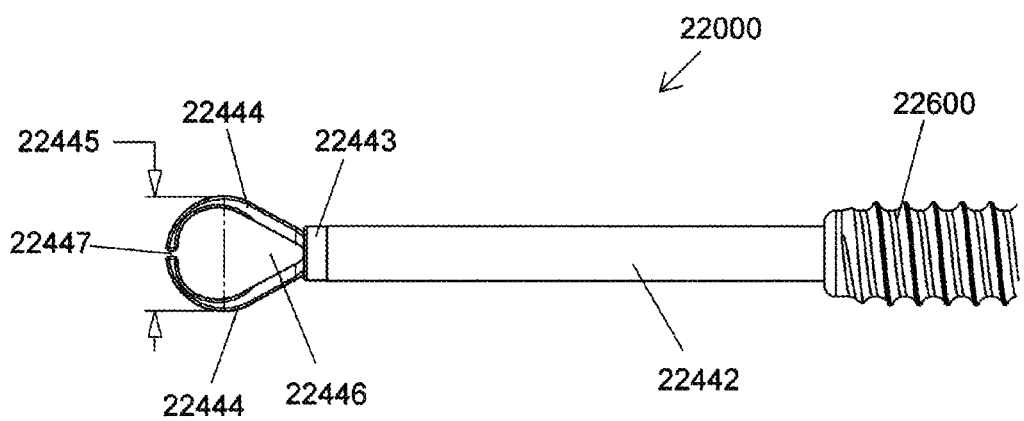

FIG. 146 is an expanded plan view of the distal end of an alternate embodiment of an implant placement system of the present invention.

Figure 147:
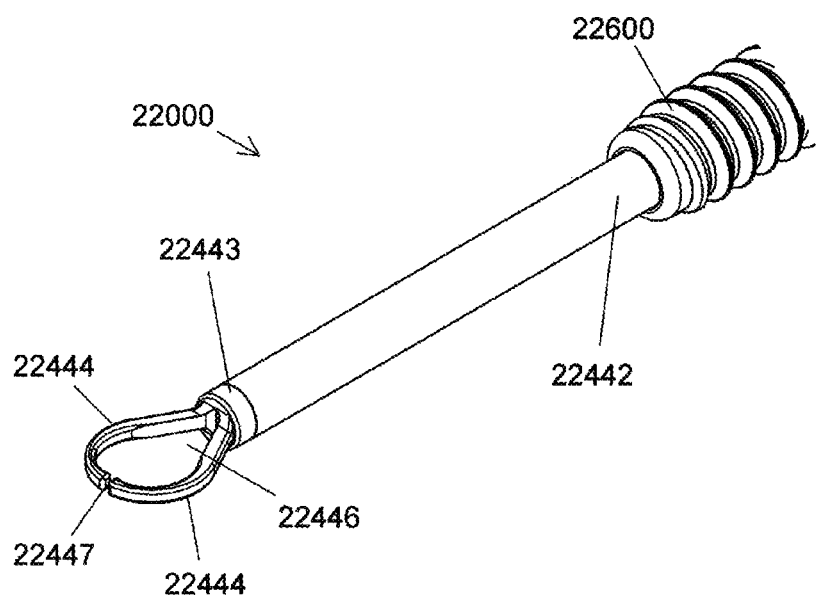

FIG. 147 is a perspective view of the objects of FIG. 146.

Figure 148:
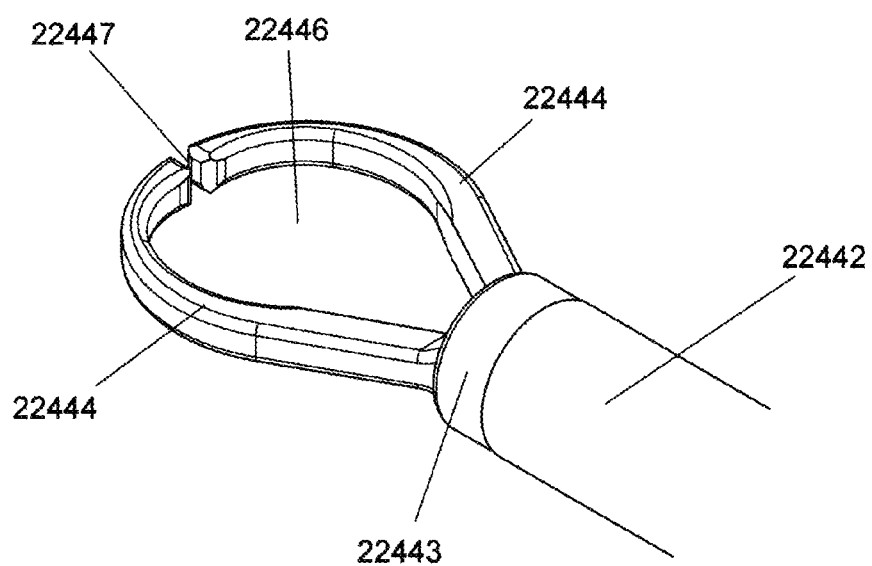

FIG. 148 is an expanded perspective view of the objects of FIG. 146.

Figure 149:
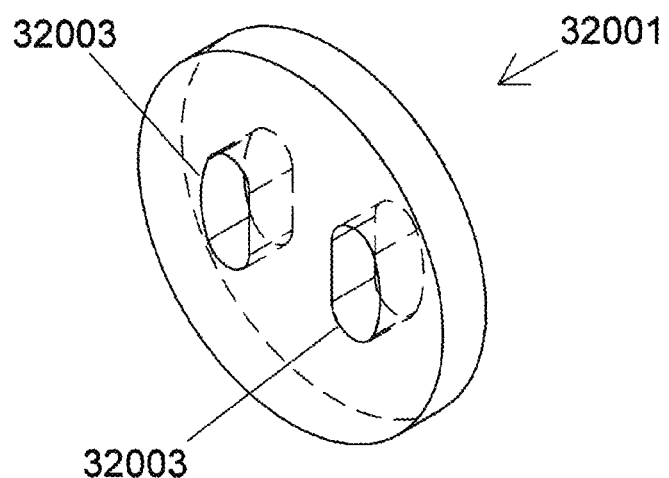

FIG. 149 is a perspective view of a penetration-limiting element for use in an alternate embodiment of an implant placement system of the present embodiment.

Figure 150:
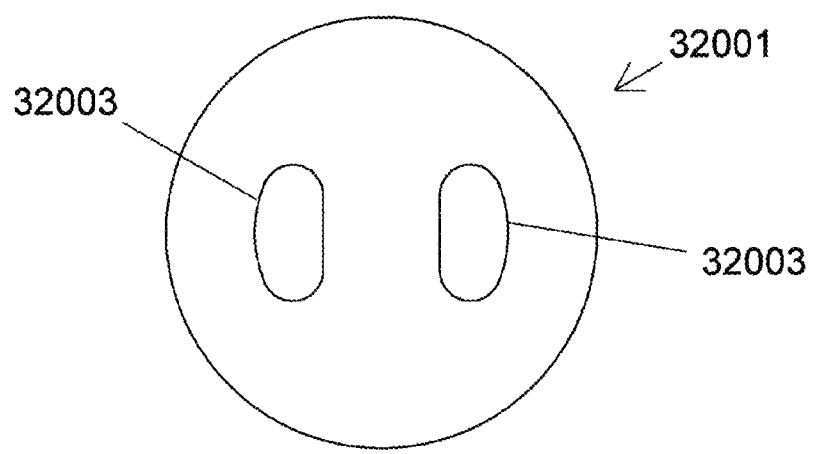

FIG. 150 is a side elevational view of the objects of FIG. 149.

Figure 151:
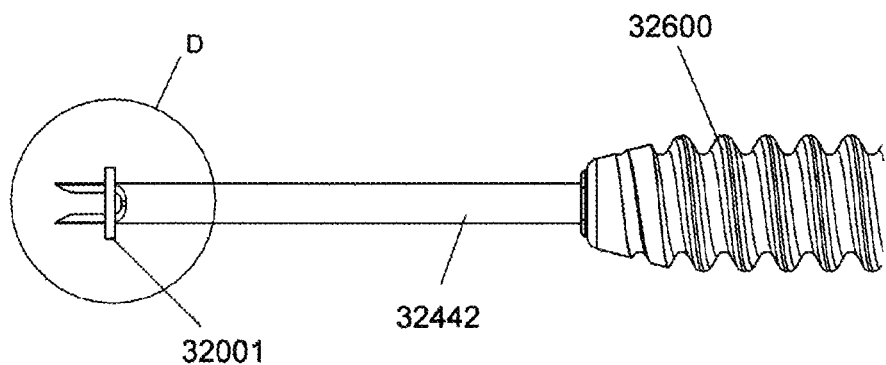

FIG. 151 is an expanded plan view of an alternate embodiment of an implant placement system of the present invention incorporating the penetration-limiting element of FIG. 149.

Figure 152:
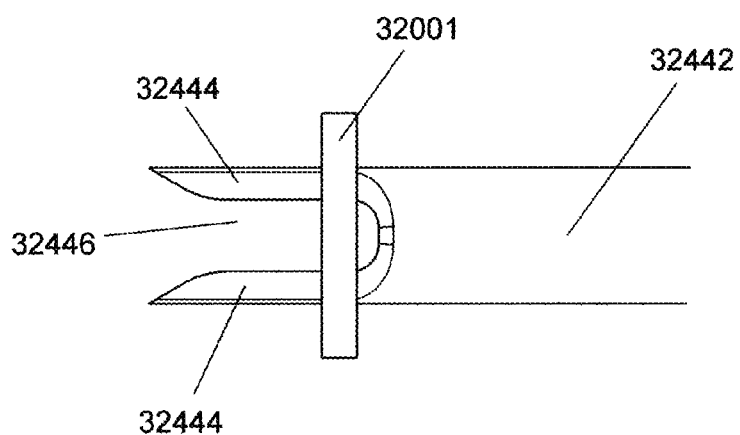

FIG. 152 is an expanded view of the objects of FIG. 151 at location D.

Figure 153:
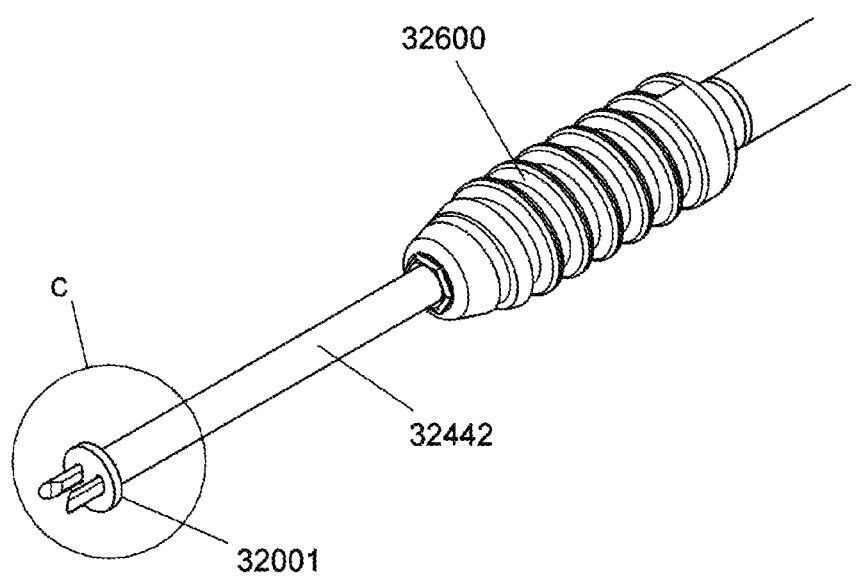

FIG. 153 is a perspective view of the objects of FIG. 151.

Figure 154:
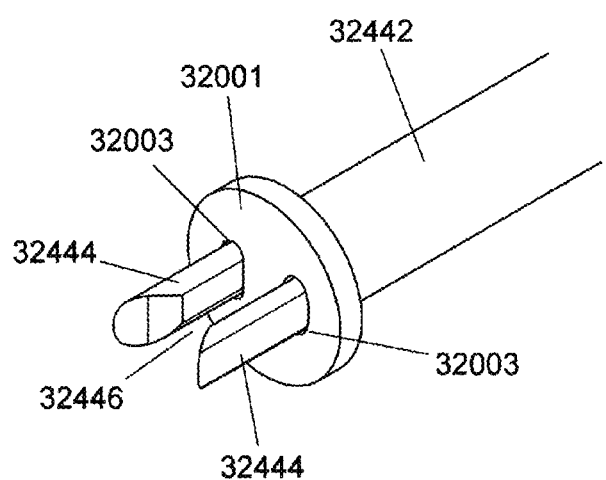

FIG. 154 is an expanded view of the objects of FIG. 153 at location C.

Figure 155:
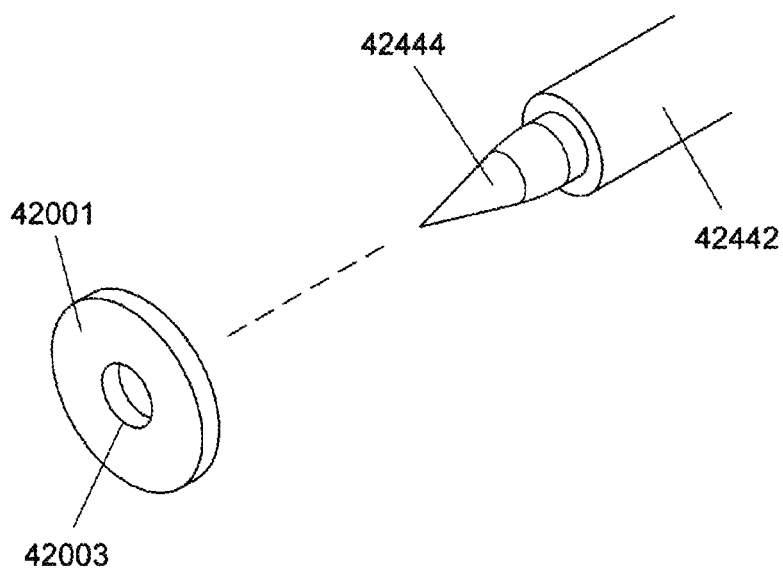

FIG. 155 is a perspective view of the distal portion of an alternate embodiment of an implant placement system of the present invention that depicts a penetration or depth-limiting element positioned for mounting to the distal end of a distal element.

Figure 156:
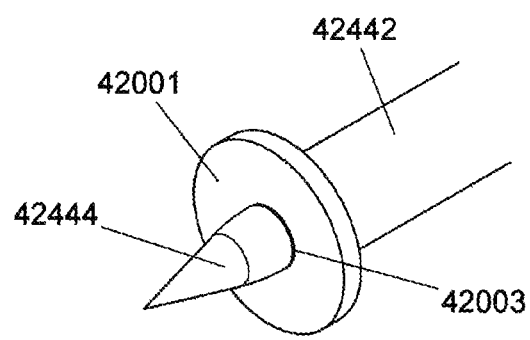

FIG. 156 is a perspective view of the elements of FIG. 155 assembled in preparation for use.

Figure 157:
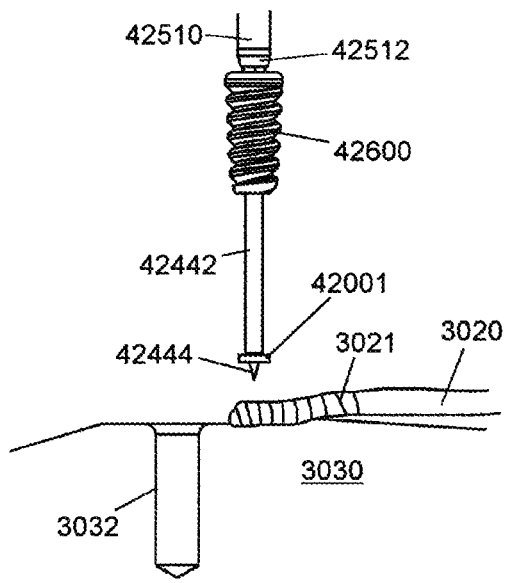

FIG. 157 depicts a first step in a procedure for reattachment of a tendon to a boney surface using the components depicted in FIGS. 155 and 156.

Figure 158:
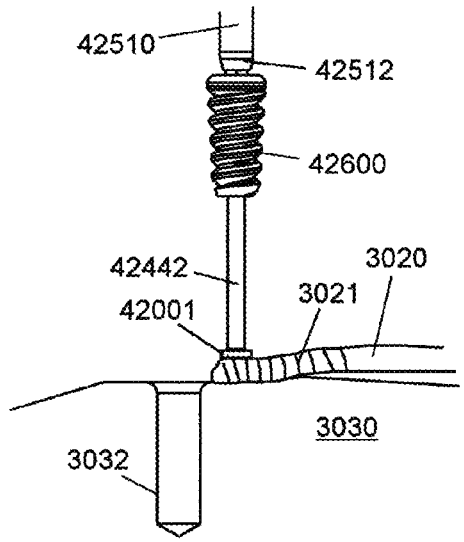

FIG. 158 depicts a second step in the procedure of FIG. 157.

Figure 159:
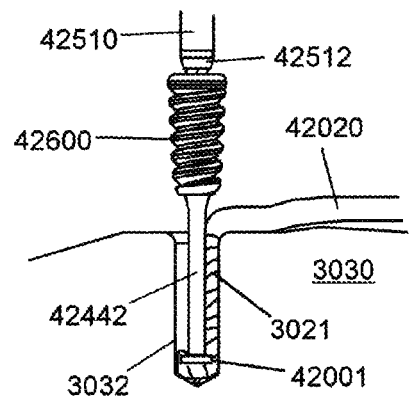

FIG. 159 depicts a third step in the procedure of FIG. 157.

Figure 160:
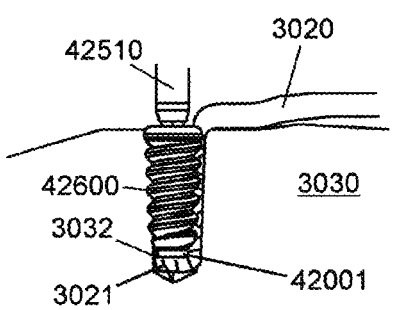

FIG. 160 depicts a fourth step in the procedure of FIG. 157.

Figure 161:
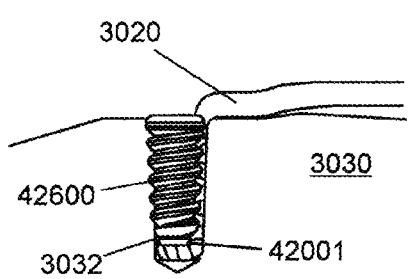

FIG. 161 depicts the surgical site at the completion of reattachment of a graft to a boney surface using the procedure the beginning of which is depicted in FIG. 157.

Figure 162:
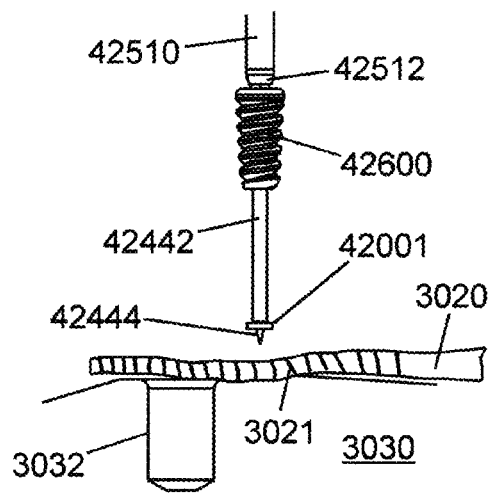

FIG. 162 depicts a first step in an alternate procedure for reattachment of a tendon to a boney surface using the components depicted in FIGS. 155 and 156.

Figure 163:
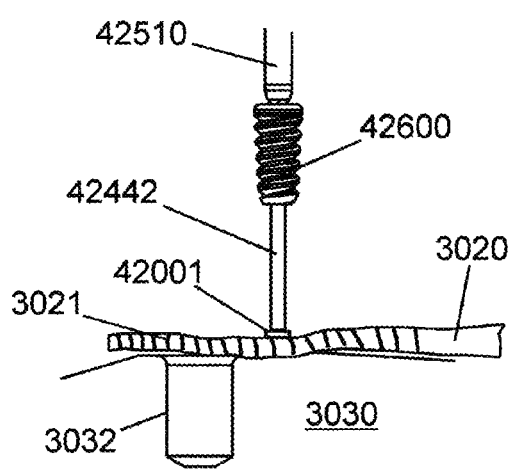

FIG. 163 depicts a second step in the procedure of FIG. 162.

Figure 164:
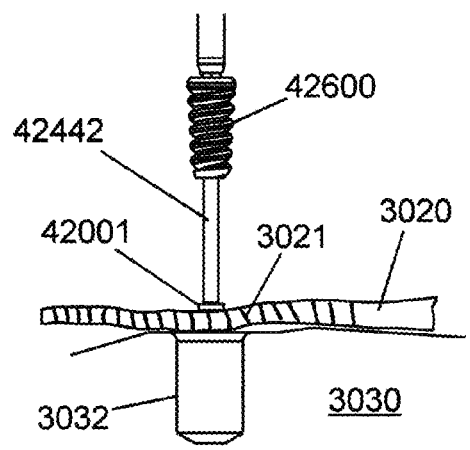

FIG. 164 depicts a third step in the procedure of FIG. 162.

Figure 165:
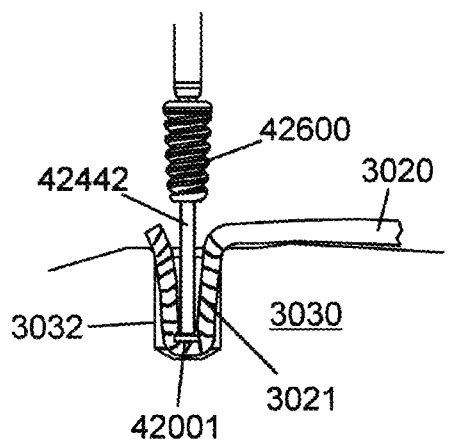

FIG. 165 depicts a fourth step in the procedure of FIG. 162.

Figure 166:
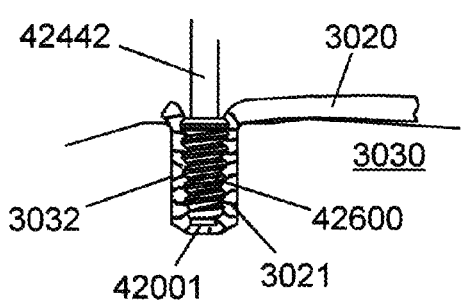

FIG. 166 depicts a fifth step in the procedure of FIG. 162.

Figure 167:
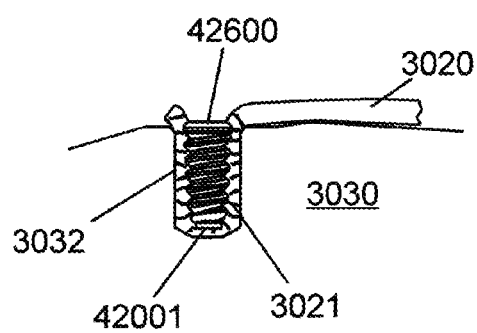

FIG. 167 depicts the surgical site at the completion of the procedure of FIG. 162.

FIG. 168 is an expanded plan view of the distal end of an alternate embodiment of an implant placement system of the present invention that includes a resilient distal element.

FIG. 169 is an expanded view of the objects of FIG. 168 at location B.

Figure 170:
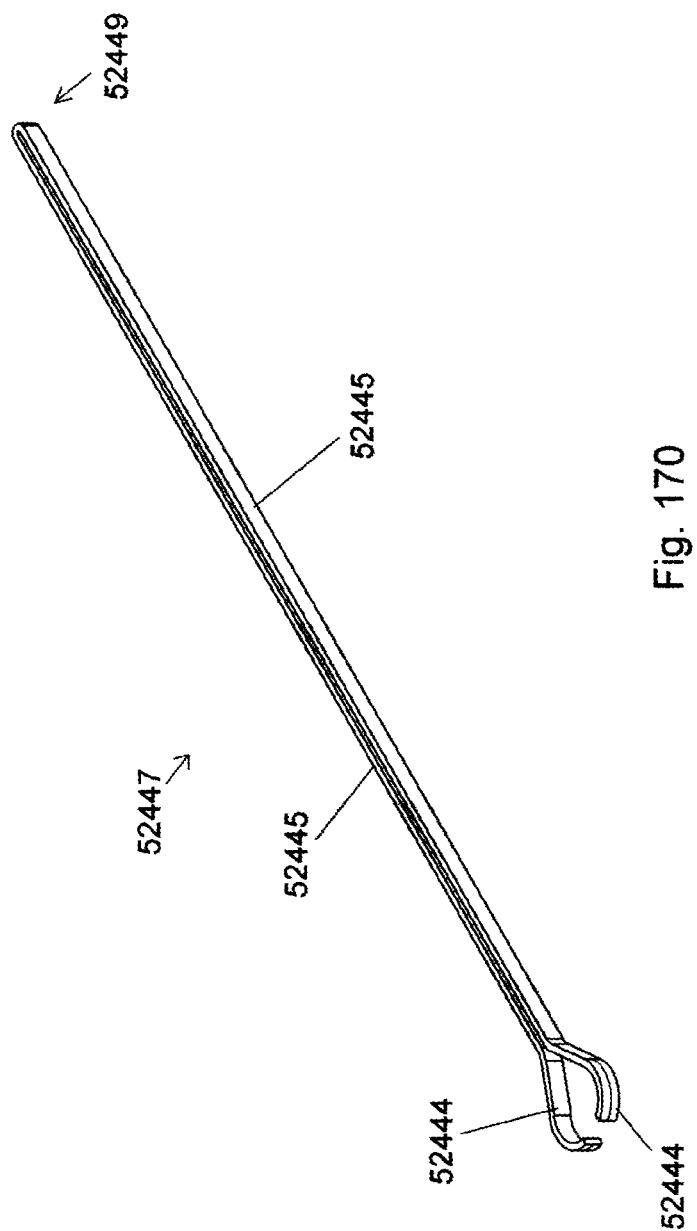

FIG. 170 is a perspective view of the resilient distal element of FIG. 168.

Figure 171:
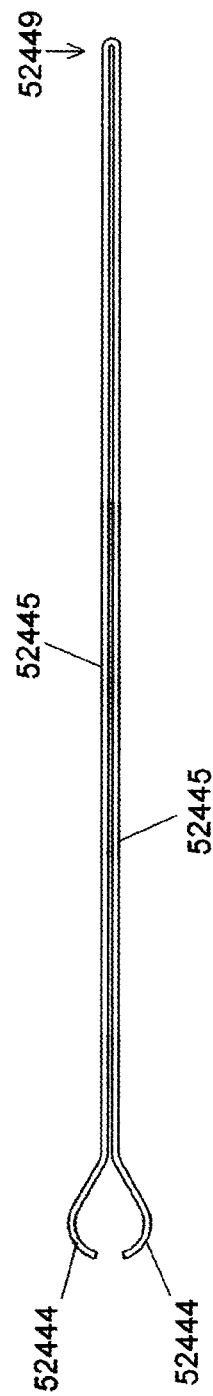

FIG. 171 is a plan view of the resilient distal element of FIG. 169.

DETAILED DESCRIPTION OF THE PREFERRED EMBODIMENTS

Aspects of the present invention relate to, coordinate with, and/or overlap with aspects described by the present inventors in their previous patent filings. For example, aspects of the present invention are compatible with and thus may be combined with the ceramic implant placement systems and superelastic suture retention loops described in U.S. Pat. No. 9,770,240 issued Sep. 26, 2017. Likewise, aspects of the present invention are suitable for use in the context of the multiple implant construction and fixation methods described in U.S. Pat. No. 9,717,587 issued Aug. 1, 2017 and U.S. Pat. No. 9,999,496 issued Jul. 19, 2018. The present invention is further compatible with and thus may include the split loop constructions described in U.S. Pat. No. 9,907,548 issued Mar. 6, 2018. As such, these preceding disclosures are hereby incorporated by reference herein in their entirety.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

In the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion which is situated closest to the user of the device, farthest away from the target surgical site. In the context of the present invention, the proximal end of the implant system of the present invention includes the driver and handle portions.

The term "distal" as used herein refers to that end or portion situated farthest away from the user of the device, closest to the target surgical site. In the context of the present invention, the distal end of the implant systems of the present invention includes components adapted to fit within the pre-formed implant-receiving socket.

In the context of the present invention, the terms "cannula" and "cannulated" are used to generically refer to the family of rigid or flexible, typically elongate, lumened surgical instruments that facilitate access across tissue to an internally located surgery site.

The terms "tube" and "tubular" are interchangeably used herein to refer to a generally round, long, hollow component having at least one central opening often referred to as a "lumen".

The terms "lengthwise" and "axial" are used interchangeably herein to refer to the direction relating to or parallel with the longitudinal axis of a device. The term "transverse" as used herein refers to the direction lying or extending across or perpendicular to the longitudinal axis of a device.

The term "lateral" pertains to the side and, as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

As discussed above, when a tissue, more particularly a soft connective tissue in a joint space, becomes damaged or torn from its associated bone or cartilage, surgery is usually required to reattach the tissue or reconstruct the bone. The present invention is directed to various means and mechanisms for securing the displaced tissue to boney tissue.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. While the present invention is not restricted to any particular soft tissue, aspects of the present invention find particular utility in the repair of connective tissues such as ligaments or tendons, particularly those of the shoulder, elbow, knee or ankle joint.

In a similar fashion, while the present invention is not restricted to any particular boney tissue, a term used herein to refer to both bones and cartilage, aspects of the present invention find particular utility in the repair or reattachment of connective tissues to the boney elements of the shoulder, elbow, wrist, hand, hip, knee or ankle joint.

When the damaged tissue is of sufficient quantity and quality, the damaged portion may simply be directly reattached to the bone from which it was torn so that healing back to the bone can take place. However, in other situations, a "graft" may be needed to stimulate regrowth and permanent attachment. In the context of the present invention, the term "graft" refers to any biological or artificial tissue being attached to the boney tissue of interest, including:

Autografts, i.e., grafts taken from one part of the body of an individual and transplanted onto another site in the same individual, e.g., ligament graft;

Isografts, i.e., grafts taken from one individual and placed on another individual of the same genetic constitution, e.g., grafts between identical twins;

Allografts, i.e., grafts taken from one individual placed on genetically non-identical member of the same species; and Xenografts, i.e., grafts taken from one individual placed on an individual belonging to another species, e.g., animal to man.

Autografts and isografts are usually not considered as foreign and, therefore, do not elicit rejection. Allografts and xenografts are recognized as foreign by the recipient thus carry a high risk of rejection. For this reason, autographs and isografts are most preferred in the context of the present invention.

Surgical interventions such as contemplated herein generally require the boney tissue to be prepared for receiving the graft. In the context of the present invention, such preparation includes the formation of a "socket", i.e., a hole punched or drilled into the bone into which a prosthetic device such as an implant may be received. The socket may be prepared at the desired target location using conventional instruments such as drills, taps, punches or equivalent hole-producing devices. In other embodiments the socket may be formed at the time of implant placement using a sharpened distal portion that is integral with the implant placement system and that protrudes beyond the distal end of the implant.

While certain procedures contemplate directly attaching the graft to the bone, the more common route involves the employment of an implant specially configured to hold and/or enable attachment of the graft to the boney tissue. As used herein, the term "implant" refer to a prosthetic device fabricated from a biocompatible and/or inert material. In the context of the present invention, examples of such "implants" include conventional and knotless anchors of both the screw-threaded and interference-fit variety, as well as interference screws.

In certain embodiments, the present invention contemplates fabrication of the implant from either a metallic material or a suitable polymeric material, including, but not limited to, polyetheretherketone (PEEK), a polymeric composite such as, for instance, carbon fiber reinforced PEEK (PEEK CF), or of a suitable bioabsorbable material such as, for instance, polylactic acid (PLA). The present invention also contemplates the use of very small knotless anchors produced from ceramic materials using a process known as "Ceramic Injection Molding" or simply "CIM". The tensile strength of PEEK material is typically between 10,000 and 15,000 psi. In comparison, the tensile strength of alumina is generally in excess of 200,000 psi. Furthermore, recently developed materials such as Zirconia Toughened Alumina (ZTA) by Coorstek Inc. (Golden, Colo.) have a high degree of toughness in addition to high tensile strength. These materials, being ceramic, do not have a yield point and therefore do not deform under load. The high tensile strength and the absence of yielding under load of an implant constructed of such ceramic materials allow torque to be transmitted to the implant through features that are not producible by the machining of metal or that would fail in use if formed from a polymeric material such as PEEK.

In certain embodiments, the implant may take the form of a ceramic interference plug, wherein the high elastic modulus and high strength of the ceramic materials is beneficial for small and miniature interference type anchors that are driven axially into a prepared socket. The high modulus and high strength of the materials allows the thickness of the wall between the central lumen and the outer surface to be reduced compared to interference type anchors produced from polymeric materials without reducing the compressive force which retains the one or more sutures between the outer wall of the implant and the wall of the socket.

A preferred implant system of the present invention is comprised of an optionally cannulated tensioning device (also referred to as the "inserter" or "insertion device") slidably received within the lumen of a cannulated driver device (also referred to as the implant driver or simply "driver") that together serve to tension sutures in a prepared socket for the placement of a simple, one-piece, cannulated anchor. In the Examples below, the present invention makes reference to various lock-and-key type mating mechanisms that serve to establish and secure the axial and rotational arrangement of these device components. However, it will again be readily understood by the skilled artisan that the position of the respective coordinating elements (e.g., recessed slots and grooves that mate with assorted projecting protrusions, protuberances, tabs and splines) may be exchanged and/or reversed as needed.

In the context of the present invention, a preferred implant placement system of the present invention includes an optionally cannulated tensioning assembly (also referred to as the "inserter" or "insertion assembly") slidably received within the lumen of a cannulated driver device (also referred to as the "driver") that together serve to tension sutures in a prepared socket for the placement of a simple one-piece cannulated anchor. The implant placement system of the present invention requires a robust connection between the "driver device" and the associated "implant" or "anchor" so as to ensure that the two rotate as a single unit such that rotational force or "torque" applied to the proximal end of the system (e.g., via the proximal handle portion of the driver device) is transmitted to the distal end of the system (e.g., the distal end of the implant disposed in the prepared socket) without incident or interruption. This continuous "torque transfer" along the length of the system, from proximal to distal end, is critical to the function of the driver, enabling it to distally advance the implant and firmly secure the implant (and any associated sutures or tissues) in the biological site of interest. In the context of the present invention, this continuous torque transfer is achieved by means of coordinating "torque-transmitting" elements, namely a distal "torque-transmitting portion" of the driver device that is configured to mate with and/or conform to a "torque-transmitting" (or alternatively "torque-receiving" or "torque-transferring") portion of the implant, such "portion" including at a minimum the proximal end of the implant though the present invention contemplates embodiments where "torque-transmitting" features on the implant extend along the length of the implant. The respective "torque-transmitting" features on the driver device and implant cooperate to ensure that any proximal torque applied by the user to the proximal handle portion of the device is directly conveyed ("transmitted") to the distal end of the implant.

In certain embodiments, the torque-transmitting portion of the implant may take the form of a laterally extending slot in the proximal end of the implant similar to a standard screwdriver slot; however, other geometries are contemplated and described in detail herein as well as in disclosures incorporated by reference herein. In addition, like the implant itself, the distal torque-transmitting portion of the driver may also be fabricated from a ceramic material and formed by ceramic injection molding so as to allow miniaturization of the torque-transmitting features.

The present invention makes reference to insertion devices commonly referred to in the art as "drills" and "drivers", i.e., devices that "drill" the socket and "drive" the implant into the socket. In the context of the present invention, the drills and drivers may be conventional, e.g., rigidly linear as previously herein described, or, as discussed in detail herein, "off-axis", e.g., having an angularly offset distal portion adapted to drill off-axis sockets in boney tissues that are remote and difficult to access and drive therein the corresponding implant, such as an anchor or interference screw.

In certain embodiments, the present invention contemplates securing the graft to the implant via sutures. In the context of the present invention, the term "suture" refers to a thread-like strand or fiber used to hold body tissues after surgery. Sutures of different shapes, sizes, and thread materials are known in the art and the present invention is not restricted to any particular suture type. Accordingly, in the context of the present invention, the suture may be natural or synthetic, monofilament or multifilament, braided or woven, permanent or resorbable, without departing from the spirit of the invention.

In certain embodiments, the present invention makes reference to an elongate element of a superelastic and/or shape memory material configured to include a suture retention loop at its distal end and designed to be slidably received within a lumen of a cannulated tensioning device or inserter. In certain preferred examples, the elongate element takes the form of a "nitinol wire". In the context of the present invention, "nitinol" is a super elastic metal alloy of nickel and titanium. In a preferred embodiment, the two elements are present in roughly equal atomic percentage (e.g., Nitinol 55, Nitinol 60). Nitinol alloys exhibit two closely related and unique properties: shape memory effect (SME) and superelasticity (SE; also called pseudoelasticity, PE). Shape memory is the ability of nitinol to undergo deformation at one temperature, then recover its original, undeformed shape upon heating above its "transformation temperature". Superelasticity occurs at a narrow temperature range just above its transformation temperature; in this case, no heating is necessary to cause the undeformed shape to recover, and the material exhibits enormous elasticity, some 10-30 times that of ordinary metal.

The present invention also makes reference to high strength polymeric materials and high tensile strength ceramic materials, such as alumina or zirconia, that may be formed to complex shapes by a process referred to as Ceramic Injection Molding (CIM). In this process, ceramic powder and a binder material are molded to a shape that is subsequently fired in a furnace to eliminate the binder material and sinter the ceramic powder. During this sintering operation the item is reduced in size by twenty to thirty percent and achieves near 100% density with very high dimensional repeatability. Ceramic materials that are routinely molded and thus contemplated by the present invention include, but are not limited to, alumina, zirconia toughened alumina (ZTA) partially stabilized zirconia (PSZ) and silicon nitride ($Si_3N_4$). The flexular strengths of these materials range from 55,000 psi to 250,000 psi, far higher than the 25,000 psi flexular strength of implantable PEEK material.

The present invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal, more preferably a human.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

EXAMPLES

The present invention attempts to address these aforenoted problems in the art. To that end, FIGS. 1A through 1C and 2A and 2B depict a cannulated driver 1500 for a knotless anchor placement system of the present invention. Driver 1500 has a proximal handle 1502 in which is formed a proximal cylindrical recess 1504, and off-axis lateral holes 1506, and a tubular distal portion 1510 having at its distal end tubular drive element 1512. The distal portion 1514 of drive element 1512 is configured to be complementary to internal drive features 1602 in the proximal portion of the lumen of cannulated threaded anchor 1600; accordingly, torque supplied by driver 1500 is transmitted to anchor 1600. The distal portion of drive element 1512 may be fabricated in a variety of sizes, shapes, configurations and lumen sizes to suit a variety of anchors 1600, the requirements for a particular anchor 1600 depending on its size, configuration and material properties. For example, the complementary drive elements may take the form of an internally or externally positioned hexagonal or square drive, an internal or external spline, or slots positioned internal or external to the anchor. However, the present invention contemplates alternate cooperating configurations and thus is not limited to any one particular embodiment.

Referring now to FIGS. 3 through 9, cannulated tensioning device 1400 has a proximal hub 1402 with a distal cylindrical portion 1404 in which are formed off-axis lateral grooves 1406, and cleats 1408 formed in the proximal rim of proximal hub 1402. Tensioning device 1400 has a tubular middle portion 1410, and a tubular distal portion 1412, distal portion 1412 having a diameter 1414 and length 1416. Diameter 1414 is selected such that distal portion 1412 may be slidably positioned within distal drive element 1512 of cannulated driver 1500. Length 1416 is determined such that when tensioning device 1400 is positioned within the lumen of the cannulated driver 1500, distal portion 1412 of tensioning device 1400 protrudes beyond distal drive element 1512 of driver 1500 a sufficient distance so that when anchor 1600 is mounted on distal drive element 1512 and distal portion 1412 is inserted to the full depth of a suitable socket formed in bone, anchor 1600 is still proximal to and clear of the socket. Elongate wire element 1302 having at its distal end loop 1304 and at its proximal end polymeric element 1306 forming a pull tab forms a loading loop 1300 for drawing sutures into the lumens of tubular members 1410 and 1412.

Figure 1A:
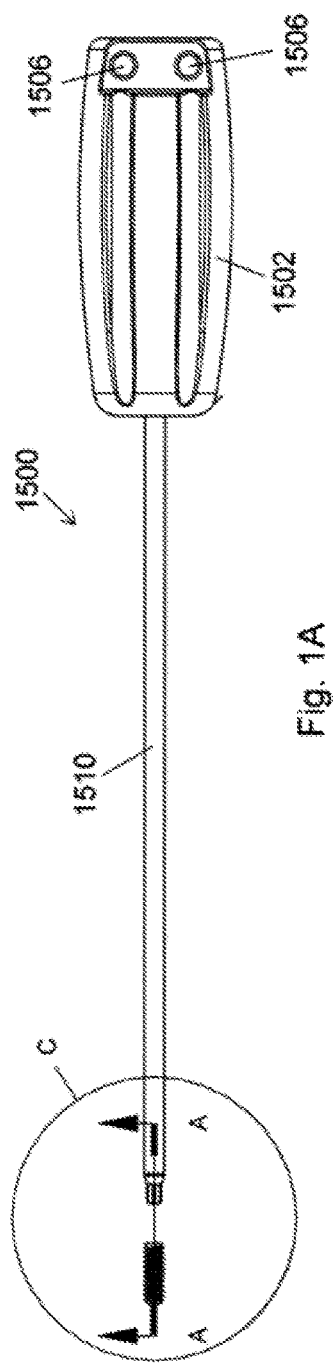
FIG. 1A is a plan view of a cannulated driver and anchor illustrative of an implant placement system of the present invention.
Figure 1B:
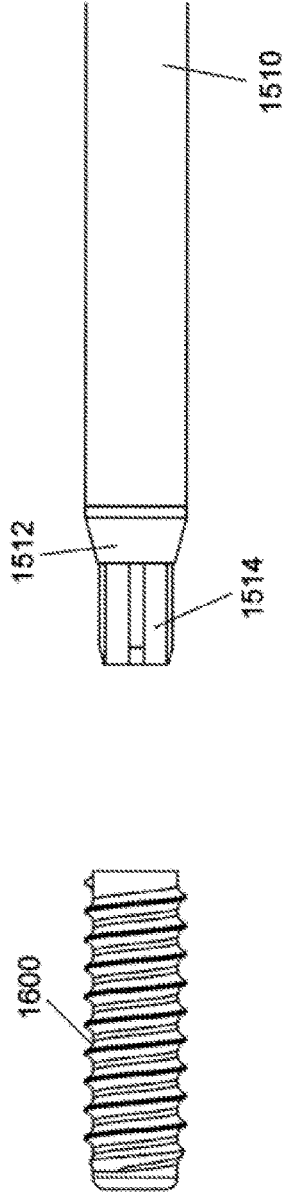
FIG. 1B is an expanded view of the distal portion of the objects of FIG. 1A at location C.
Figure 1C:
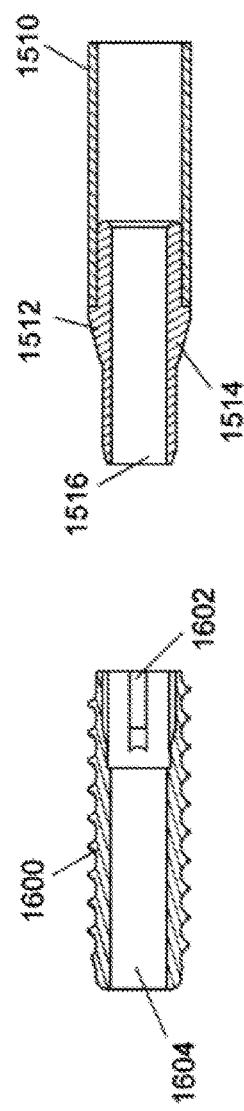
FIG. 1C is a side elevational sectional view of the objects of FIG. 1A at location A-A of FIG. 1A.
Figure 2A:
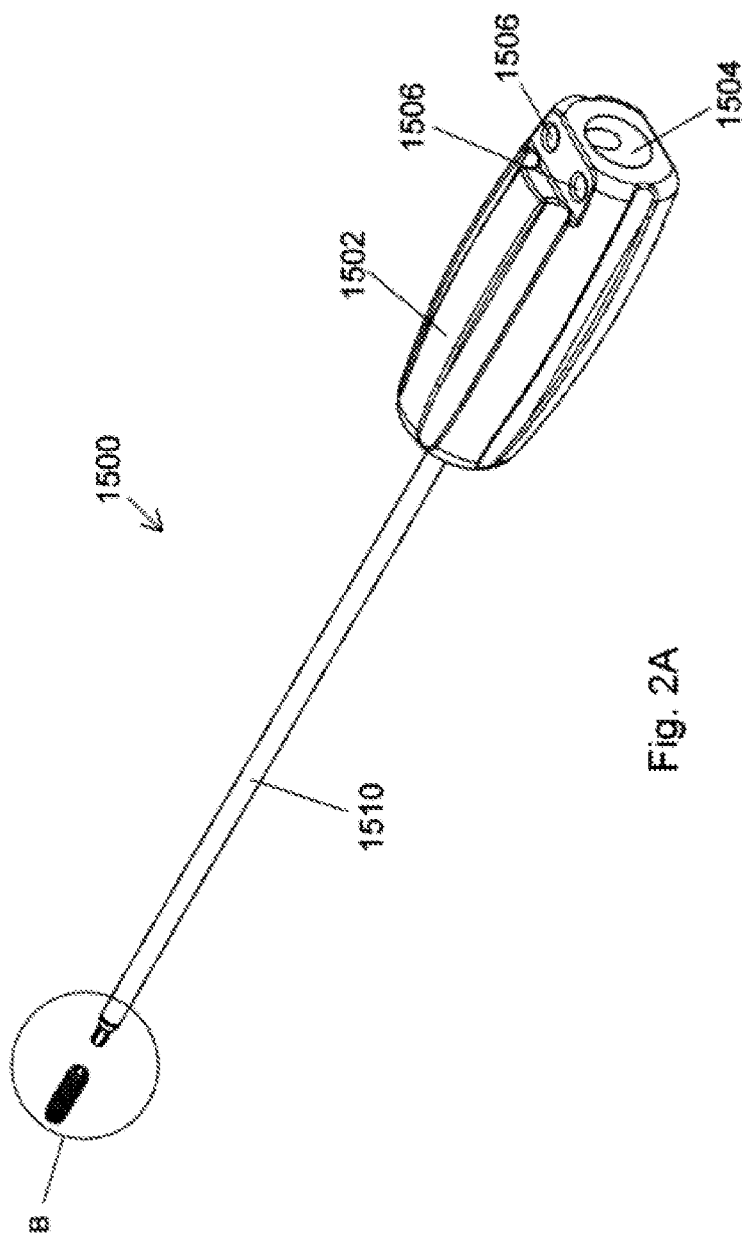
FIG. 2A is a perspective view of the objects of FIG. 1A.
Figure 2B:
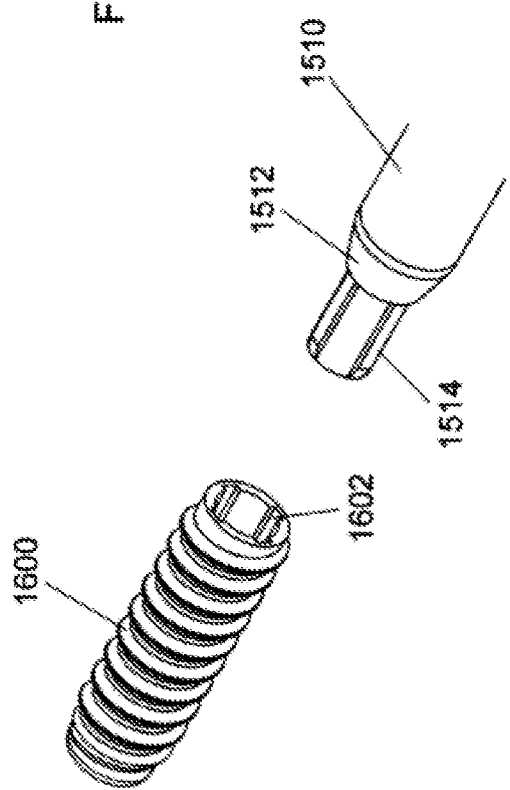
FIG. 2B is an expanded view of the distal portion of the objects of FIG. 2A at location B.
Figure 11:
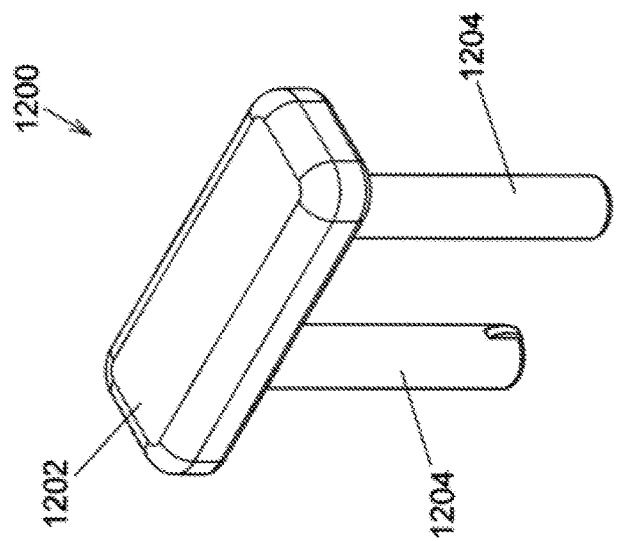
FIG. 11 is a perspective view of the objects of FIG. 10.
Figure 10:
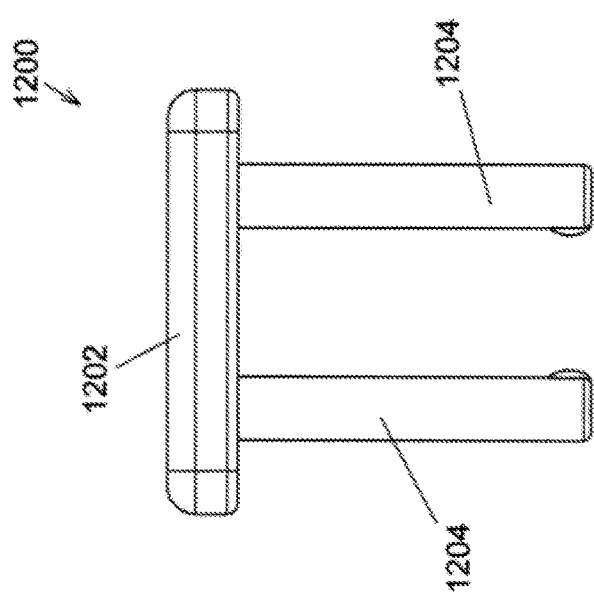
FIG. 10 is a side elevational view of an illustrative key for use in connection with an implant placement system of the present invention.

FIGS. 10 and 11 depict an illustrative embodiment of a removable key 1200 that may serve to prevent relative axial and rotational movement between the cannulated driver and the tensioning device. In this embodiment, key 1200 has a planar portion 1202 and cylindrical portions 1204 that are sized and spaced such that cylindrical portions 1204 may be inserted into off-axis lateral holes 1506 of handle 1502 of cannulated driver 1500.

Figure 12:
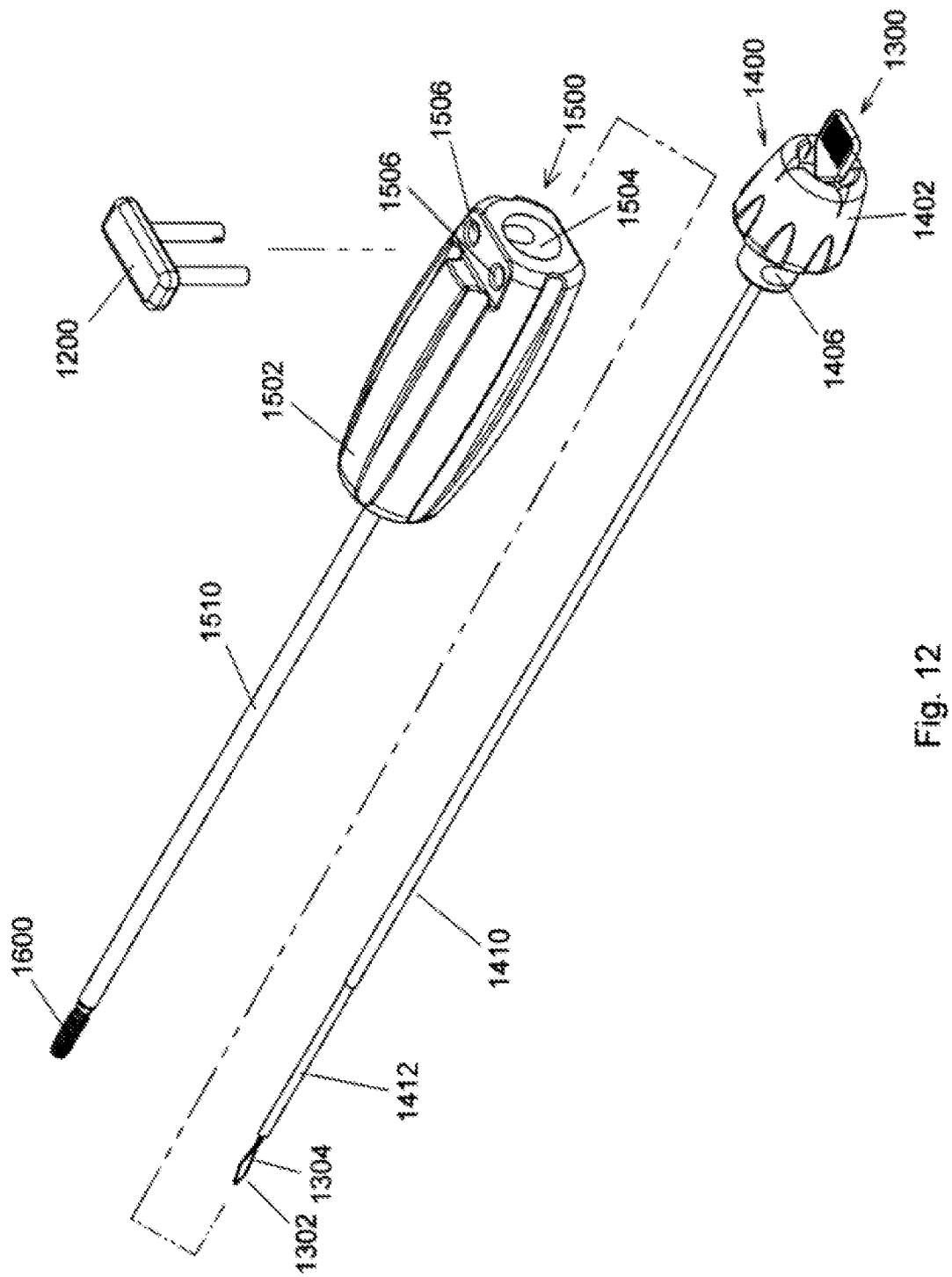
FIG. 12 is an exploded view of the assembly of the cannulated driver and anchor of FIG. 1A, the tensioning device of FIG. 3, and the key of FIG. 10 that together form a first embodiment of an implant placement system of the present invention.
Figure 13:
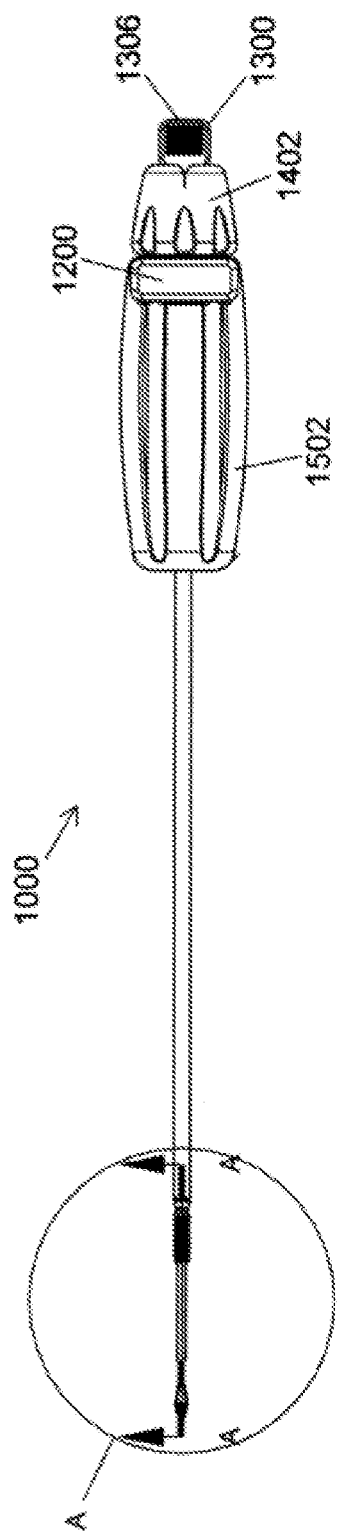
FIG. 13 is a plan view of a fully assembled first embodiment of an implant placement system of the present invention.
Figure 14:
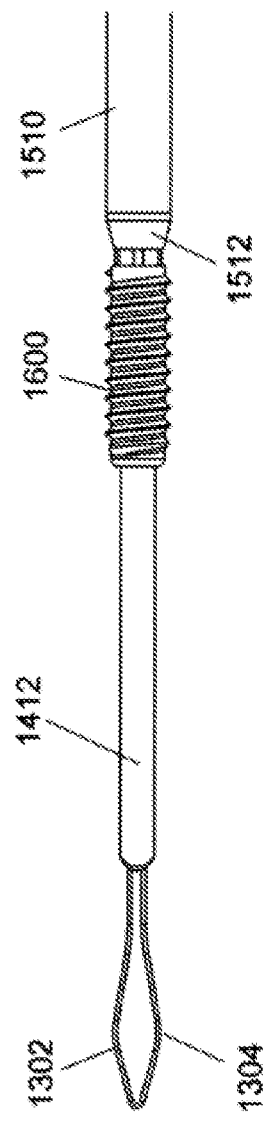
FIG. 14 is an expanded view of the distal portion of FIG. 13 at location A.
Figure 15:
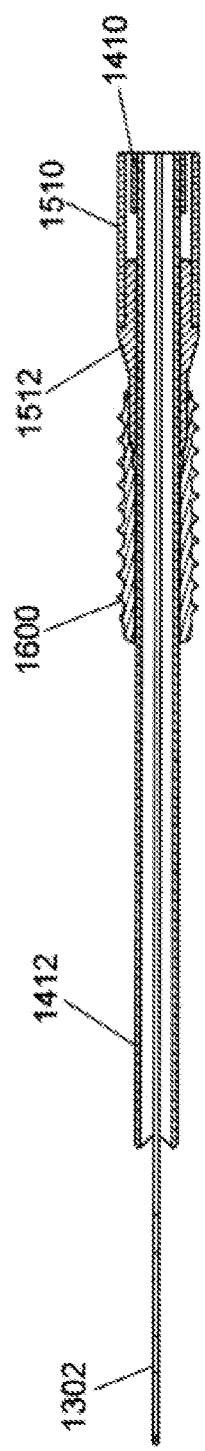
FIG. 15 is an expanded side elevational sectional view of the objects of FIG. 13 at location A-A.
Figure 16:
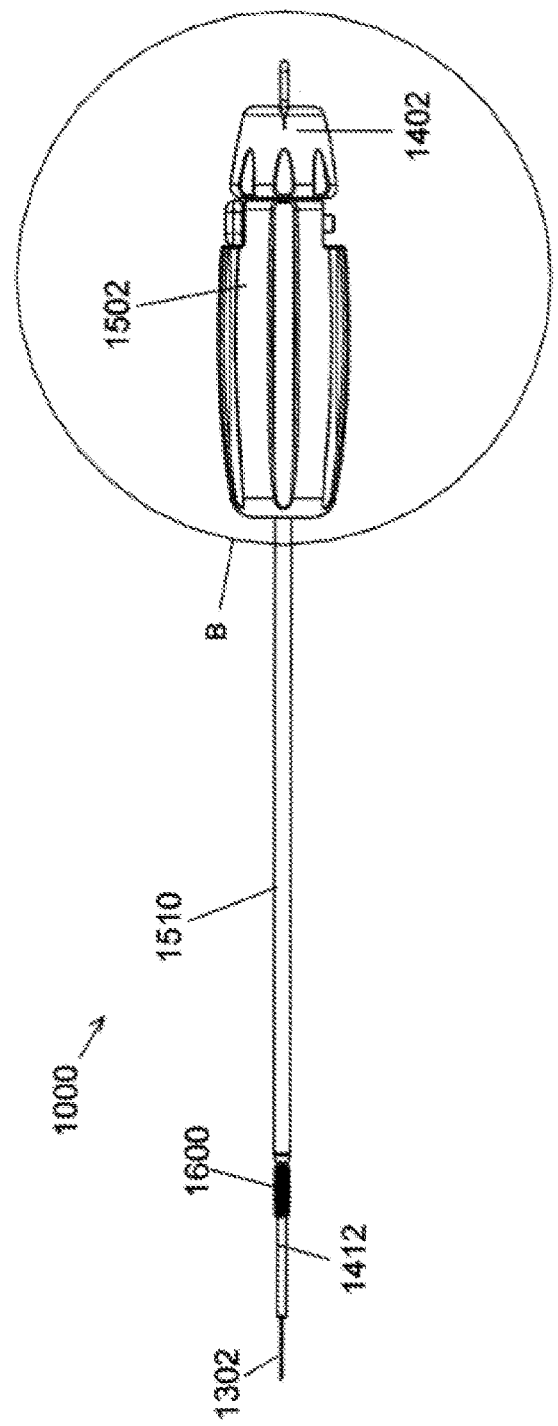
FIG. 16 is a side elevational view of the objects of FIG. 13.
Figure 17:
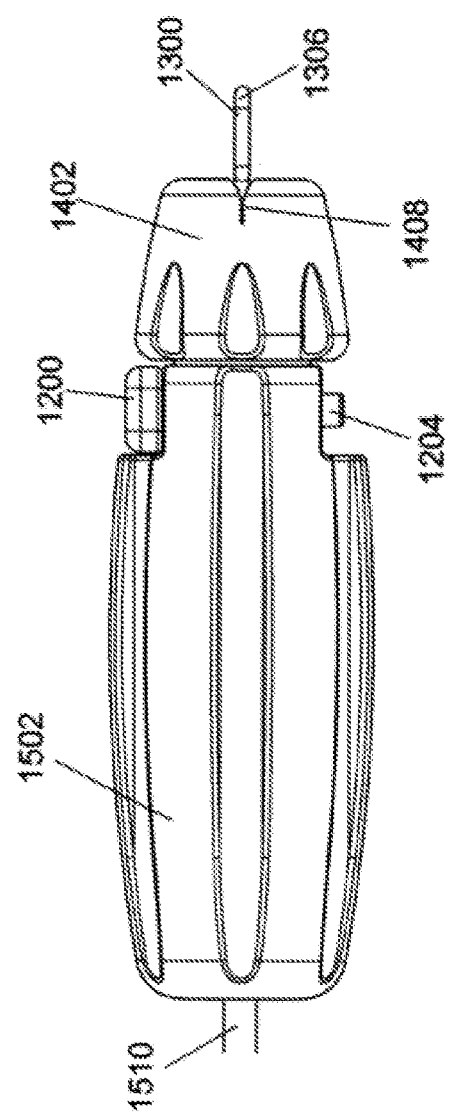
FIG. 17 is an expanded view of the objects of FIG. 13 at location B.
Figure 18:
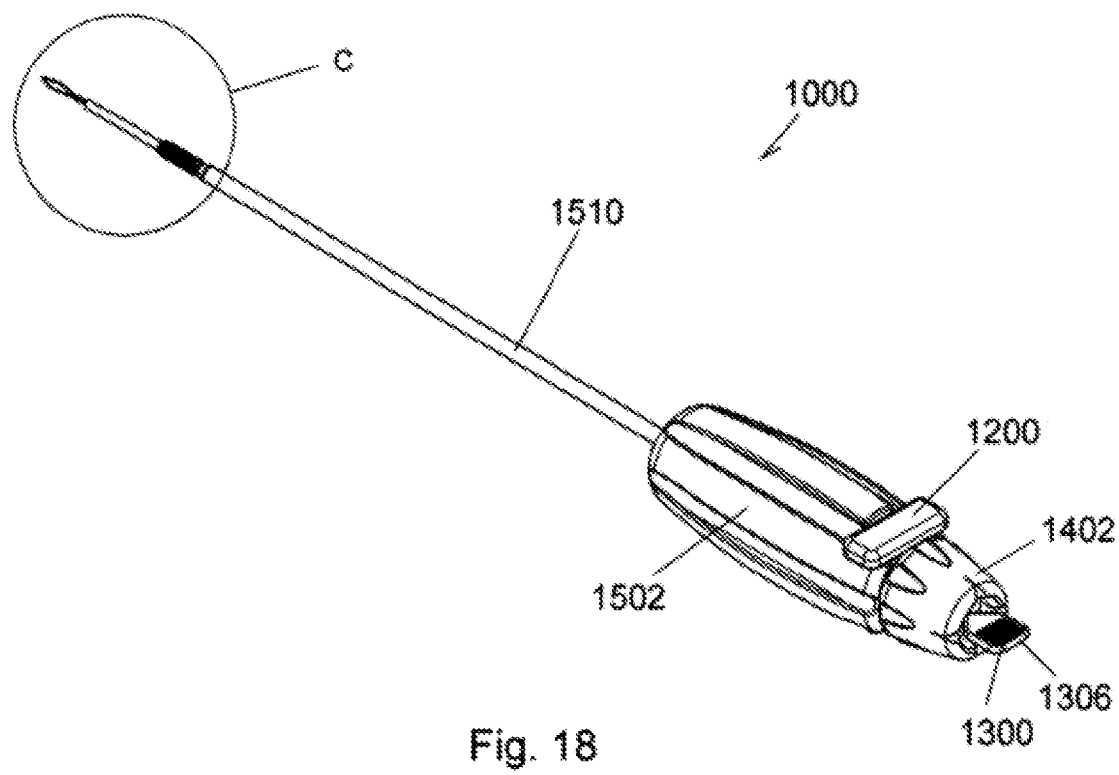
FIG. 18 is a perspective view of the objects of FIG. 13.
Figure 19:
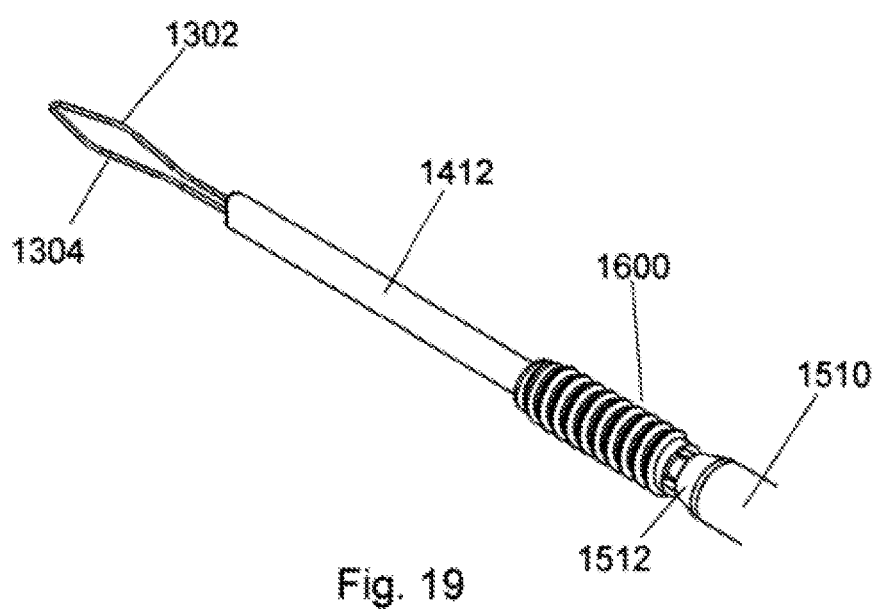
FIG. 19 is an expanded view of the objects of FIG. 13 at location C.

FIG. 12 depicts cannulated driver 1500 with anchor 1600 loaded thereto, tensioning device 1400 with loading loop 1300 positioned for loading a suture, and key 1200 prior to mounting of driver 1500 to tensioning device 1400 in preparation for use. When driver 1500 is mounted to tensioning device 1400, off-axis slots 1406 of handle 1402 of tensioning device 1400 are aligned with off-axis holes 1506 of handle 1502 of driver 1500 and cylindrical portions 1204 of key 1200 are inserted into the passages so formed. Positioning of key 1200 in this manner prevents axial and rotational movement of tensioning device 1400 relative to driver 1500. FIGS. 13 through 19 depict knotless suture anchor system 1000 of the present invention prepared for use with key 1200 and loading loop 1300 in place.

Figure 20:
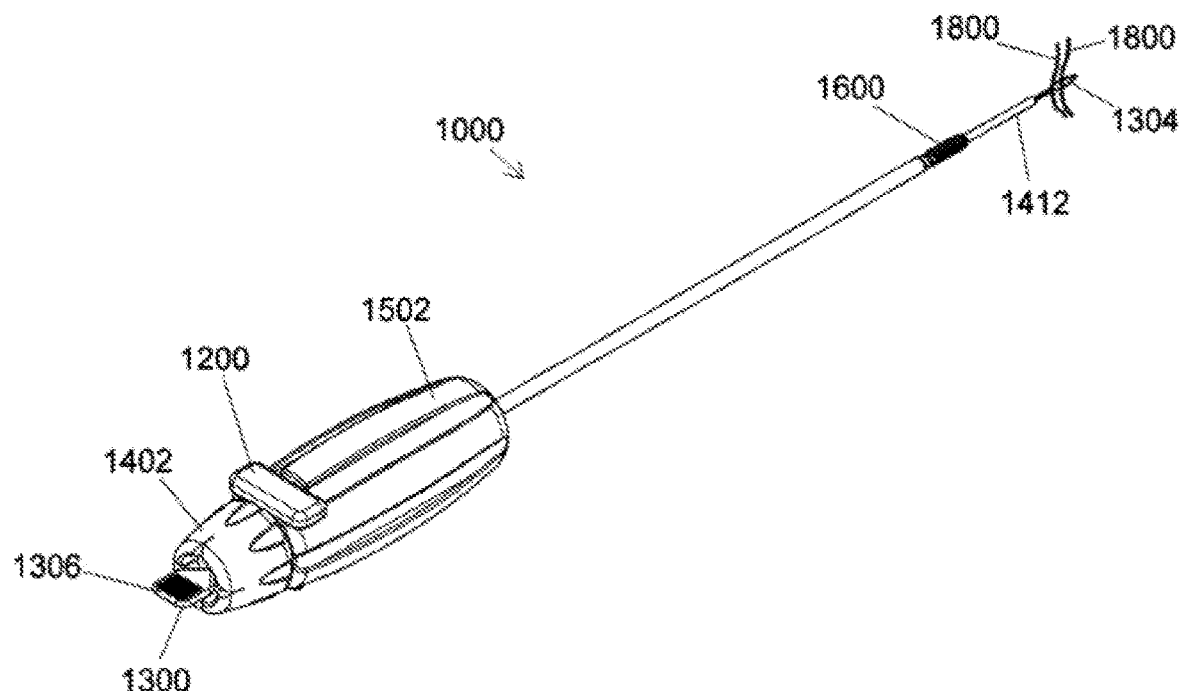
FIG. 20 is a perspective view of a first embodiment implant placement system with sutures being loaded into the system.
Figure 21:
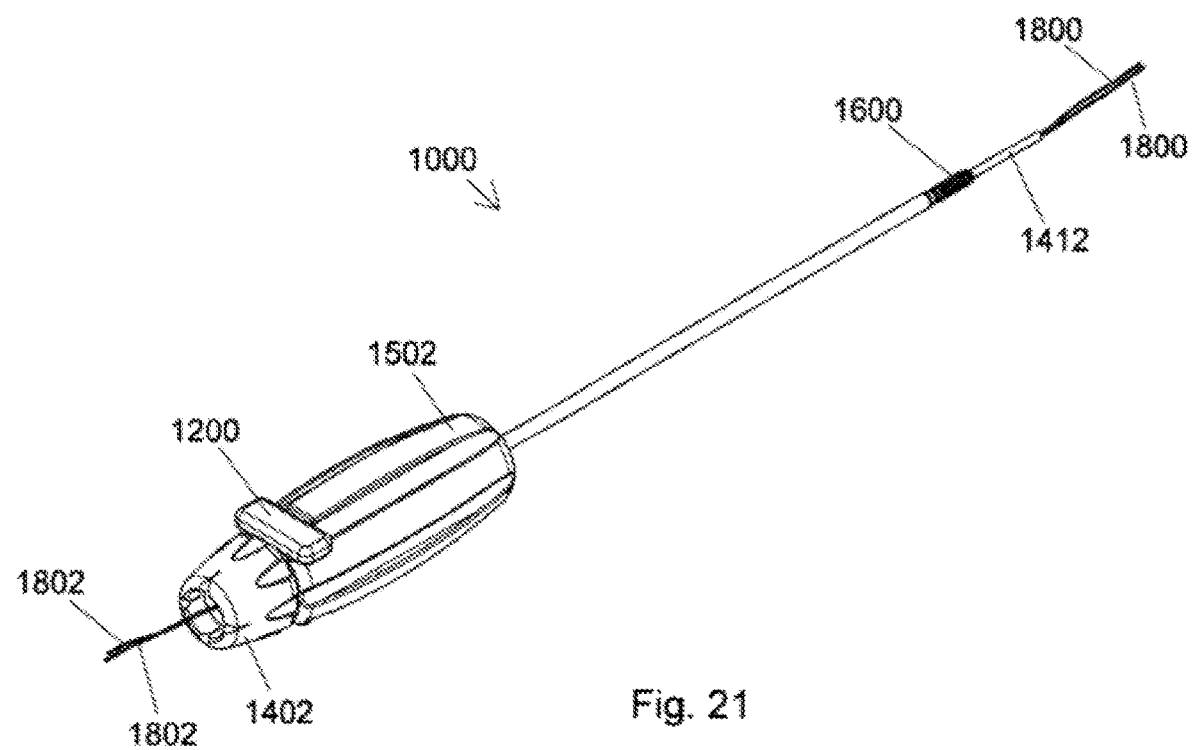
FIG. 21 is a perspective view of the first embodiment implant placement system with the sutures loaded.

Sutures 1800 are loaded into system 1000 by placing the proximal ends of sutures 1800 in distal loop 1304 of loading loop 1300 as depicted in FIG. 20. Tab 1306 of loading loop 1300 is withdrawn proximally until proximal ends 1802 of sutures 1800 extend proximally beyond hub 1402 of tensioning device 1400 as depicted in FIG. 21.

The present invention may be used to secure any type of soft tissue, graft, or tendon, such as, for example, a biceps tendon or a rotator cuff. An illustrative method of fixation according to the principles of the present invention is depicted in FIGS. 22 through 32.

Figure 22:
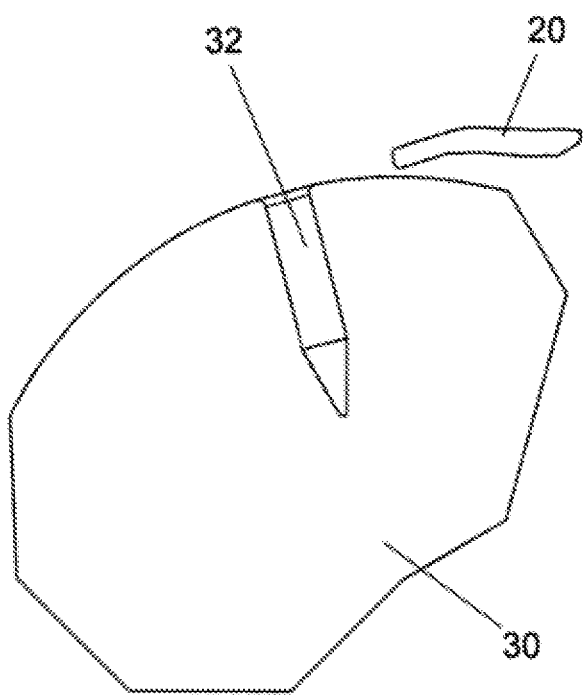
FIG. 22 schematically depicts a socket placed in a bone prior to the placement of an implant.
Figure 23:
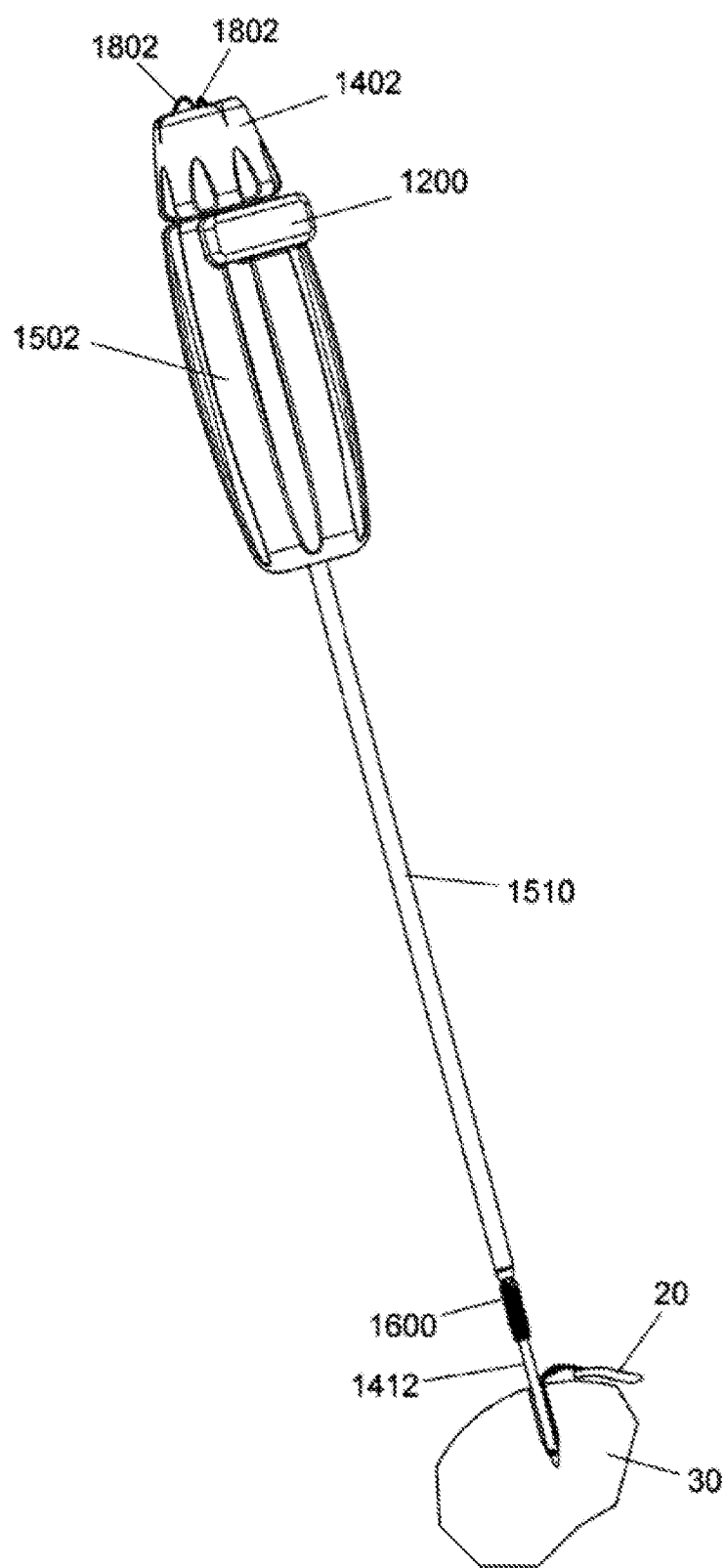
FIG. 23 depicts the first embodiment implant placement system positioned for the first step of implant placement.
Figure 24:
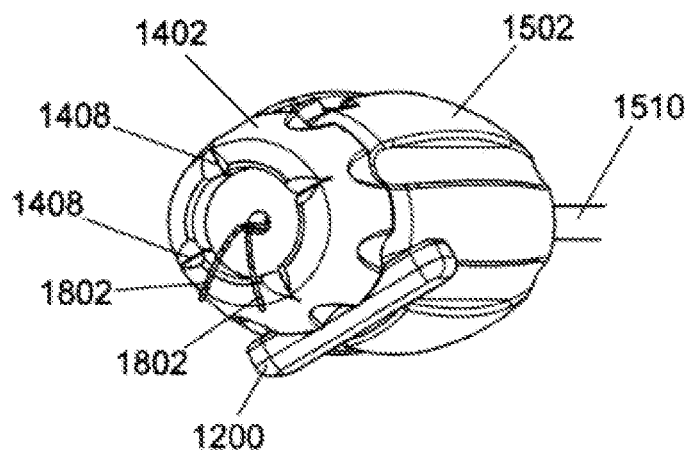
FIG. 24 depicts the proximal portion of the first embodiment implant placement system during the first step of implant placement.
Figure 25:
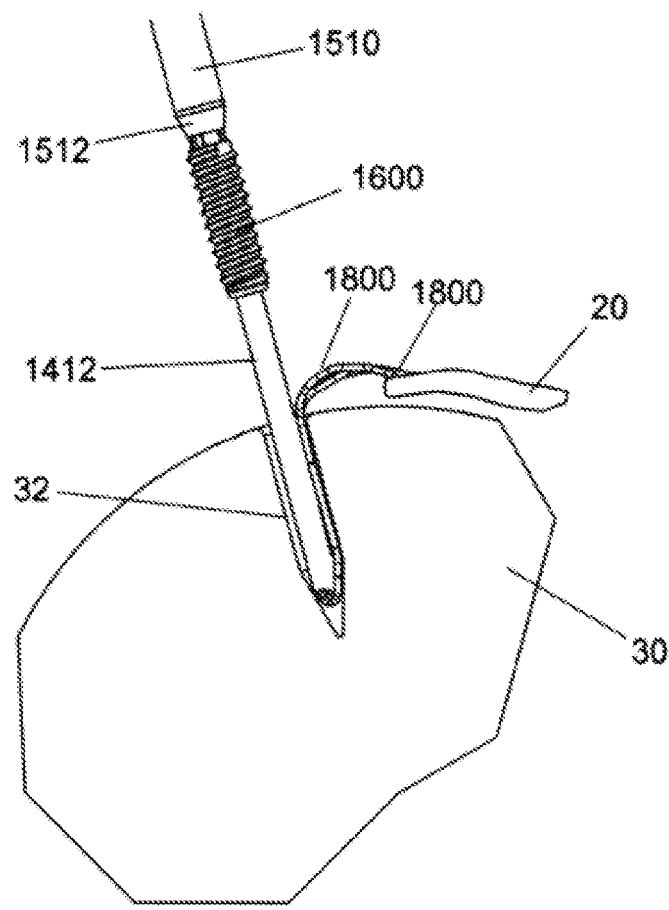
FIG. 25 depicts the distal portion of the first embodiment implant placement system during the first step of implant placement.
Figure 26:
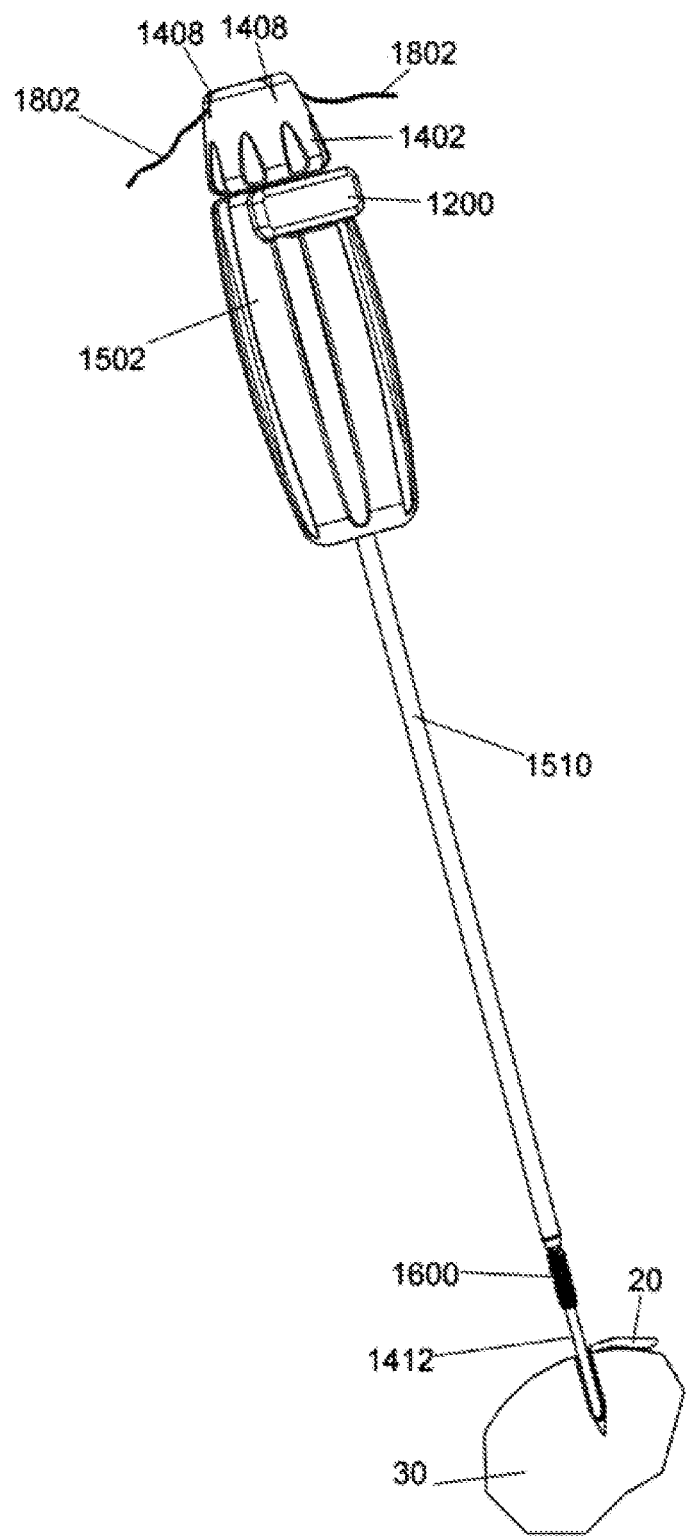
FIG. 26 depicts the first embodiment implant placement system positioned for the second step of implant placement.
Figure 27:
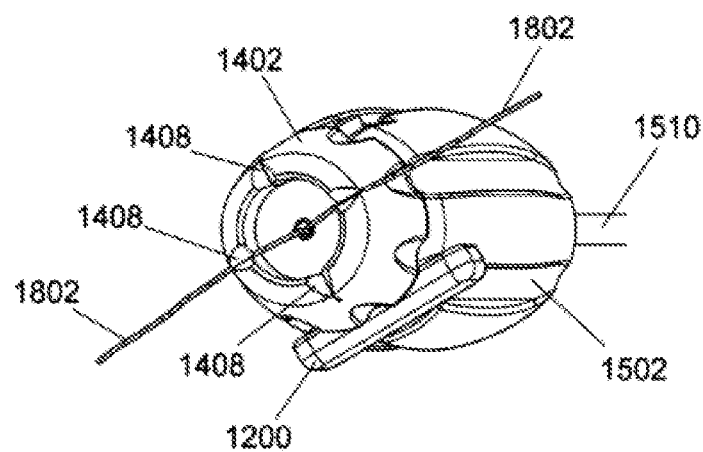
FIG. 27 depicts the proximal portion of the embodiment implant placement system during the second step of implant placement.
Figure 28:
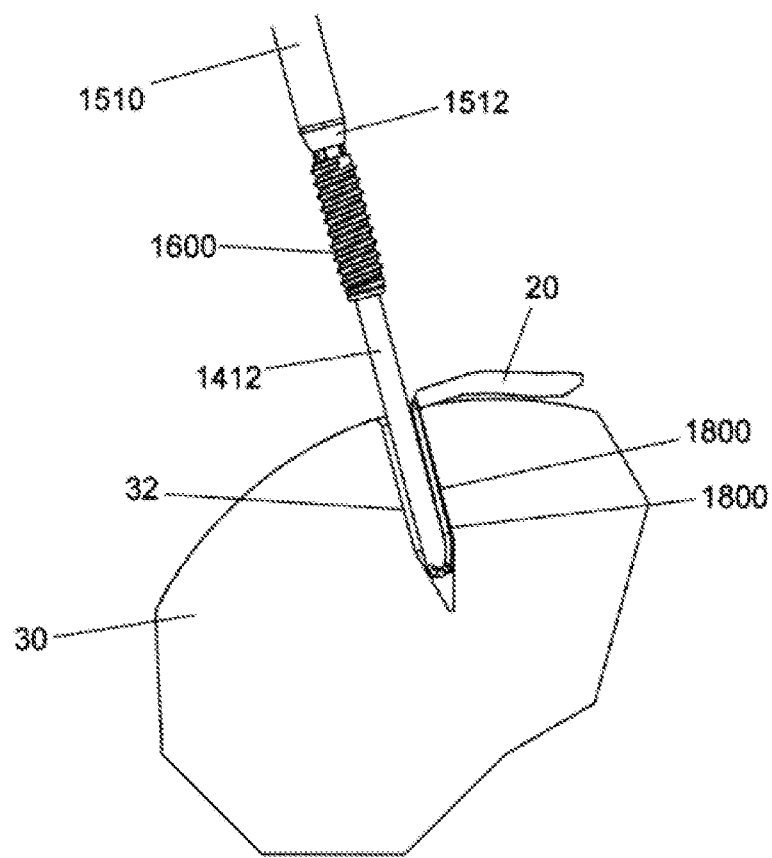
FIG. 28 depicts the distal portion of the first embodiment implant placement system during the second step of implant placement.
Figure 29:
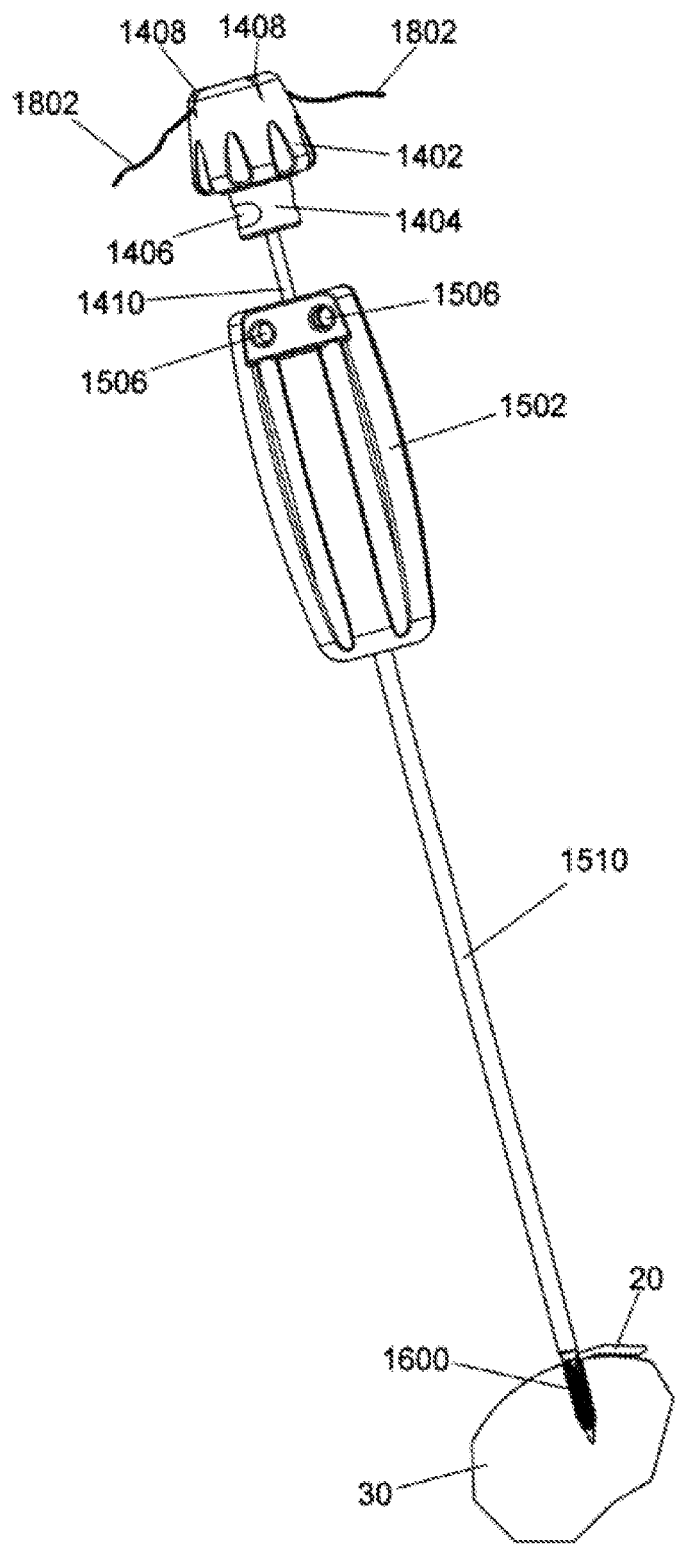
FIG. 29 depicts the first embodiment implant placement system positioned for the third step of implant placement.
Figure 30:
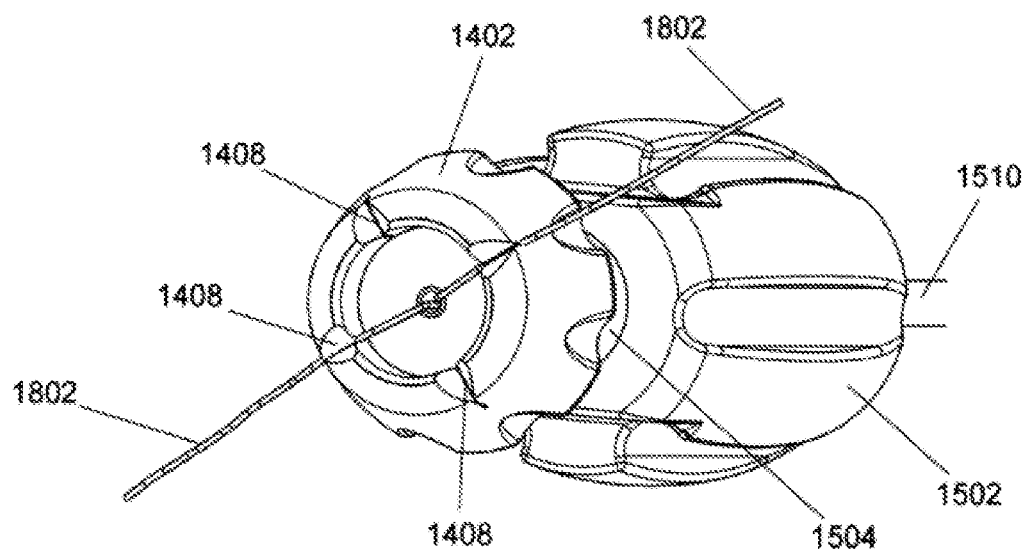
FIG. 30 depicts the proximal portion of the first embodiment implant placement system during the second step of implant placement.
Figure 31:
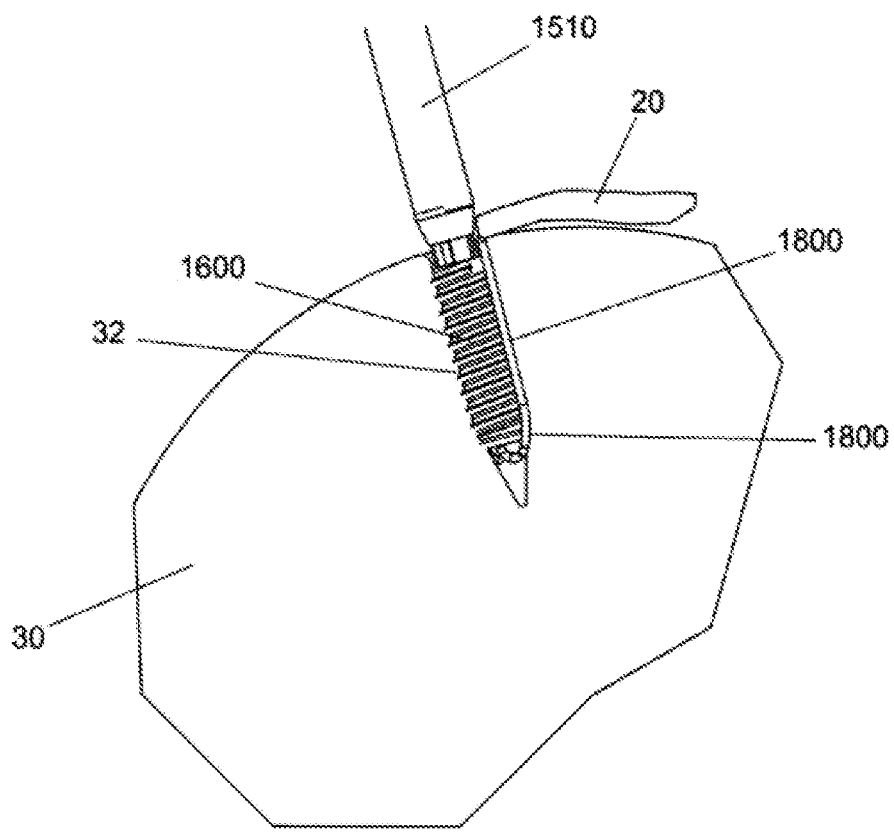
FIG. 31 depicts the distal portion of the first embodiment implant placement system during the third step of implant placement.
Figure 32:
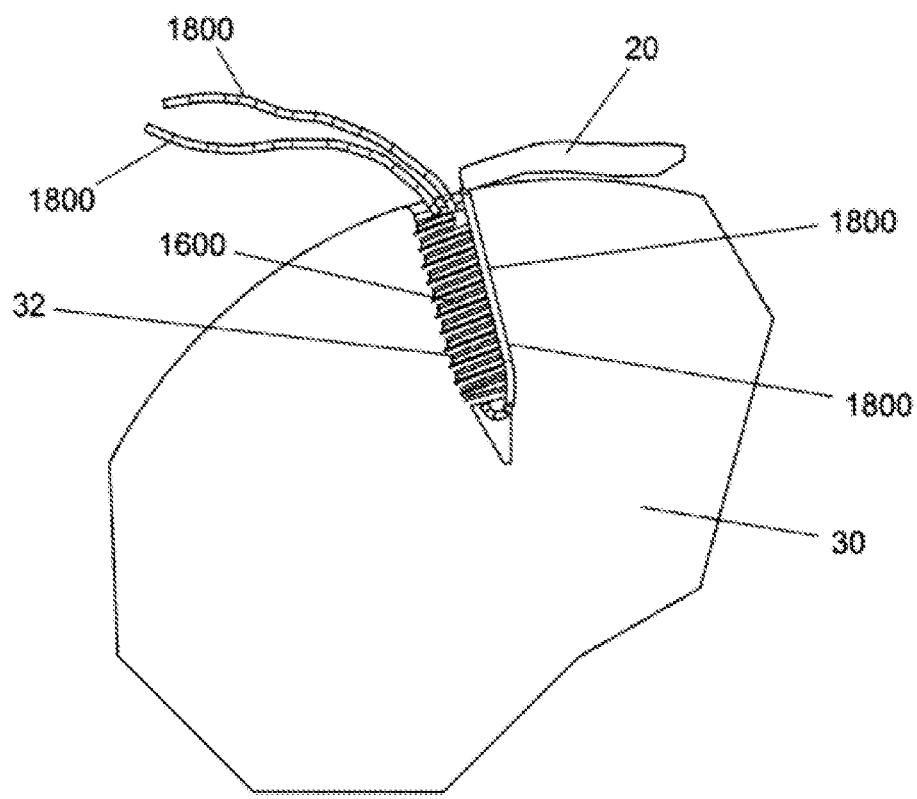
FIG. 32 depicts the site at the completion of implant placement using an implant placement system of the present invention.
Figure 33:
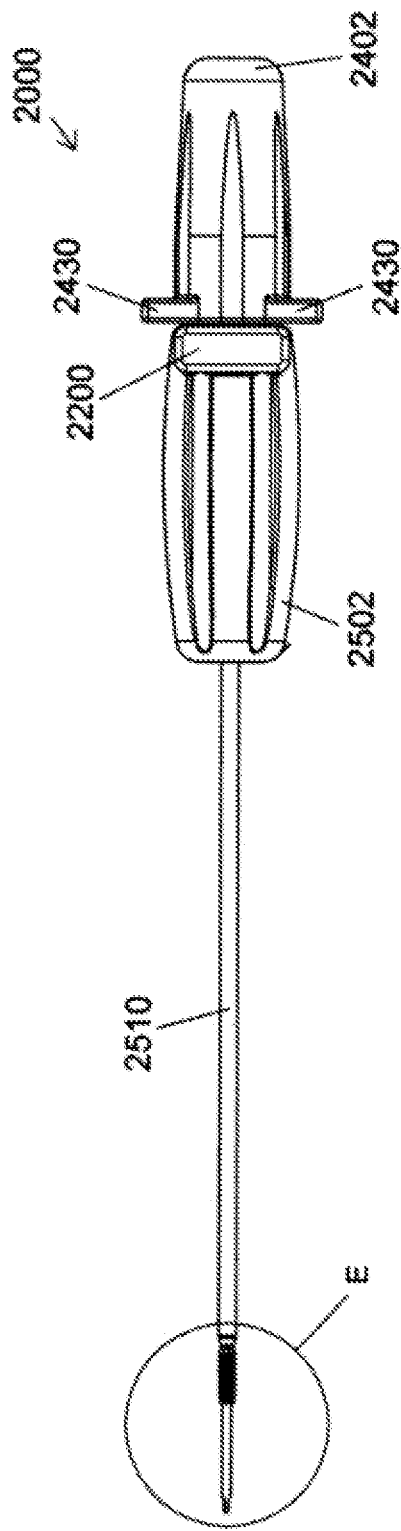
FIG. 33 is a plan view of a second embodiment of an implant placement system of the present invention, wherein the tubular distal portion of the tensioning device is replaced by a rod having formed at its distal end a sharpened fork portion.
Figure 34:
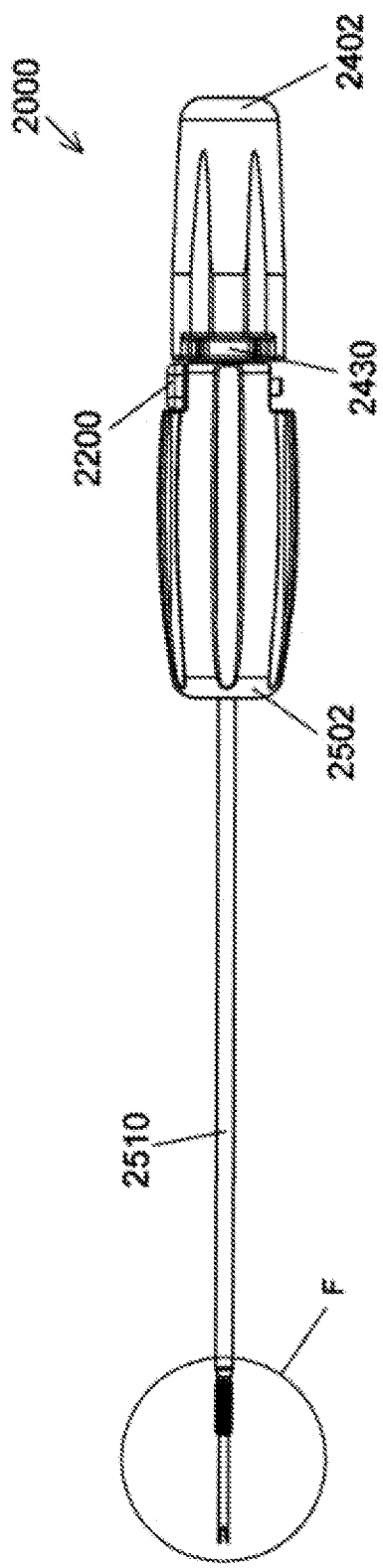
FIG. 34 is a side elevational view of the objects of FIG. 33.
Figure 35:
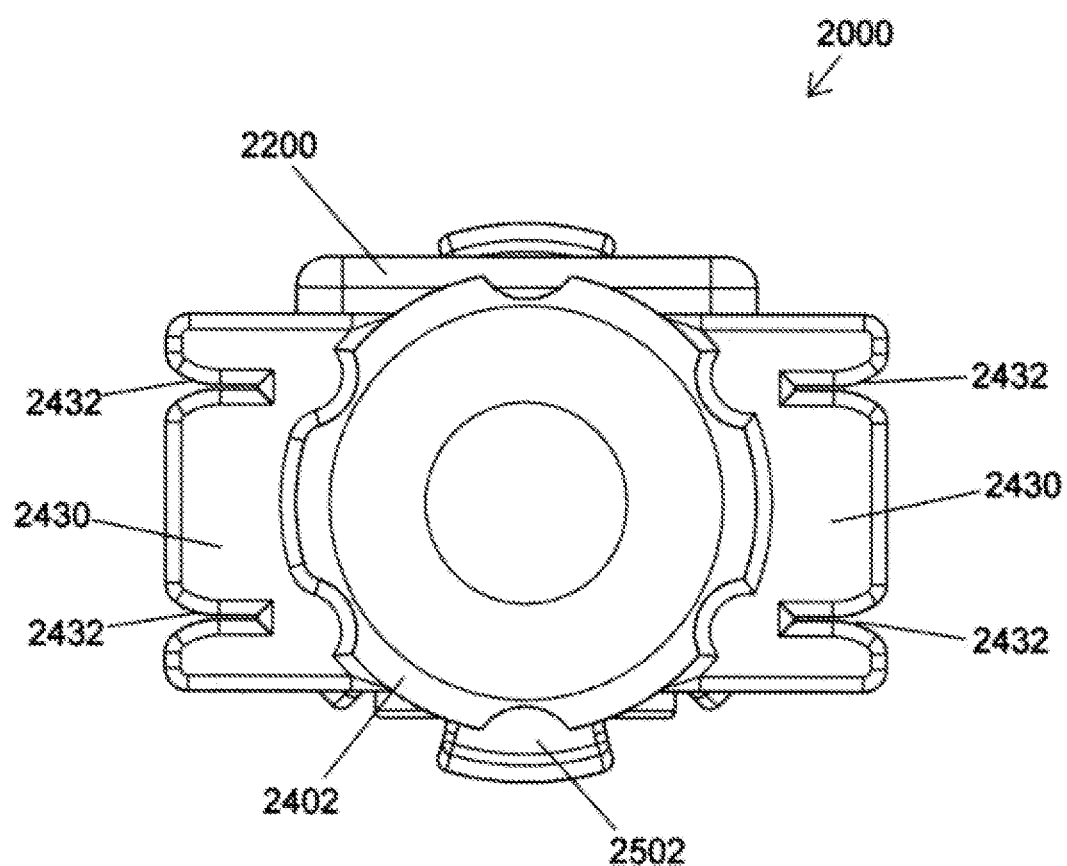
FIG. 35 is an expanded proximal end view of the objects of FIG. 33.
Figure 39:
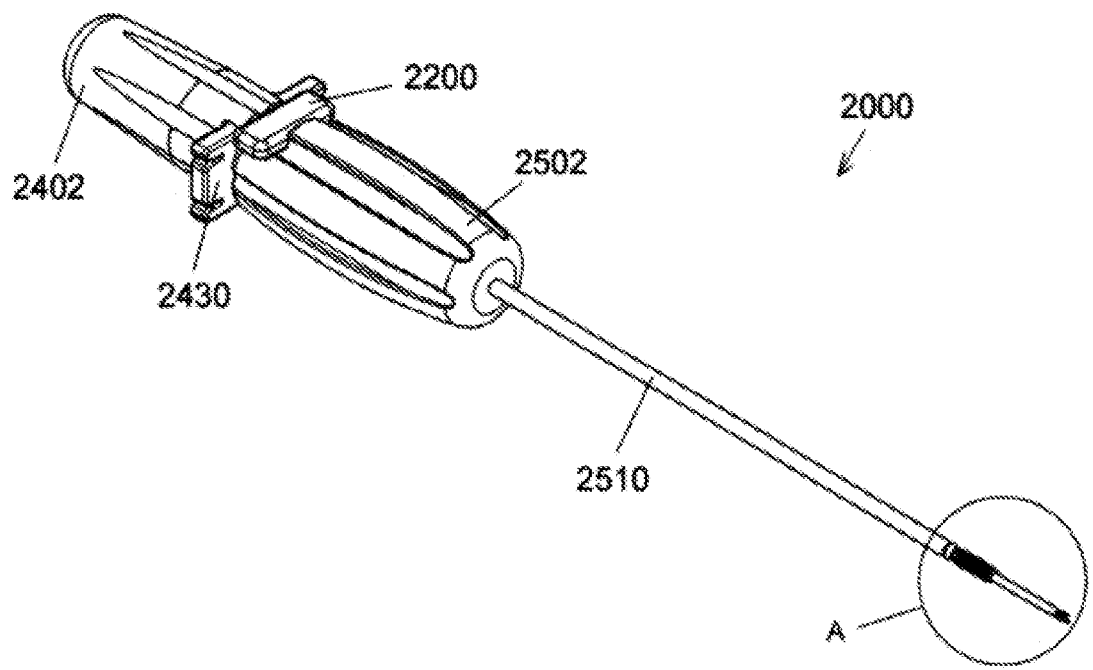
FIG. 39 is a distal perspective view of the objects of FIG. 33.
Figure 40:
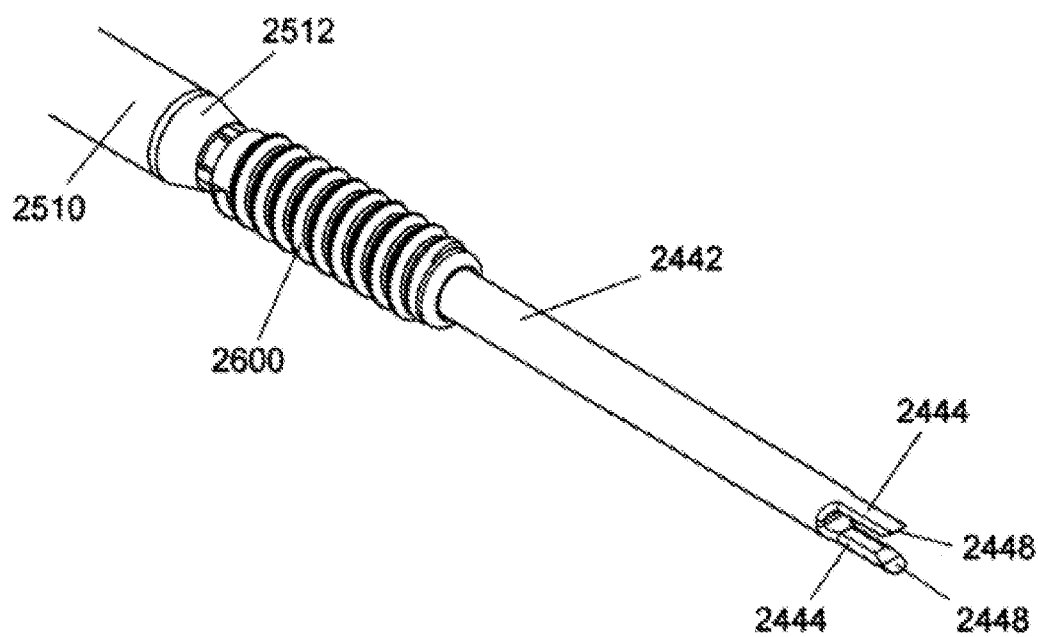
FIG. 40 is an expanded view of the objects of FIG. 39 at location A.
Figure 41:
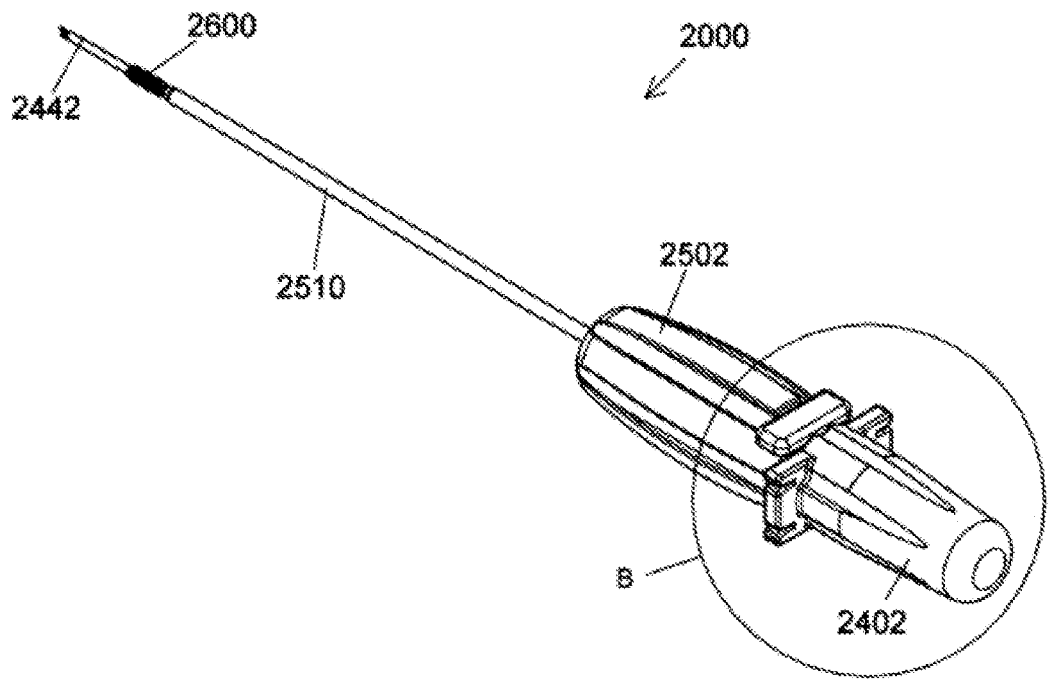
FIG. 41 is a proximal perspective view of the objects of FIG. 33.
Figure 42:
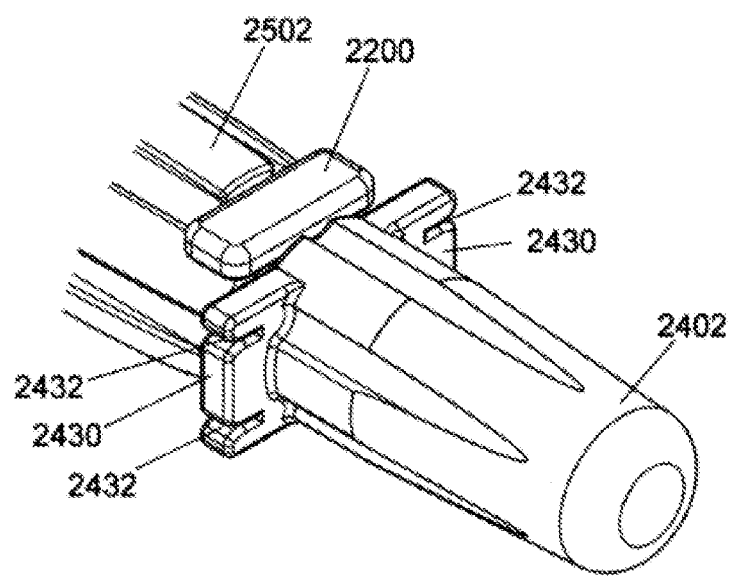
FIG. 42 is an expanded view of the objects of FIG. 41 at location B.

FIG. 22 schematically depicts a socket 32 formed by drilling or punching in bone 30, and a graft 20 to be affixed to bone 30. Sutures 1800 are passed through graft 20 in a usual manner; and the sutures loaded into system 1000 as previously described and depicted in FIGS. 20 and 21, such that suture proximal ends 1802 are accessible to the surgeon. Subsequently, distal tubular portion 1412 of tensioning device 1400 is inserted into socket 32 as depicted in FIGS. 23 through 25, the distal end of tubular portion 1412 contacting the bottom surface of socket 32. Thereafter, referring to FIGS. 26 through 28, the surgeon grasps proximal ends 1802 of sutures 1800 and withdraws them proximally so as to advance graft 20 towards socket 32. When graft 20 is in the desired position, proximal ends 1802 of sutures 1800 are secured in cleats 1408 to maintain the graft position. So long as proximal ends 1802 of sutures 1800 remain securely cleated and the distal end of tubular element 1412 is maintained in contact with the bottom surface of socket 32, the position of graft 20 will not change. The surgeon may adjust sutures 1800 as required to achieve optimal placement of graft 20. When this optimal placement of graft 20 has been achieved, while maintaining contact between the distal end off distal tubular element 1412 and the bottom of socket 32, the surgeon removes key 1200 from system 1000 so as to allow axial and rotational movement of driver 1500. The surgeon then advances anchor 1600 to socket 32 and screws the anchor into socket 32 so as to trap sutures 1800 between anchor 1600 and the wall of socket 32 in bone 30 as depicted in FIGS. 29 through 31. When anchor 1600 is fully inserted in socket 32, proximal ends 1802 of sutures 1800 are released from cleats 1408 and system 1000 is withdrawn from the joint, leaving the repair site as depicted in FIG. 32. Subsequently sutures 1800 are cut adjacent to anchor 1600 and the anchor placement is complete.

In an alternate method for anchor placement according to the present invention, the process may be simplified through use of an alternate embodiment in which the sutures are not drawn into a cannulation of the tensioning device, but rather are positioned and retained within a forked portion formed at the distal end of the tensioning device. In this alternate embodiment, sutures do not enter the lumen of the cannulated anchor, but rather wrap around the distal end of the anchor during insertion and are retained in place by friction between the external surfaces of the anchor and the boney surface of the socket at laterally opposed locations.

Such an alternate embodiment anchor placement system 2000 is depicted in FIGS. 33 through 42 and is identical to system 1000 in all aspects except as specifically subsequently described. Specifically, in this alternate embodiment, the cannulated distal tubular element 1412 of system 1000 is replaced by distal element 2442 that is not cannulated and has formed at its distal end elongate laterally opposed, distally extending portions 2444 with sharpened distal ends 2448. Elongate portions 2444 form the tines of a fork with channel 2446 formed between portions 2444. Tensioning device handle 2402 has formed near the distal end of its external surface flanges 2430 wherein are formed slots 2432 which serve as cleats for maintaining the tension of sutures placed therein, flanges 2430 and slots 2432 replacing slots 1408 in hub 1402 of system 1000.

Figure 43:
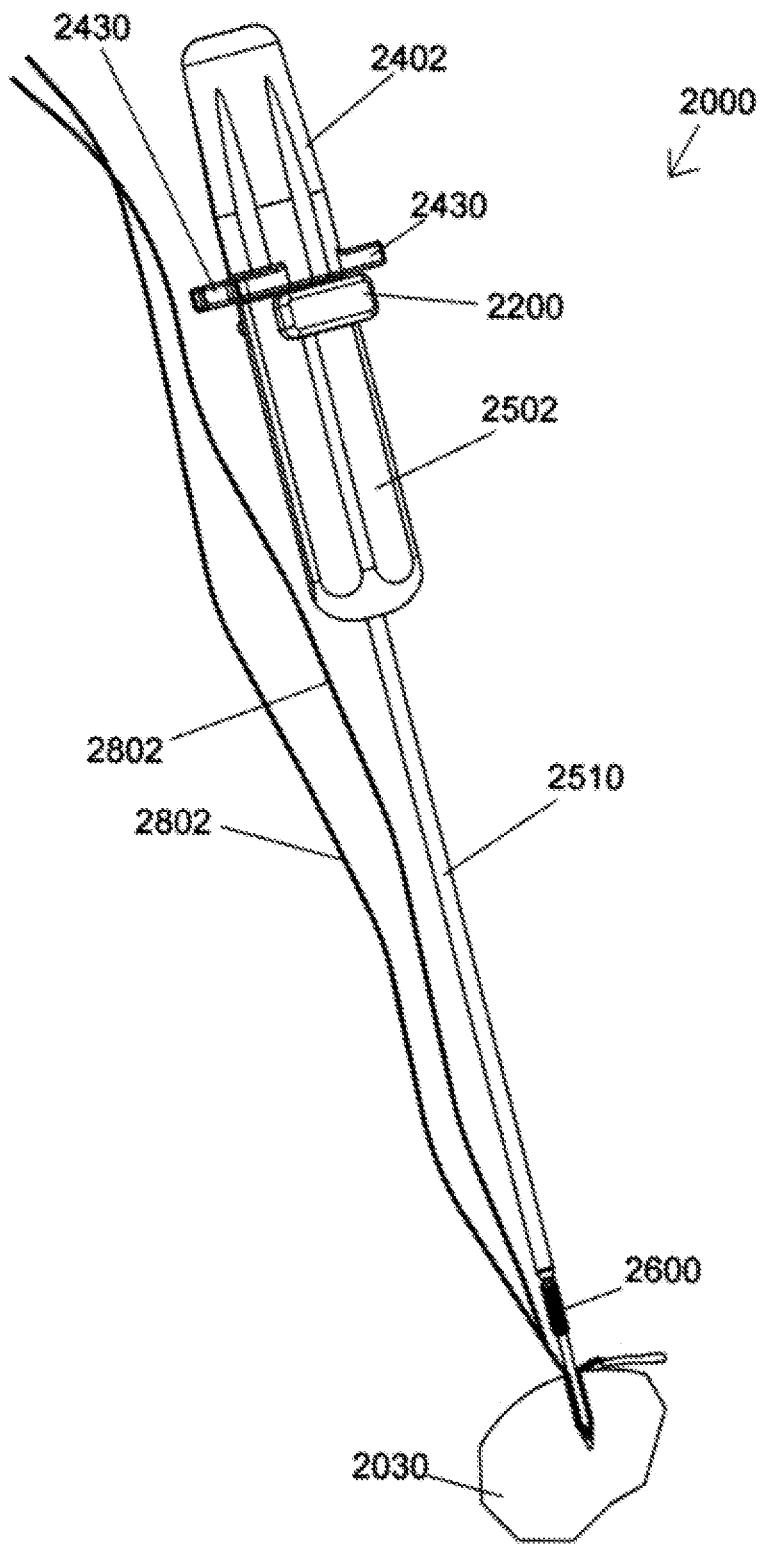
FIG. 43 depicts an illustrative method for positioning sutures in a socket for the securing of a graft with an anchor, using the assembly of FIG. 33.
Figure 44:
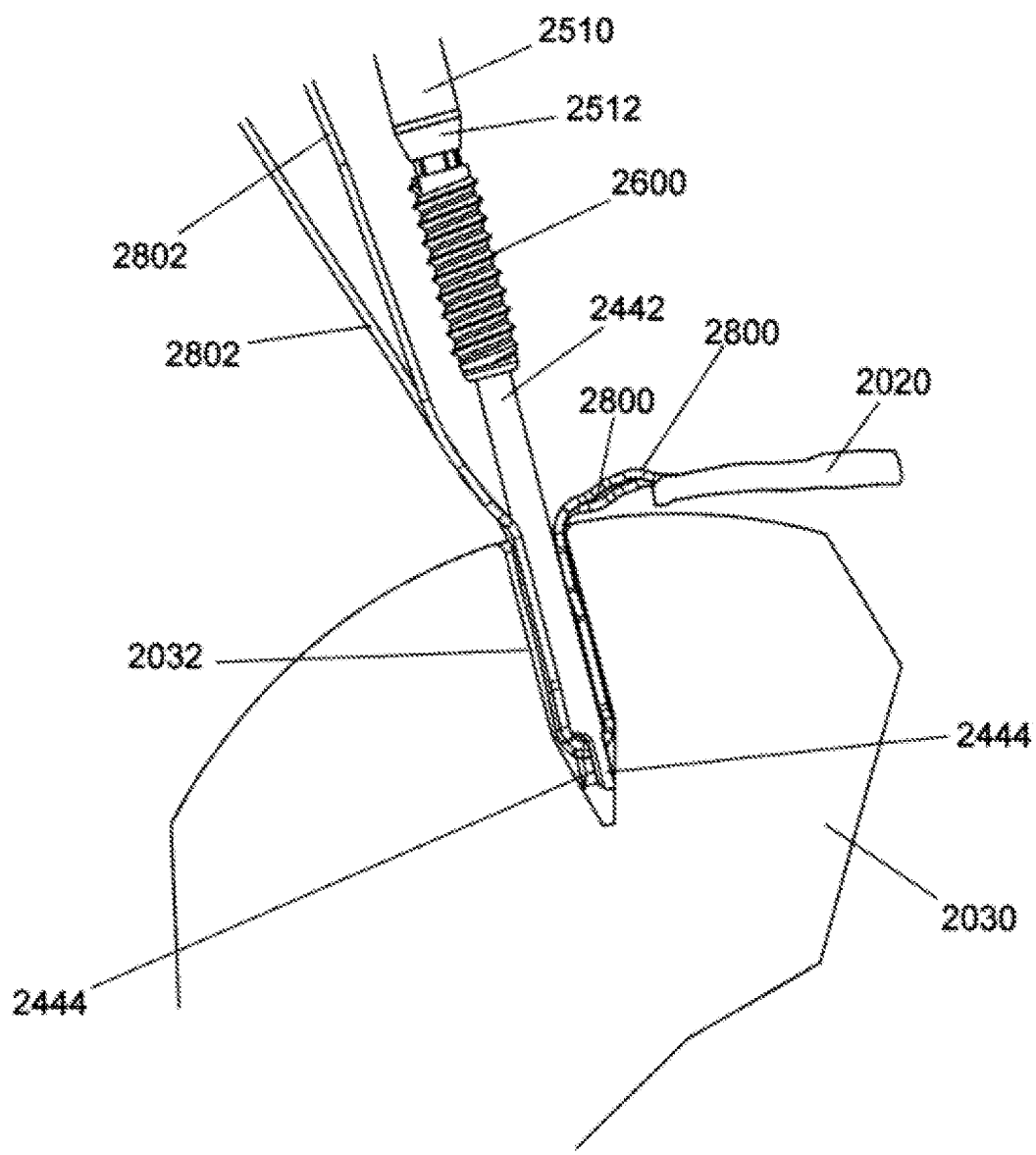
FIG. 44 is an expanded view of the distal portion of the objects of FIG. 43 that depicts the placement site.
Figure 45:
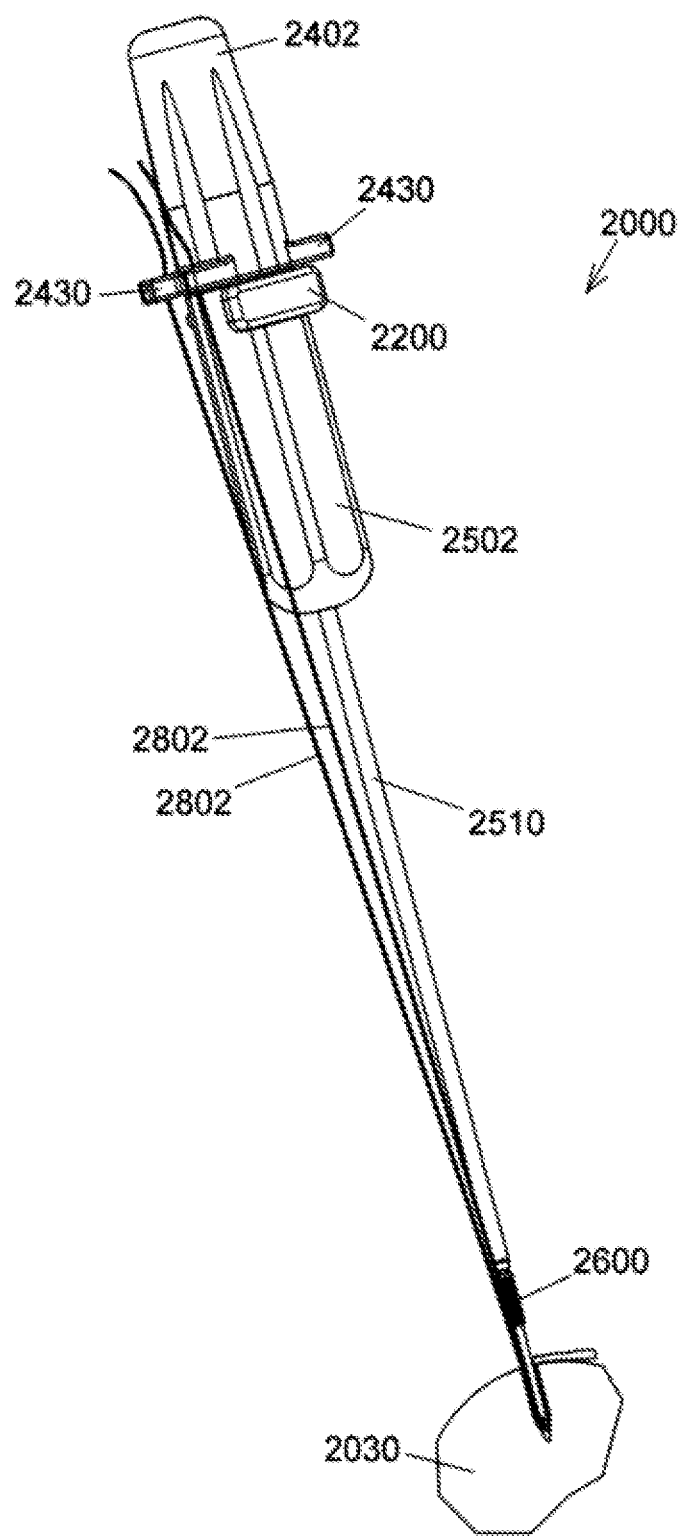
FIG. 45 depicts the alternate "fork" embodiment system of FIG. 33, with the sutures tensioned so as to position the graft.

A method of fixation according to the principles of the present invention using system 2000 is depicted in FIGS. 43 through 48. A socket 2032 is formed by drilling or punching in bone 2030. Sutures 2800 are passed through graft 2020 in a usual manner. Sutures 2800 are positioned within channel 2446 at the distal end of distal element 2442 of the tensioning device and distal element 2442 is inserted into socket 2032 such that the distal end of elongate portions 2444 contact the bottom of the socket as depicted in FIGS. 43 and 44. Thereafter, referring to FIGS. 45 and 46, the surgeon grasps proximal ends 2802 of sutures 2800 and withdraws them proximally so as to advance graft 2020 towards socket 2032. When graft 2020 is in the desired position, proximal ends 2802 of sutures 2800 are secured in cleats 2432 in flanges 2430 of handle 2402 to maintain the graft position.

Figure 47:
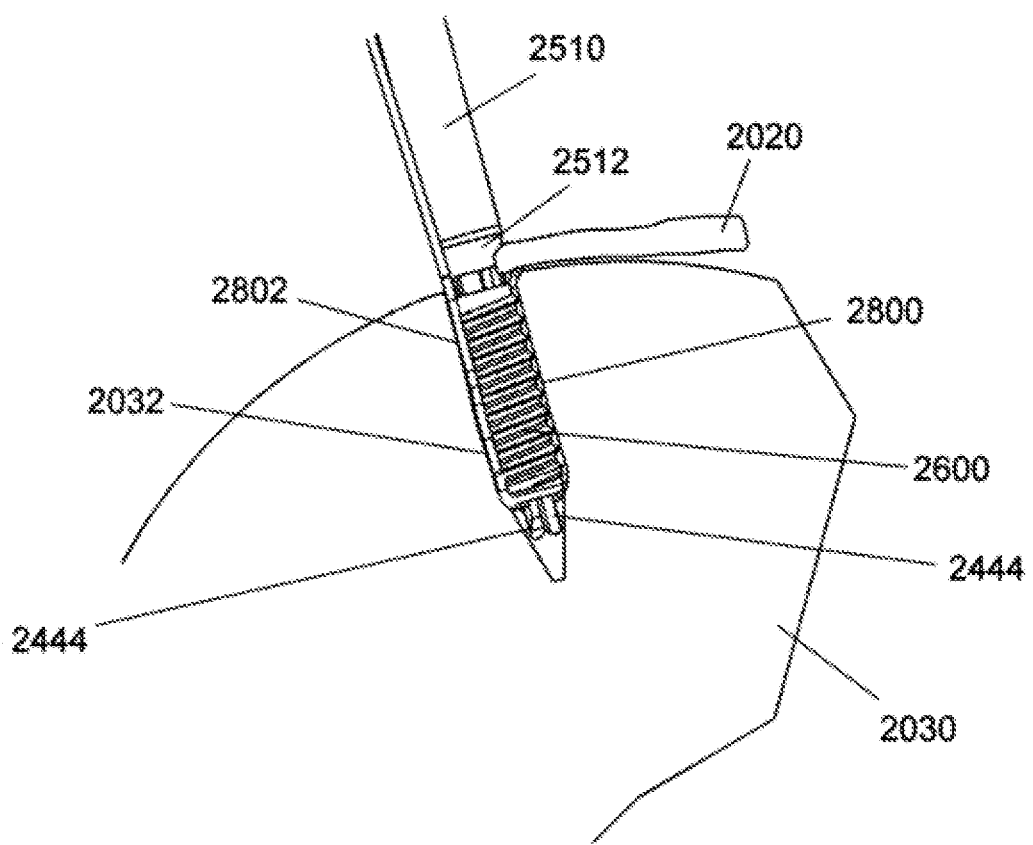
FIG. 47 is an expanded view of the site depicting the system with the anchor placed.

So long as proximal portions 2802 of sutures 2800 remain cleated and the distal end of distal tensioning element 2442 is maintained in contact with the bottom surface of socket 2032, the position of graft 2020 will not change. The surgeon may adjust sutures 2800 as required to achieve optimal placement of graft 2020. When this optimal placement of graft 2020 has been achieved, while maintaining contact between the distal end off distal tubular element 2442 and the bottom of socket 2032, the surgeon removes key 2200 from system 2000 so as to allow axial and rotational movement of the driver assembly. The surgeon advances anchor 2600 to socket 2032 and screws the anchor into socket 2032 so as to trap sutures 2800 between anchor 2600 and the walls of socket 2032 in bone 2030 as depicted in FIG. 47. When anchor 2600 is fully inserted in socket 2032, proximal portions 2802 of sutures 2800 are released from cleats 2432 and system 2000 is withdrawn from the joint. Subsequently suture proximal portions 2802 of sutures 2800 are cut adjacent to anchor 2600 and the anchor placement is complete. The position of the graft is maintained by friction between the sutures 2800 that are trapped between the exterior surface of anchor 2600 and two laterally opposed portions of the walls of socket 2032.

Anchor placement systems of the present invention are also useful for the attachment of tendons in a procedure called bio-tenodesis. When attaching, for instance, a biceps tendon to the humeral shaft, the proximal end of the tendon is inserted into the socket and the implant placed in a manner that traps the tendon between the anchor and the wall of the socket thereby retaining the tendon in the socket.

Figure 49:
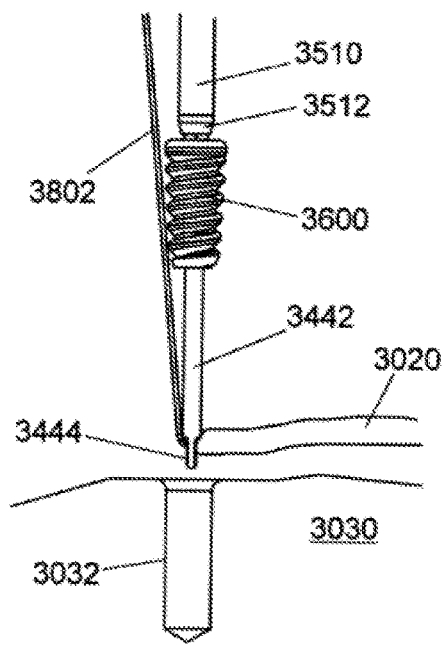
FIG. 49 depicts a first step of an alternate repair method for securing a graft in a socket using an implant placement system as contemplated by the present invention.
Figure 50:
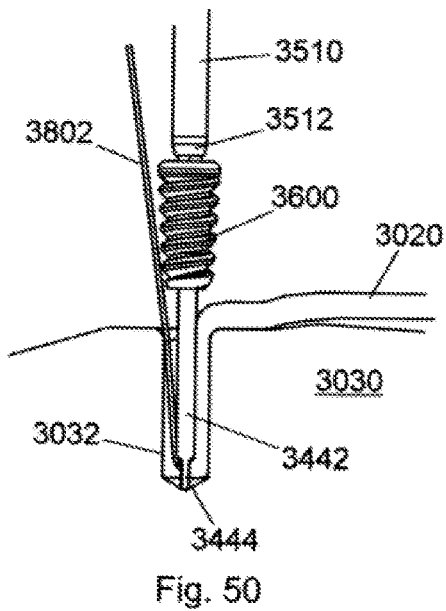
FIG. 50 depicts a second step of the alternate repair method
Figure 51:
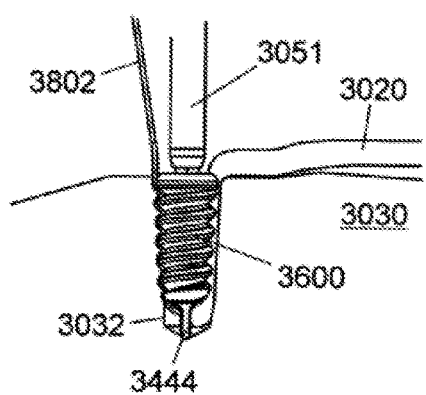
FIG. 51 depicts a third step of the alternate repair method.
Figure 52:
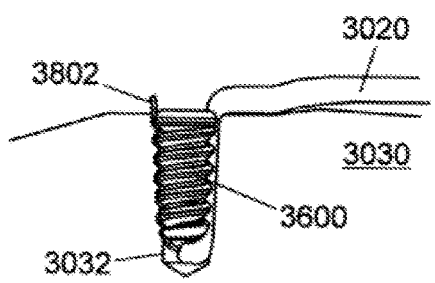
FIG. 52 depicts the site of the graft attachment at the completion of the repair using the alternate repair method.

FIGS. 49 through 52 depict an alternate embodiment of a method for fixation of a tendon graft using system 2000. As is commonly done in preparation for a bio-tenodesis type procedure, the portion of the graft that is to be inserted into the socket is first sutured in a circumferential manner, the sutures providing added resistance to pull-out when the repair is completed. Excess suture from the circumferential suturing (also called "whip stitching") is used to position the tendon prior to anchoring by the implant. Unlike previous embodiment methods disclosed herein, the positioning of graft 3020 is not achieved by tensioning the sutures after distal element 3442 is inserted into socket 3032. Rather, as depicted in FIG. 49 sutures 3802 are positioned within channel 3446 at the distal end of distal element 3442 of the tensioning device and tensioned such that graft 3020 is positioned and retained adjacent to the distal end of distal element 3442 adjacent to distally extending portions 3444. Tension in sutures 3802 is then maintained by cleating in the manner previously herein described. Thereafter, distal element 3444 is inserted into socket 3032 as shown in FIG. 50 and anchor 3600 is placed as depicted in FIG. 51 trapping graft 3020 between anchor 3600 and the boney surface of the wall of socket 3032 at a first location, and trapping sutures 3082 between anchor 3600 and the boney surface of the wall of socket 3032 at a second location. Friction forces acting at these locations maintain the position of graft 3020 relative to socket 3032 and bone 3030. FIG. 52 depicts the site at completion of the anchor placement and removal of insertion system 3000.

Figure 53:
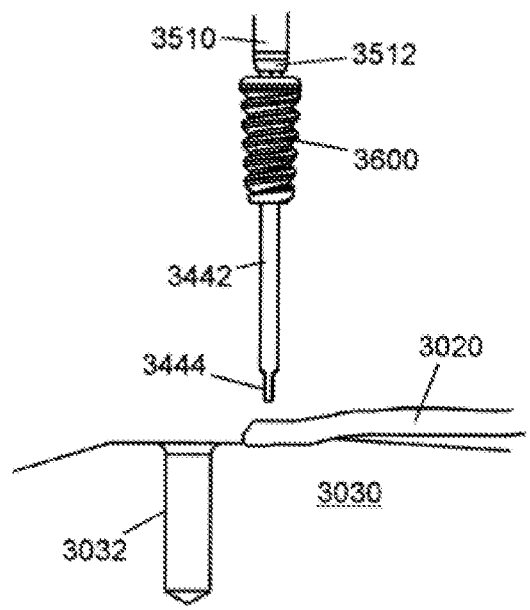
FIG. 53 depicts a first step of a second alternate repair method for securing a graft in a socket using an implant placement system as contemplated by the present invention.
Figure 54:
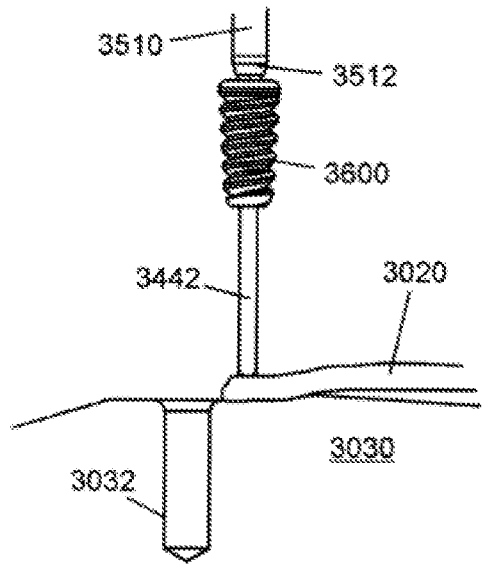
FIG. 54 depicts a second step of the second alternate repair method
Figure 55:
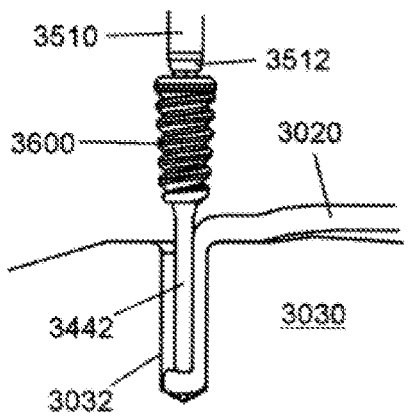
FIG. 55 depicts a third step of the second alternate repair method.
Figure 56:
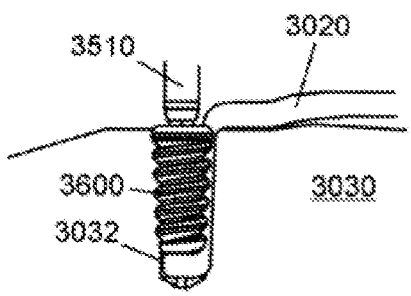
FIG. 56 depicts a fourth step of the second alternate repair method.
Figure 57:
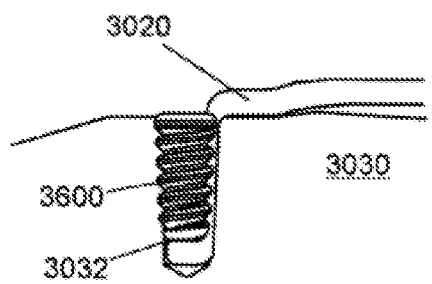
FIG. 57 depicts the site of the graft attachment at the completion of the repair using the second alternate embodiment repair method.

FIGS. 53 through 57 depict an alternate method of anchoring a graft to bone using the alternate anchor placement system 2000 of the present invention. Rather than using tensioned sutures to maintain the placement of a graft at the distal end of distal element 3442 as previously depicted in FIG. 49, the graft is impaled on the distally extending portions 3444 of distal element 3442 as shown in FIGS. 53 and 54, the sharpened distal ends 3448 of extending portions 3444 penetrating the graft. Thereafter, distal element 3444 is inserted into socket 3032 as shown in FIG. 55 and anchor 3600 is placed as depicted in FIG. 56 trapping graft 3020 between anchor 3600 and the boney surface of the wall of socket 3032. Friction force between the inserted portion of graft 3020 and socket 3032 maintains the position of graft 3020 relative to socket 3032 and bone 3030. FIG. 57 depicts the site at completion of the anchor placement and removal of insertion system 3000. If the graft has been whip-stitched and the excess suture remains, the suture tails will also be trapped between anchor 3600 and socket 3032 thereby providing additional resistance to pull out.

Figure 58:
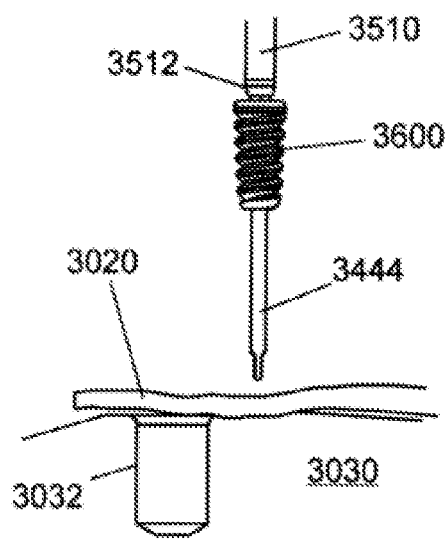
FIG. 58 depicts a first step of a third alternate repair method for securing a graft in a socket using an implant placement system as contemplated by the present invention.
Figure 59:
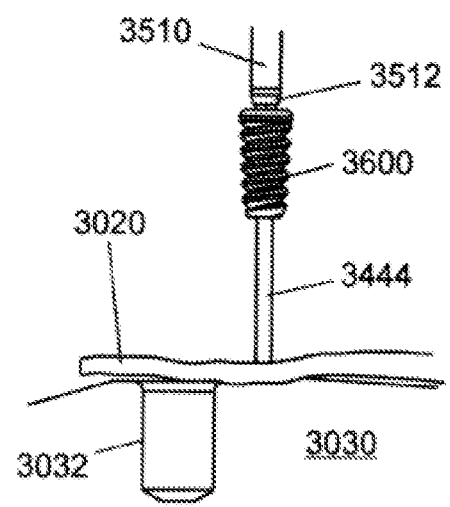
FIG. 59 depicts a second step of the third alternate repair method
Figure 60:
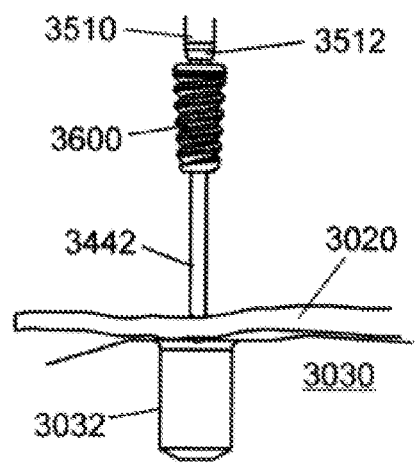
FIG. 60 depicts a third step of the third alternate repair method.
Figure 61:
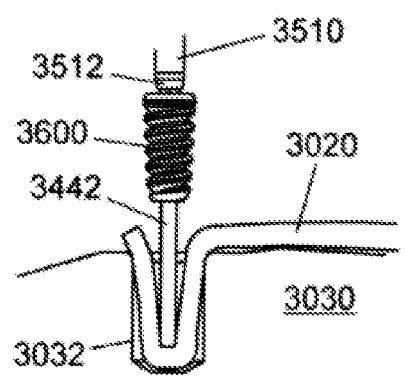
FIG. 61 depicts a fourth step of the third alternate repair method.
Figure 62:
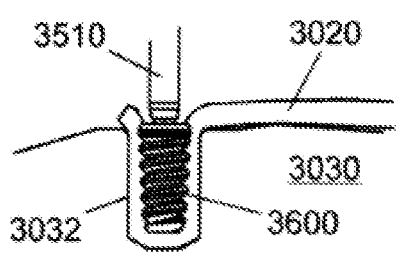
FIG. 62 depicts a fifth step of the third alternate repair method.
Figure 63:
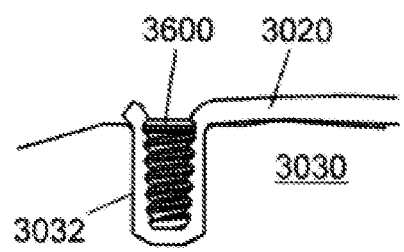
FIG. 63 depicts the site of the graft attachment at the completion of the repair using the third alternate embodiment repair method.
Figure 68:
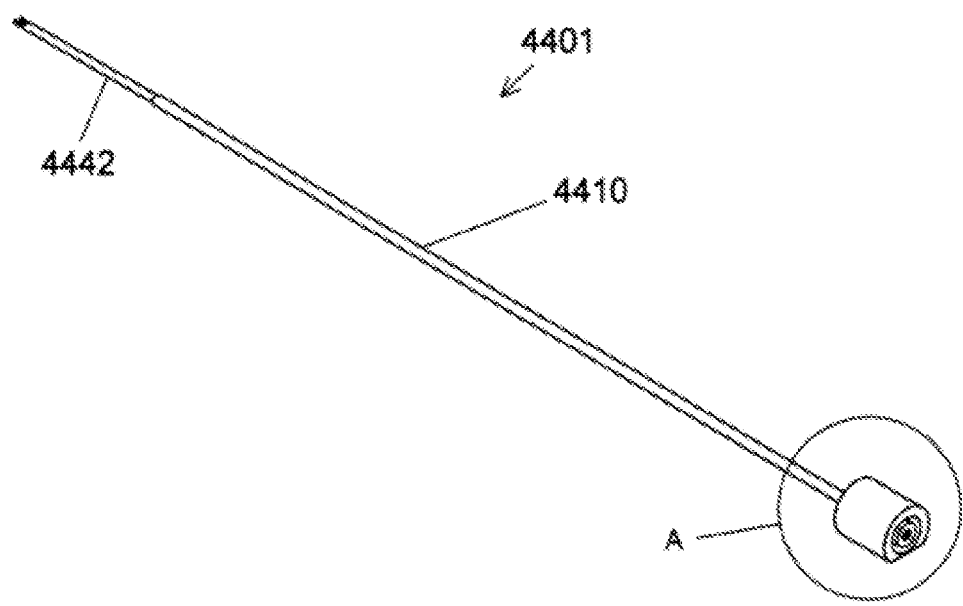
FIG. 68 is a perspective view of the objects of FIG. 64.
Figure 69:
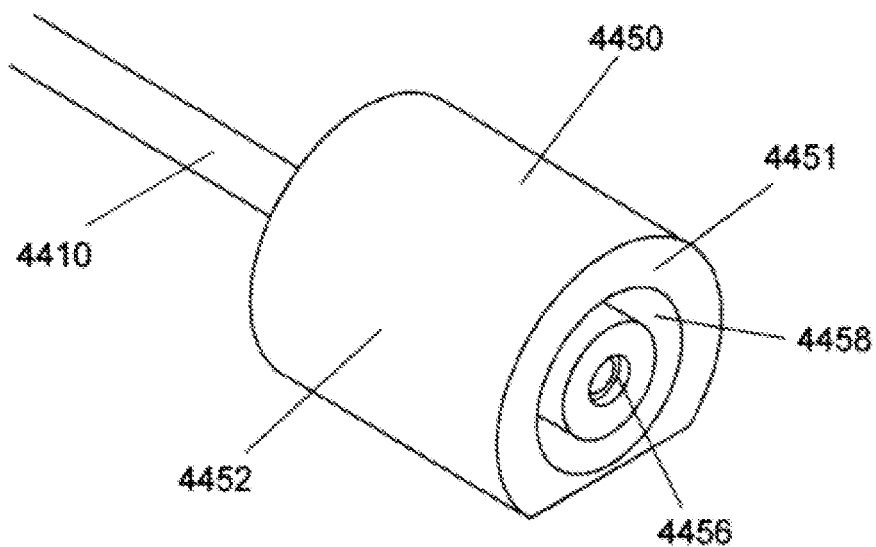
FIG. 69 is a expanded view of the proximal portion of the objects of FIG. 68 at location A.
Figure 70:
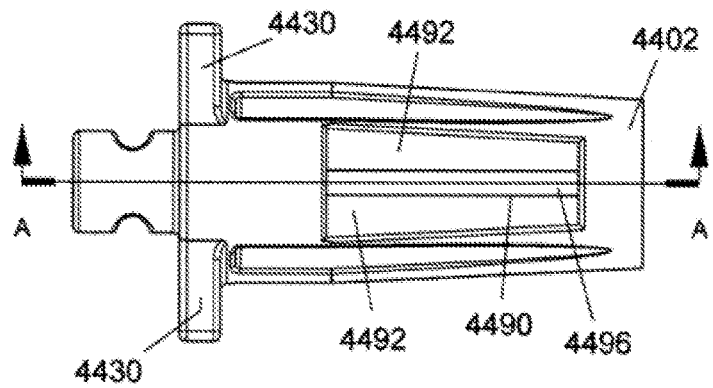
FIG. 70 is a plan view of a handle portion of the tensioning device in an alternate embodiment of an implant placement system contemplated by the present invention.
Figure 71:
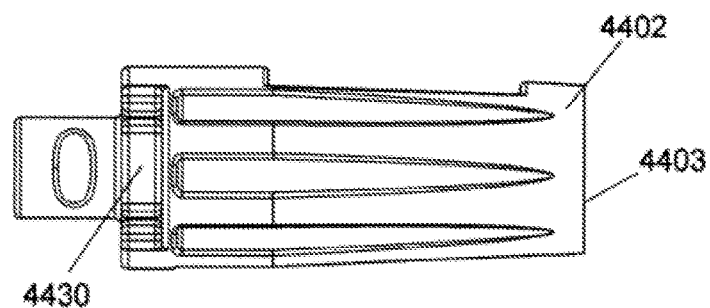
FIG. 71 is a side elevational view of the objects of FIG. 70.
Figure 72:
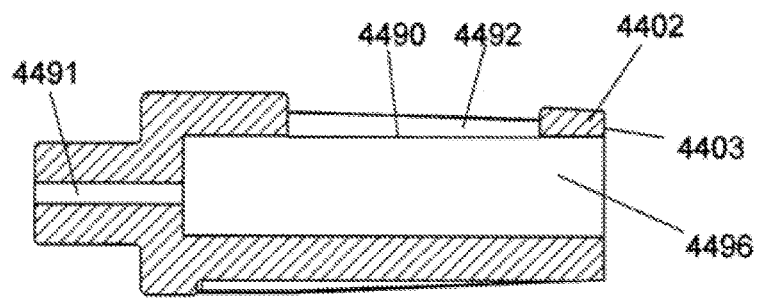
FIG. 72 is a sectional view of the objects of FIG. 70 at location A-A.
Figure 73:
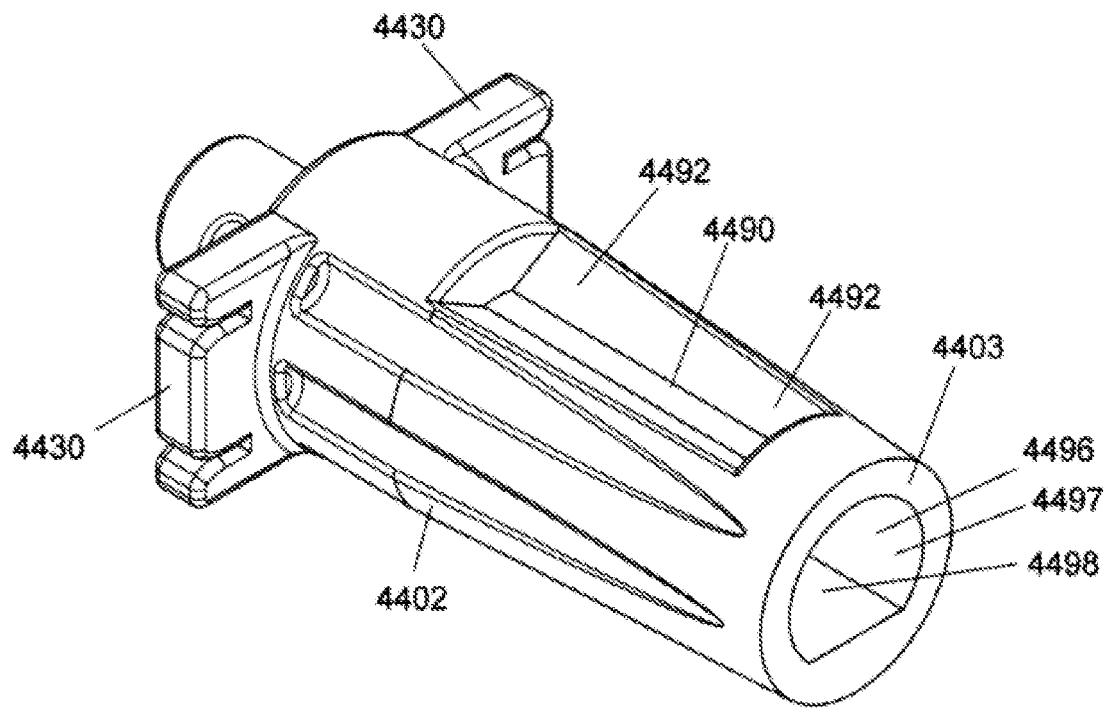
FIG. 73 is a perspective view of the objects of FIG. 70.
Figure 74:
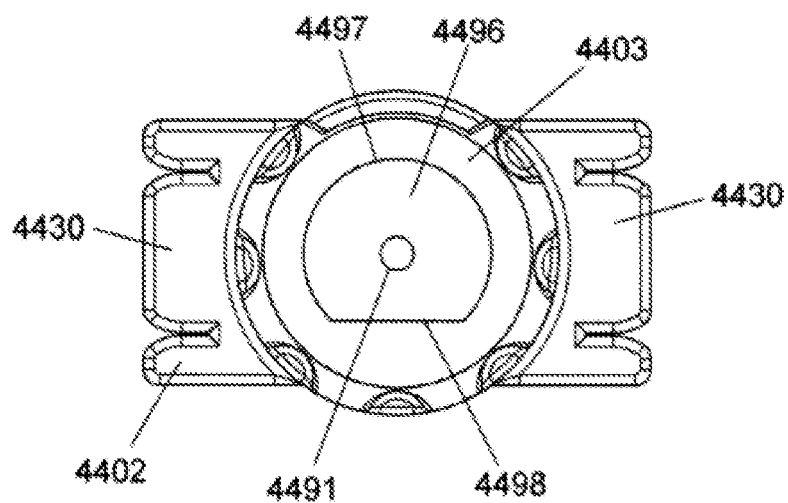
FIG. 74 is an expanded proximal axial view of the objects of FIG. 70.
Figure 75:
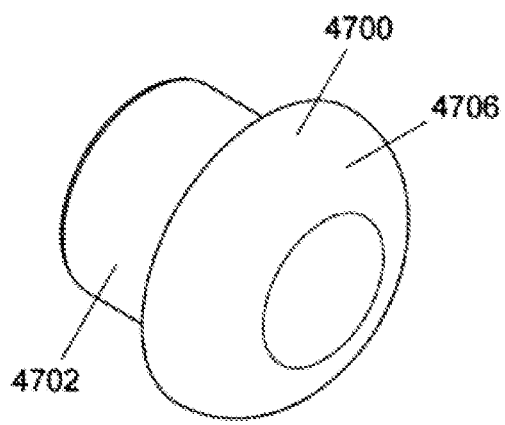
FIG. 75 is a perspective view of an end cap configured for use with the tensioning device in the alternate embodiment of an implant placement system depicted in FIG. 70.
Figure 76:
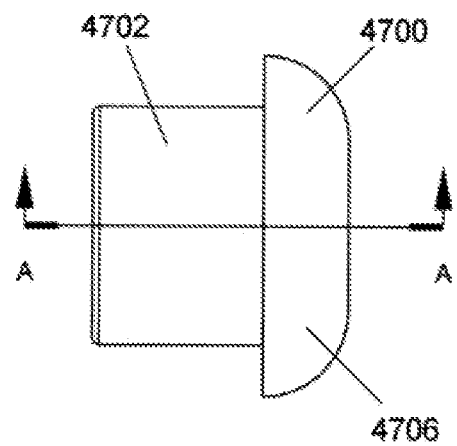
FIG. 76 is a plan view of the objects of FIG. 75.
Figure 77:
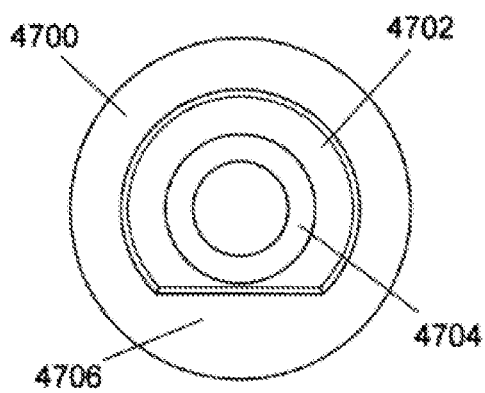
FIG. 77 is a distal axial view of the objects of FIG. 75.
Figure 78:
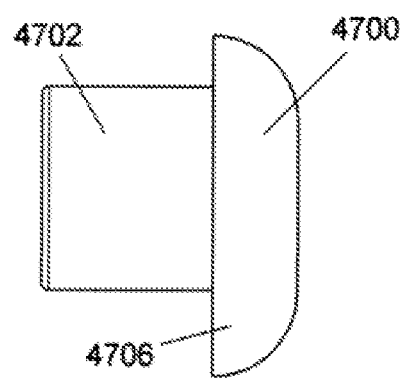
FIG. 78 is a side elevational view of the objects of FIG. 75.
Figure 79:
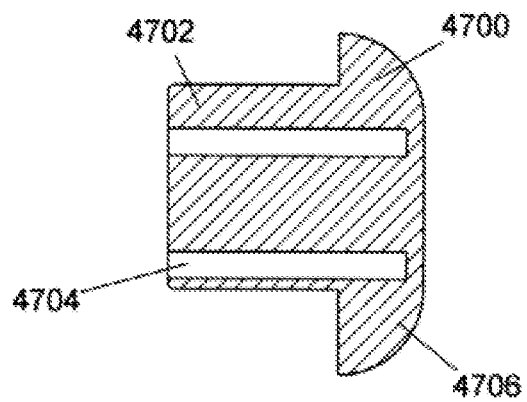
FIG. 79 is a sectional view of the objects of FIG. 76 at location A-A.
Figure 80:
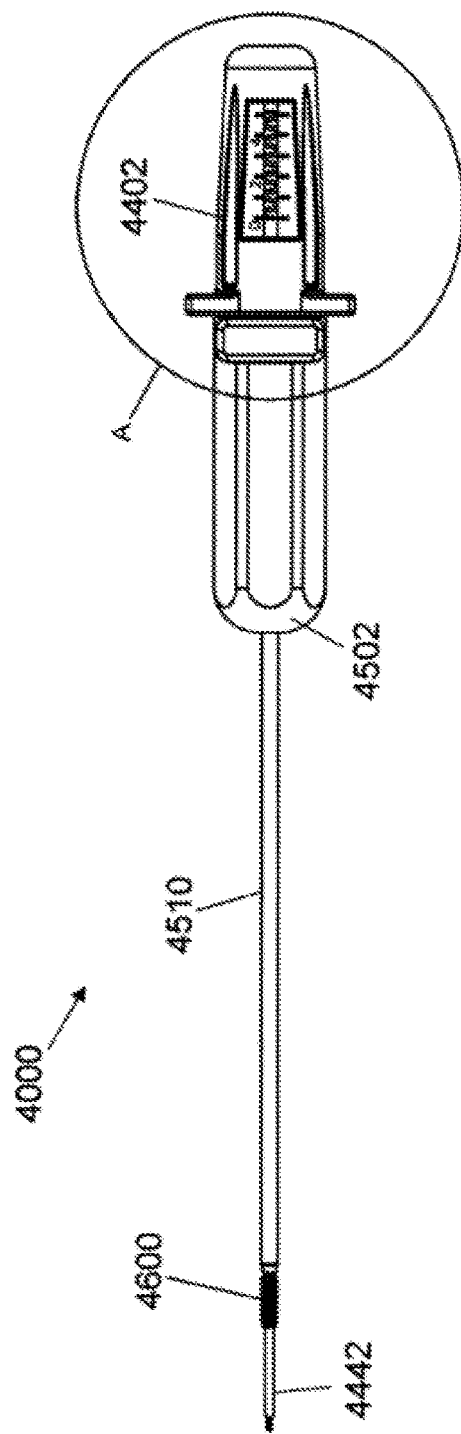
FIG. 80 is a plan view of the assembly of the tensioning device of FIG. 64, the handle portion of FIG. 70, and the cap of FIG. 75 that together form an alternate embodiment of an implant placement system of the present invention that allows the surgeon to measure the tension in the graft during the attachment of the graft in accordance with the methods of the present invention.

FIGS. 58 through 63 depict yet another alternate method for securing a ligament graft to bone using anchor system 2000. As in the previous embodiments, sutures are not used to position and tension the graft 3020 in socket 3032. Rather, as in the previous method, graft 3020 is impaled on the distally extending portions 3444 of distal element 3442 as shown in FIGS. 58 and 59, the sharpened distal ends to of extending portions 3444 penetrating the graft. The site for penetration is selected such that when the ligament is inserted to the bottom of socket 3032 the proximal end of graft 3020 protrudes above the rim of socket 3032. As seen in FIG. 60, graft 3020 is positioned above socket 3032, inserted as shown in FIG. 61, and anchor 3600 placed as shown in FIG. 62. FIG. 63 shows the completed repair. Graft 3020 is trapped between the exterior surface of anchor 3600 and first and second laterally opposed portions of the wall of socket 3032 and retained in position by friction therefrom.

In certain instances, it may be useful to determine the tension in a tendon undergoing a tenodesis procedure so that optimal tension may be selected and maintained based on the particular anatomy. Accordingly, in another embodiment of the present invention, the inner tensioning member may be provided with a mechanism that indicates the force being applied to the graft during insertion into the socket. The insertion site on the graft may be adjusted such that when the graft is inserted to the bottom of the socket the predetermined optimal tension is achieved, and thereafter maintained during anchor placement.

FIGS. 64 through 69 depict a distal assembly 4401 for a force-indicating mechanism for use with an inner tensioning assembly in accordance with the present invention. Elongate tubular element 4410 has at its distal end distal element 4442, identical to distal element 3442 (FIGS. 36 through 40), and at its proximal end element 4450 affixed thereto. Element 4450 has a cylindrical outer surface portion 4452 and a planar outer surface portion 4454. The proximal end of tubular element 4410 is then positioned within lumen 4456. Recess 4458 extends distally from proximal-most surface 4451.

FIGS. 70 to 74 depict a handle 4402 for a force-indicating, inner-tensioning assembly. Handle 4402 is identical to handle 2402 in all aspects except as subsequently described. Specifically, handle 4402 has a distal lumen 4491 with a diameter that allows tubular element 4410 to be slidably positioned therein. Recess 4496 extends distally from proximal-most surface 4403 of handle 4402 and has a cylindrical surface portion 4497 and a planar portion 4498 sized such that element 4450 may be positioned therein. This construction is such that when distal assembly 4401 is assembled to handle 4402 with element 4450 positioned within recess 4496 and tubular member 4410 is positioned within lumen 4491 of handle 4402, distal assembly 4401 may be move axially relative to handle 4402 but rotation is prevented. Handle 4402 has a window 4490 formed in its top surface with adjacent beveled surfaces 4492 so that recess 4496 and elements therein may be viewed.

FIGS. 75 through 79 depict a proximal end cap 4700 for handle 4402. End cap 4700 has a distal portion 4702 with proximally extending recess 4704, and a proximal portion 4706. Distal portion 4702 is configured for assembly to handle 4402.

Figure 81:
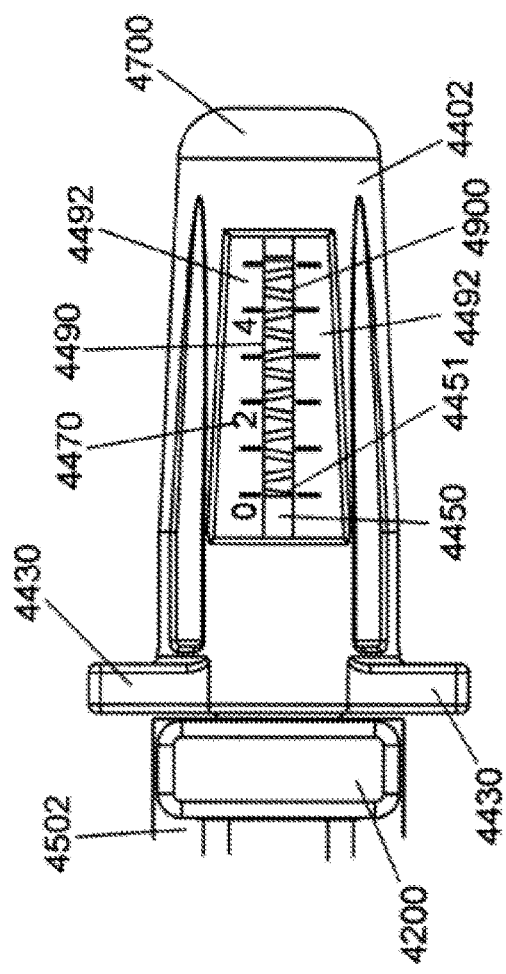
FIG. 81 is an expanded view of the proximal portion of the objects of FIG. 80 at location A.
Figure 82:
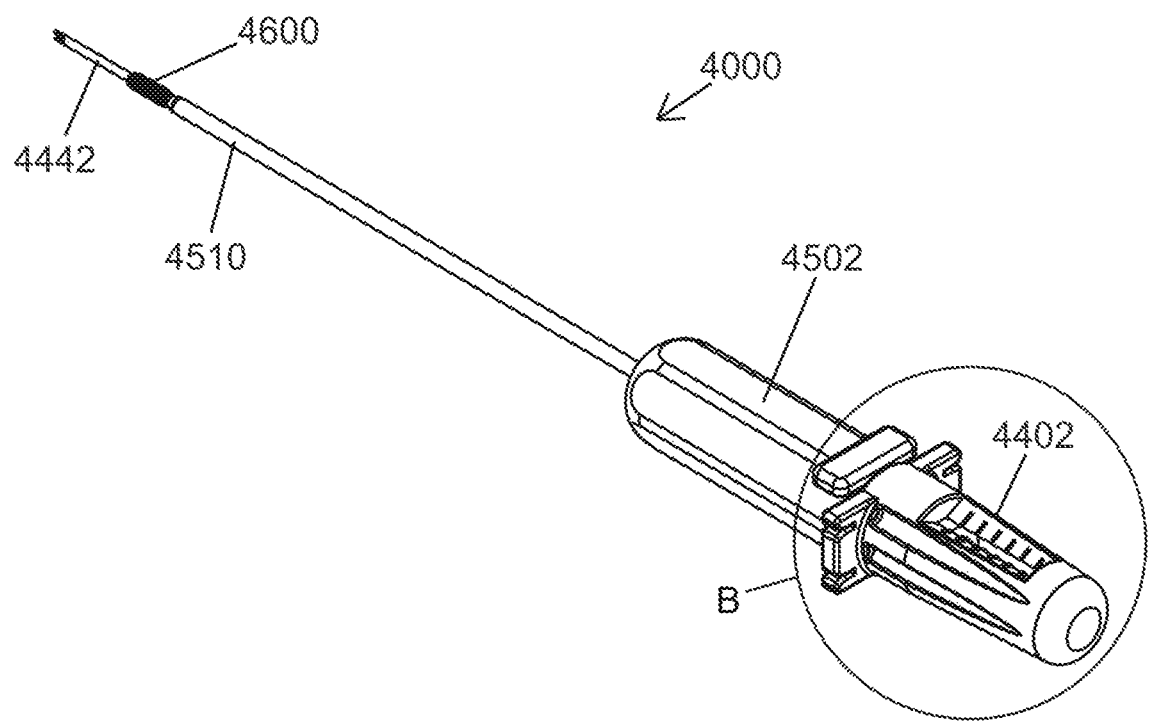
FIG. 82 is a perspective view of the objects of FIG. 80.
Figure 83:
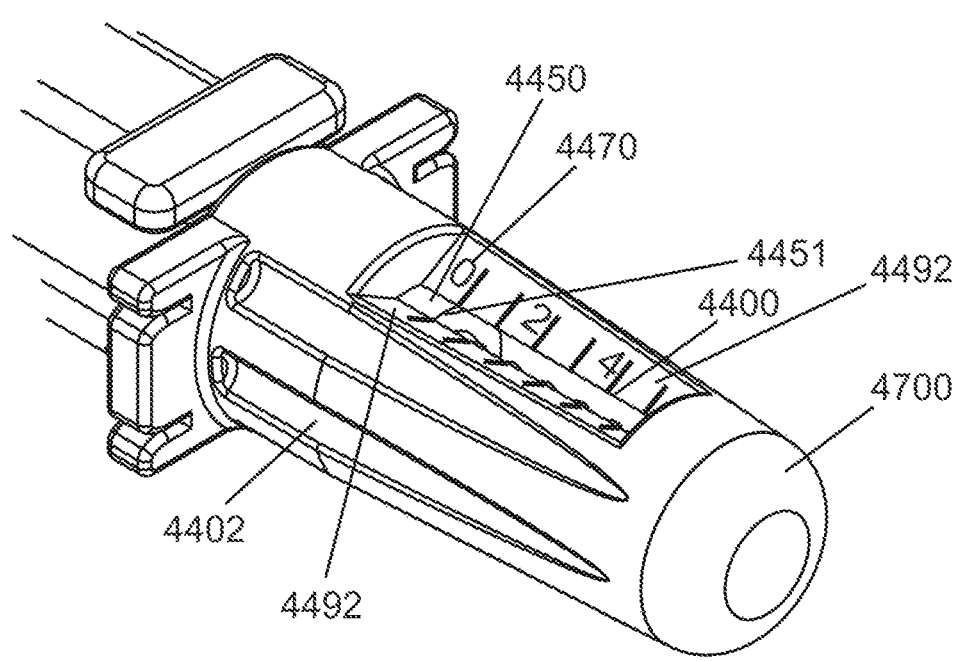
FIG. 83 is an expanded view of the proximal portion of the objects of FIG. 82 at location A.
Figure 84:
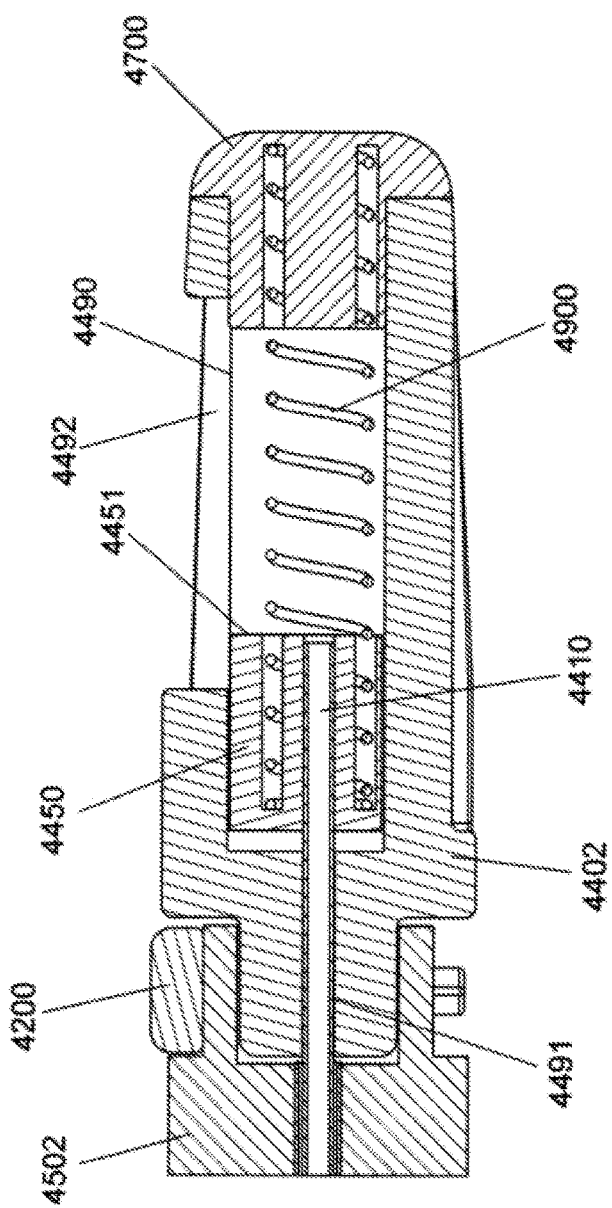
FIG. 84 is a central expanded side elevational sectional view of the objects of FIG. 81.

Referring now to FIGS. 80 through 84, which depict an assembled force-indicating anchor system 4000 of the present invention, distal assembly 4401 may be assembled to handle 4402 as previously described, and end cap 4700 is assembled to the proximal end of handle 4402. Spring 4900 is positioned therebetween with its distal end in recess 4458 of element 4450 and its proximal end in recess 4704 of end cap 4700. As seen in FIG. 81, indicia 4470 are formed on beveled surfaces 4492 such that the position of proximal-most surface 4451 of element 4450 visible through window 4490 may be quantified. The position of element 4450 and its proximal-most surface 4451 is determined by the amount of deflection of spring 4900, which is in turn determined by the force exerted on distal assembly 4401. This force is exerted on distal assembly 4401 by tension in the graft during insertion into a socket by distal element 4442. Device 4000 may be calibrated so that during insertion of the graft into the socket by the surgeon, by observing the position of proximal-most surface 4451 relative to the indicia, will know the insertion force and thereby the tension in the graft.

When using embodiments previously herein described, the inner tensioning device is maintained in a non-rotating condition with respect to the outer driver device by means of the surgeon's hand placed on the proximal hub of the inner tensioning device. The surgeon's hand on the proximal hub also maintains contact between the distal end of the tensioning device and the bottom of the prepared socket by applying distal force to the hub. To advance the outer driver device and the anchor removably mounted thereto into the prepared socket and to place the anchor therein, the surgeon must first uncouple the driver from the tensioning device, then move the driver axially to position the anchor at the socket, and then finally screw the implant into the socket. Since the surgeon must maintain the position of the tensioning device when doing performing any actions with the driver, this method requires the use of both of the surgeon's hands.

However, other embodiments of the present invention contemplate performance of these functions with a single hand. For example, rather than being supplied by the surgeon's hand, the forward force on the tensioning device (or "inner assembly") may alternatively be supplied by an elastic member that is integral with or constitutes a part of the inner assembly. Rotation of the inner tensioning assembly is thus prevented by contact between the distal end of the tensioning device and the bottom surface of the prepared socket in which the implant is to be placed.

FIGS. 85 through 88 depict driver/outer assembly 5500 and implant 5600 for an alternate embodiment implant placement system of the present invention configured for one-handed operation by a surgeon. Driver 5500 and implant 5600 are identical in all aspects of form to driver 1500 and implant 1600 (FIGS. 1 through 2B) except as hereafter specifically described. For example, off-axis holes 1506 of handle 1502 of driver 1500 are eliminated, as are the planar regions in which they intersect. Proximal cylindrical recess 5504 extends distally to intersect vertical cylindrical recess 5534 which is configured to receive a slidable control element, the upper portion of vertical recess 5534 being configured to receive retainer 5530 with coaxial opening 5532.

Inner assembly 5400, depicted in FIGS. 89 through 91B, is identical in form to tensioning device/inner assembly 1400 depicted in FIGS. 3 through 8 except as specifically hereafter described. For example, the distal cylindrical portion 1404 with off-axis lateral grooves 1406 of hub 1402 of tensioning device 1400 is eliminated. In its stead, inner tensioning assembly 5400 has distally adjacent to hub 5402, assembly 5450 formed of proximal element 5452 and distal element 5458 with spring 5454 positioned therebetween as depicted in FIG. 91A. Proximal element 5452 and distal element 5458 are rotatably and slidably positioned on tubular middle portion 5410. Positioned distal to distal element 5458 and separated therefrom by washer 5462 (FIG. 91B), element 5456 is affixed to tubular middle portion 5410. Element 5456 has a proximal portion 5476, a middle portion 5470 of reduced diameter forming a circumferential channel bounded by proximal wall 5466 and distal wall 5468, and a distal portion 5472 having a distal end on which is formed chamfer 5474.

Figure 93:
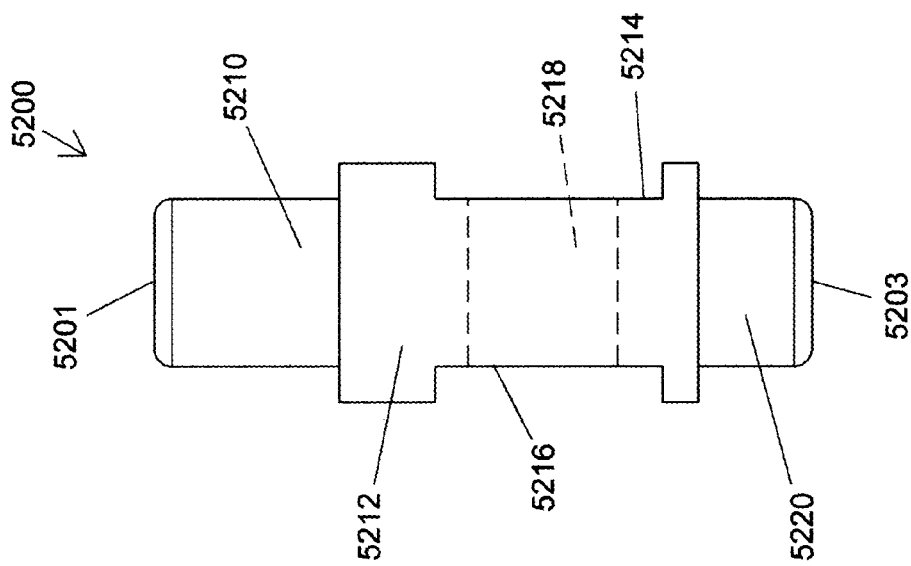
FIG. 93 is a side elevational view of the control element of FIG. 92.
Figure 92:
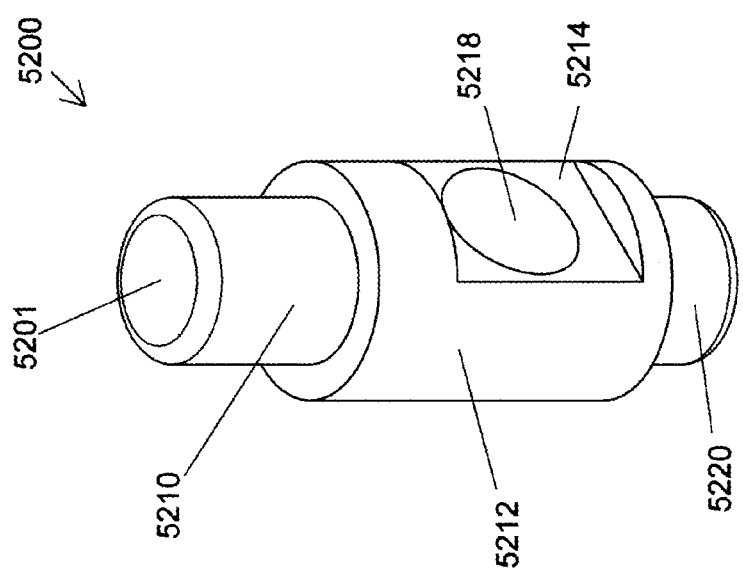
FIG. 92 is a perspective view of a control element for an alternate embodiment of an implant placement system of the present invention.

FIGS. 92 and 93 depict a slidable control element 5200 configured to be slidably received within vertical cylindrical recess 5534 of handle 5502 of driver 5500, and retained therein by retainer 5530. Control element 5200 has an upper portion 5210 sized to be slidably received within opening 5532 of retainer 5530, a mid portion 5212 and a lower portion 5220. Mid portion 5212 has formed therein symmetrically opposed first (distal) flat 5216 and second (proximal) flat 5214 with cylindrical hole 5218 extending therebetween.

Figure 94:
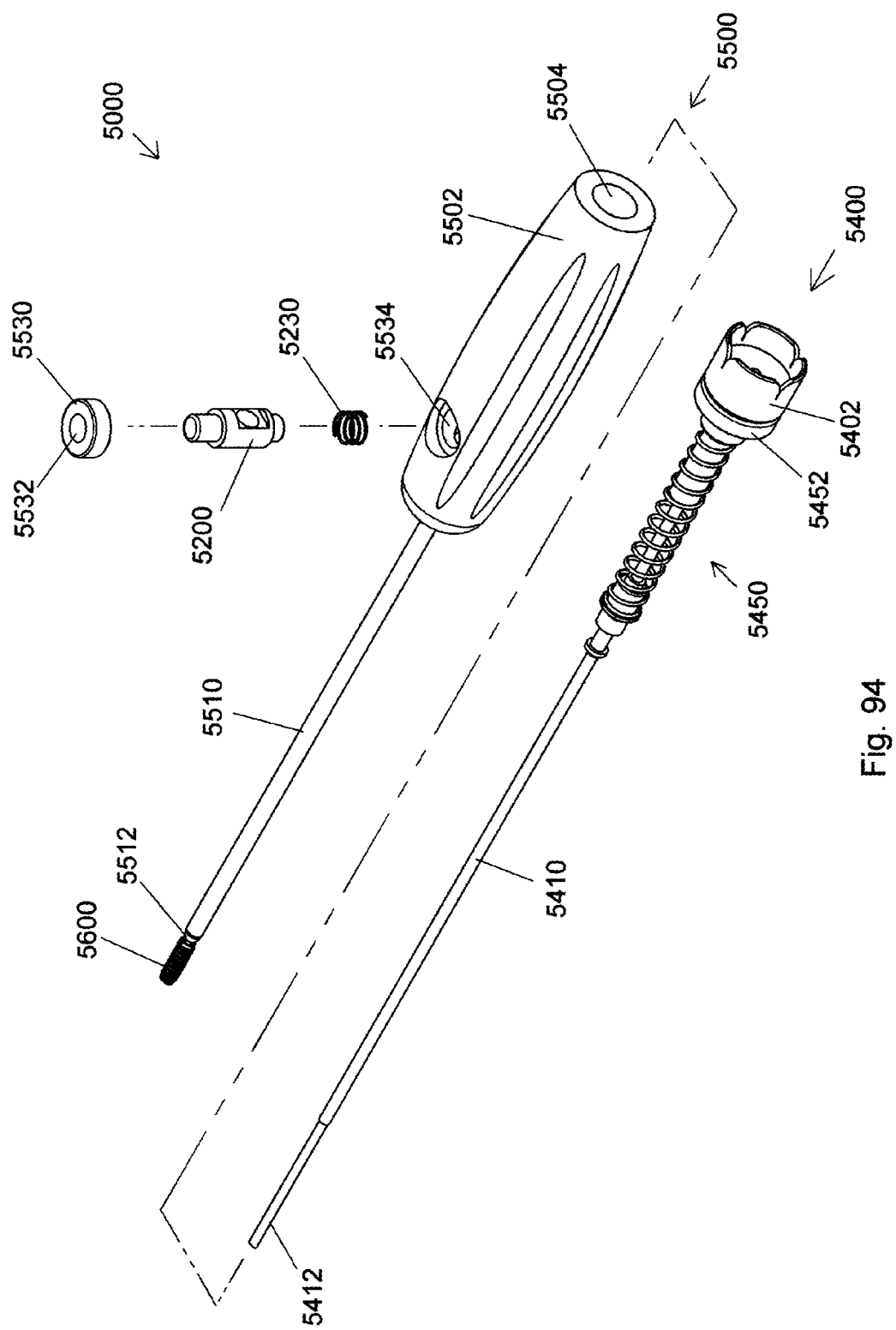
FIG. 94 is a perspective view of an exploded assembly of the outer driver assembly of FIG. 85, the inner tensioning assembly of FIG. 89 and the control element of FIG. 92 that together form an alternate embodiment of an implant placement system in accordance with the present invention.
Figure 95:
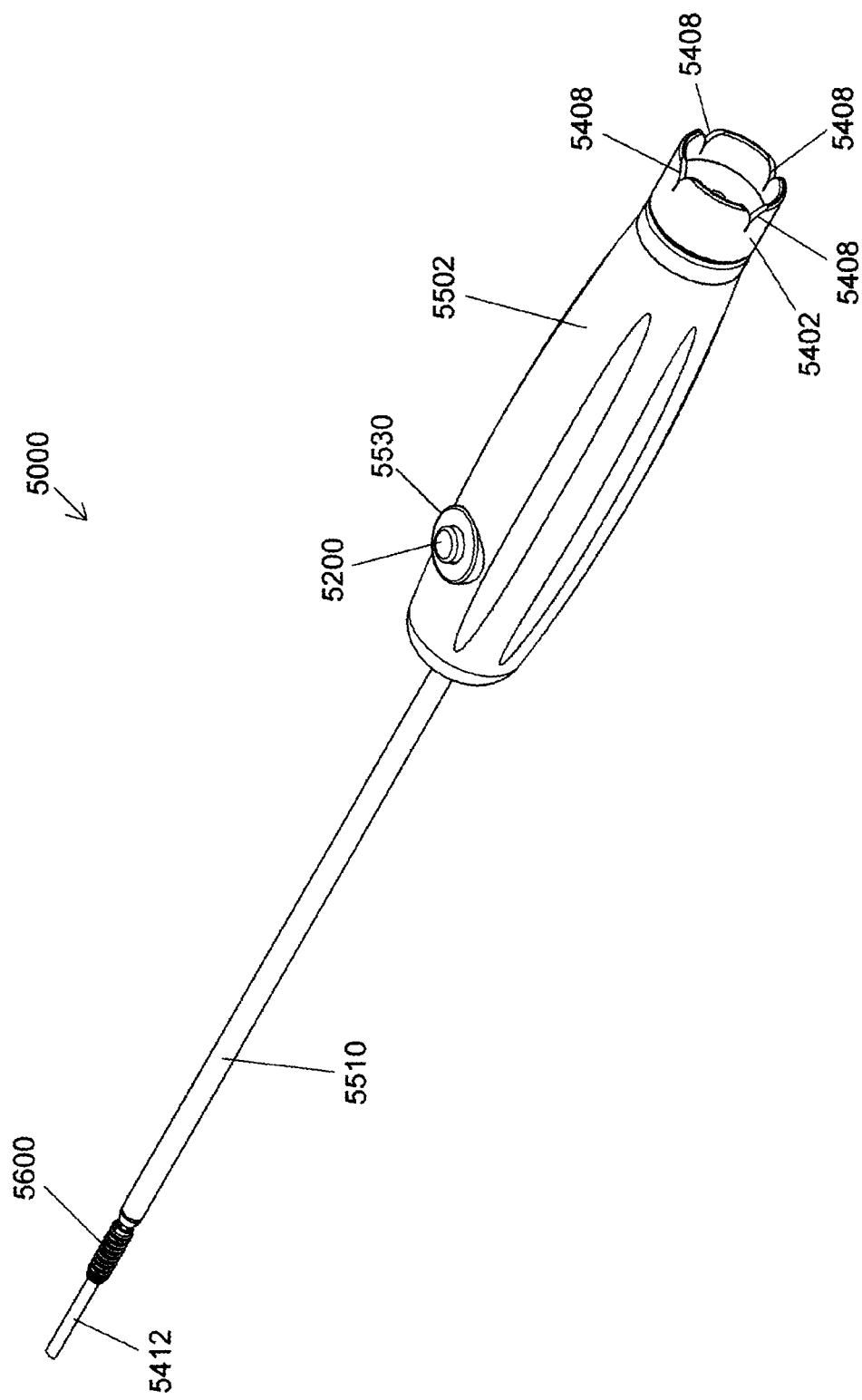
FIG. 95 is a perspective view of an alternate embodiment of an implant placement system in accordance with the present invention that is formed of the assembled elements of FIG. 94, with the distal portion of the inner tensioning assembly protruding beyond the implant in preparation for implant placement.
Figure 96:
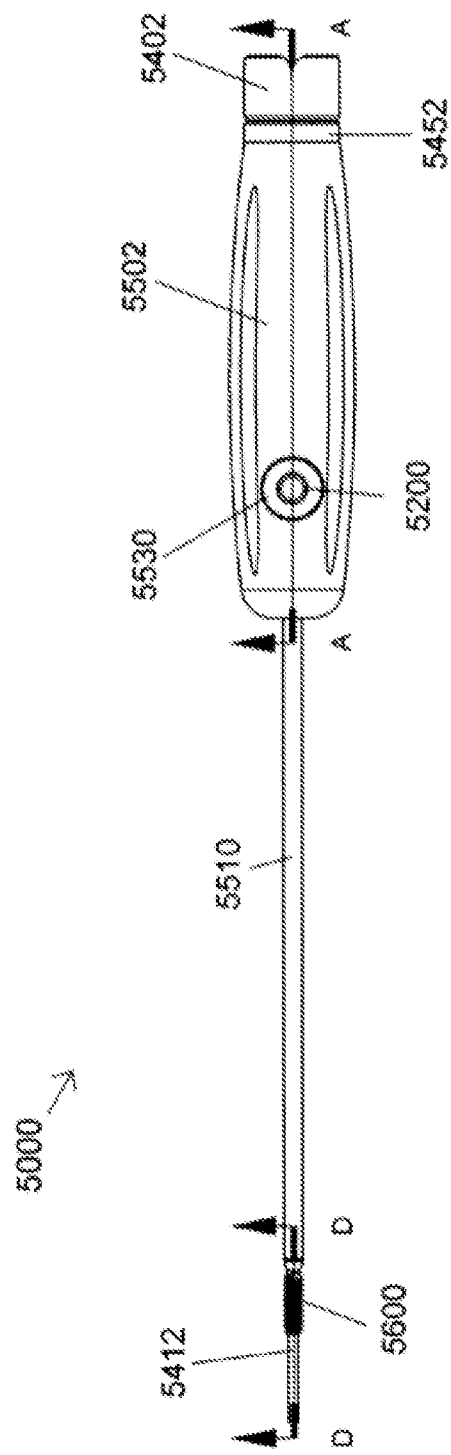
FIG. 96 is a plan view of the objects of FIG. 95.
Figure 97:
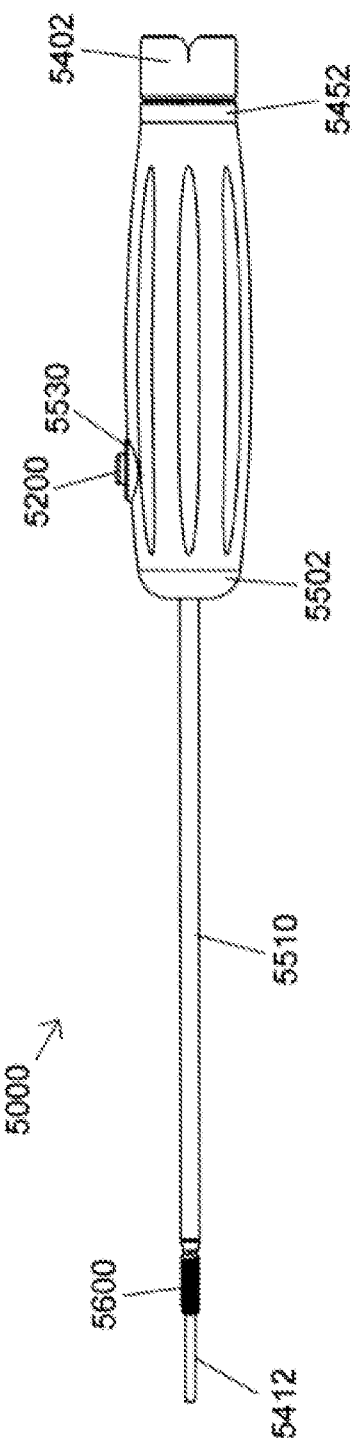
FIG. 97 is a side elevational view of the elements of FIG. 95.
Figure 98A:
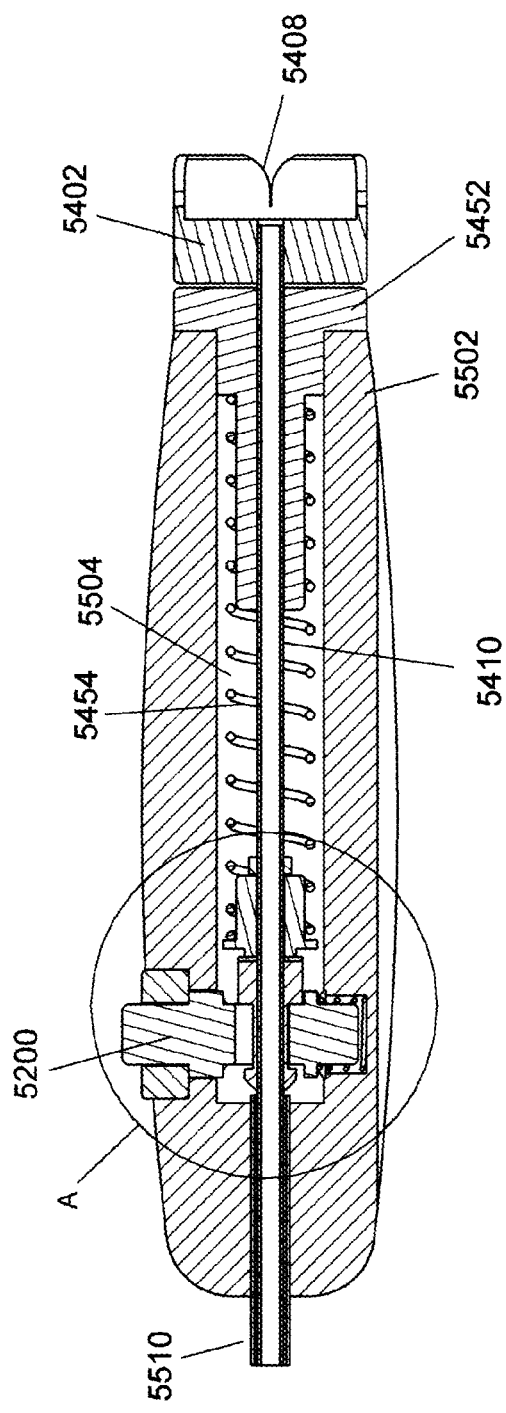
FIG. 98A is an expanded sectional view of the objects of FIG. 96 at location A-A.
Figure 99:
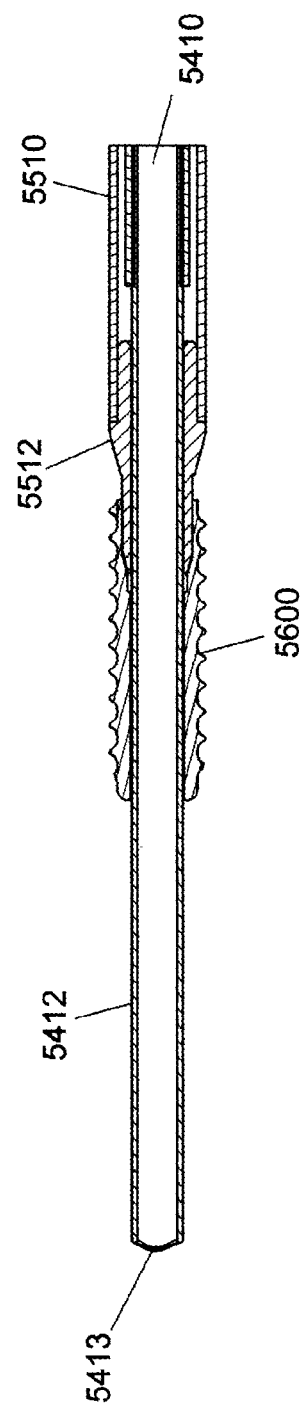
FIG. 99 is an expanded sectional view of the objects of FIG. 96 at location D-D.
Figure 100:
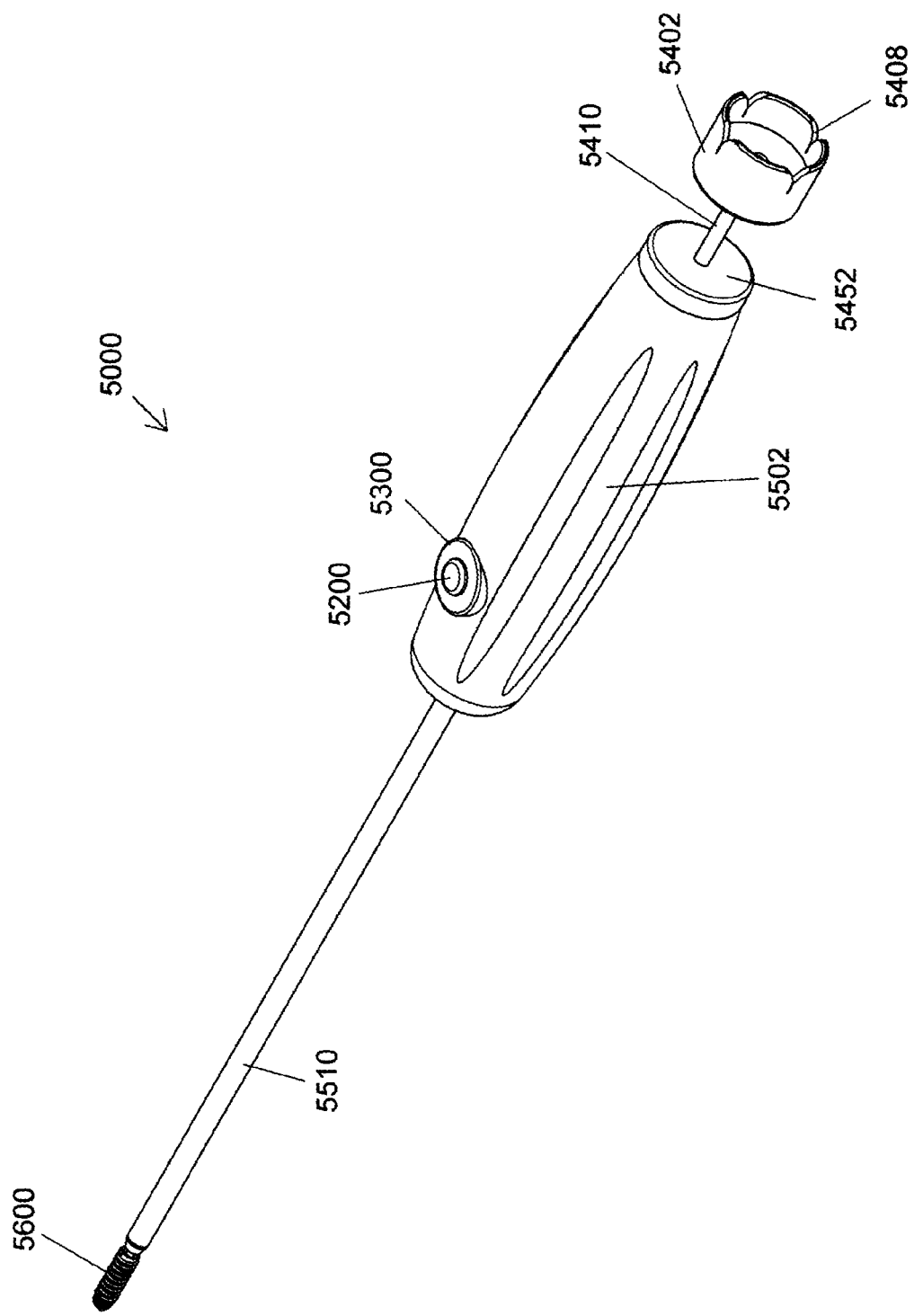
FIG. 100 is a perspective view of the implant placement system of FIG. 95 with the outer driver assembly and implant advanced distally as when the implant is fully placed in a socket.
Figure 101:
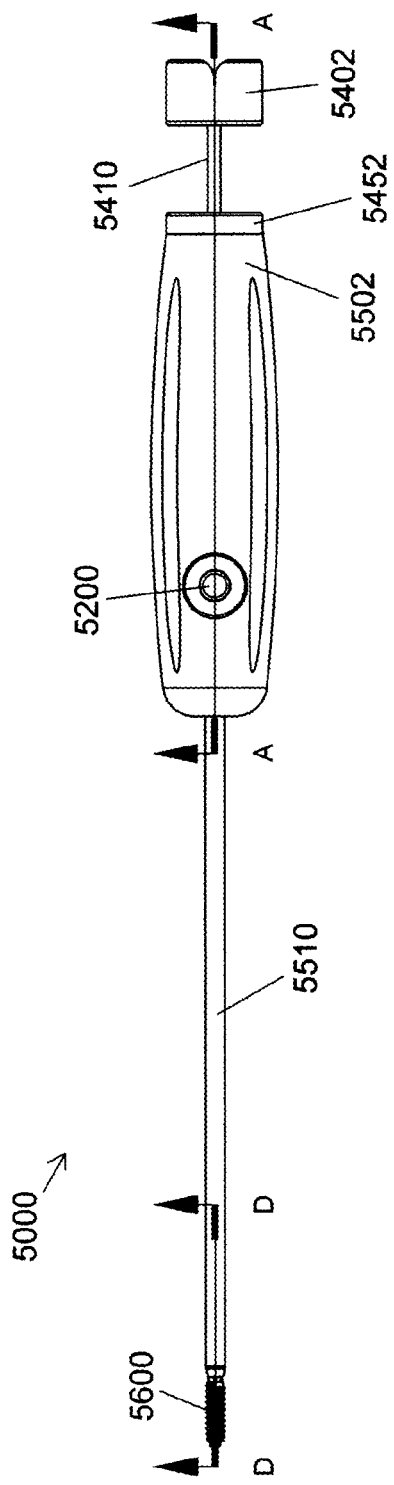
FIG. 101 is a plan view of the objects of FIG. 100.
Figure 102:
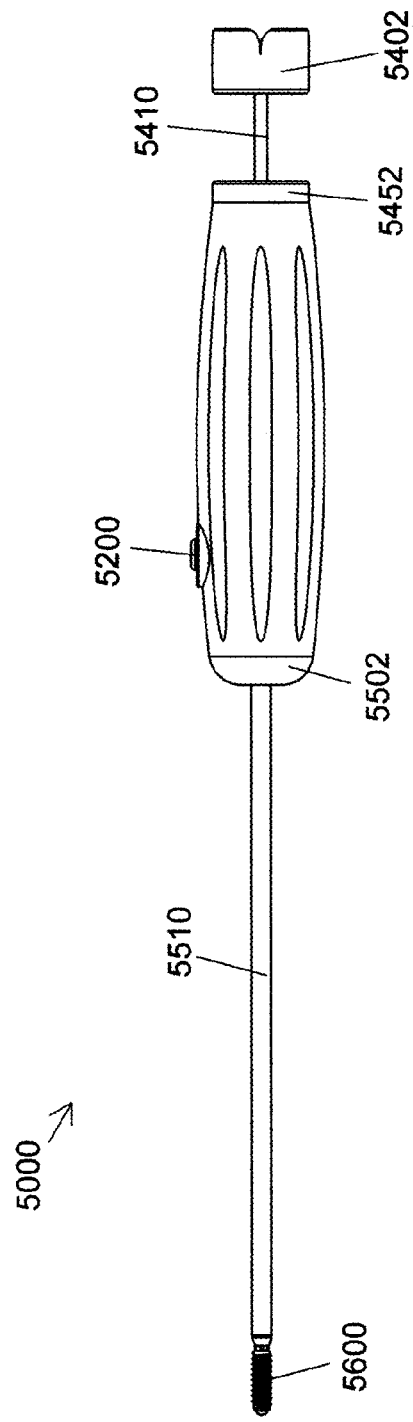
FIG. 102 is a side elevational view of the objects of FIG. 100.

The elements of this alternate embodiment implant placement system 5000 of the present invention comprising outer driver assembly 5500, inner tensioning assembly 5400, and control element 5200 are depicted in FIG. 94. Slidable control element 5200 with spring 5230 is inserted into vertical cylindrical recess 5534 and retained therein by retainer 5530. Inner assembly 5400 is inserted into proximal cylindrical recess 5504 and proximal element 5452 is affixed to the proximal end of handle 5502.

FIGS. 95 through 99 depict implant placement system 5000 assembled and ready for use. Proximal element 5452 of inner assembly 5450 (see FIG. 94) is affixed to the proximal end of outer driver assembly 5500 handle 5502. Control element 5210 is depicted in a first position wherein upper portion 5210 of control element 5200 protrudes above the top surface of retainer 5530 and is maintained in that position by spring 5230. In this first position, distal travel of outer driver assembly 5500 relative to inner tensioning assembly 5400 is constrained by contact between distal facing surface 5466 of proximal portion 5476 of element 5456 and proximal surface 5214 of control element 5210, and initial compression being imparted to spring 5454 thereby. Distal element 5412 of inner tensioning assembly 5400 protrudes beyond implant 5600 a sufficient distance to reach to bottom of a prepared socket while implant 5600 remains proximal to the socket. As depicted in FIGS. 98A through 98C, when a proximal force is applied to distal element 5412 of inner assembly 5400 as when tensioning sutures for implant placement, proximal motion of inner tensioning assembly 5400 relative to outer driver assembly 5500 is prevented by contact between proximal surface 5468 of distal portion 5472 of element 5456 affixed to tubular middle portion 5410, and distal surface 5216 of control element 5210.

Figure 103:
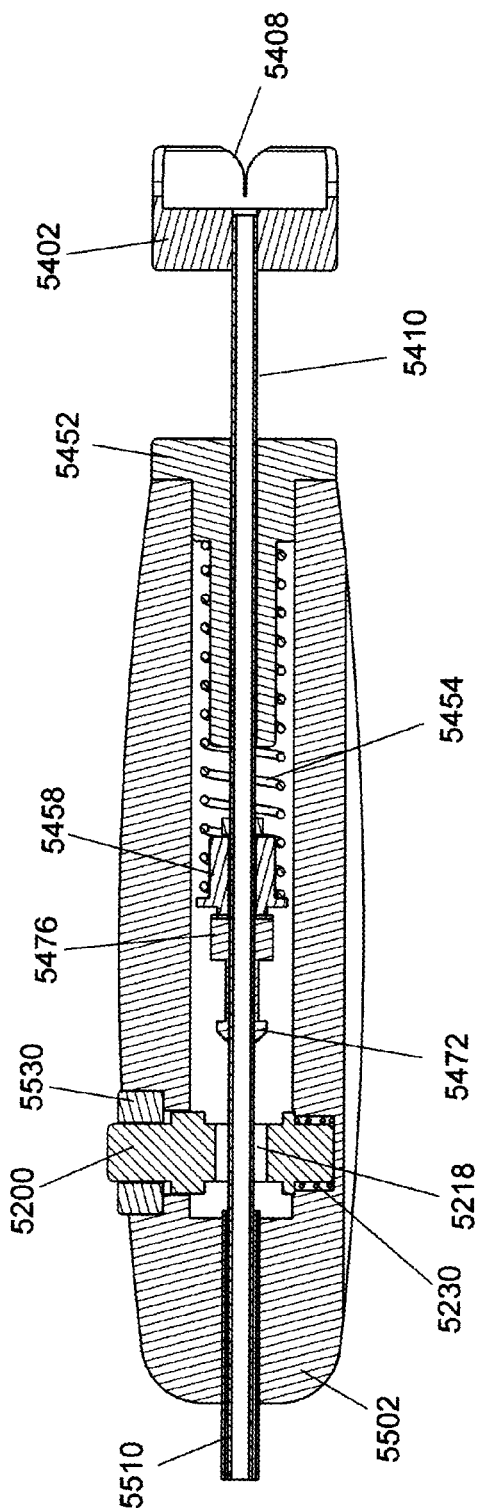
FIG. 103 is an expanded sectional view of the objects of FIG. 101 at location A-A.
Figure 104:
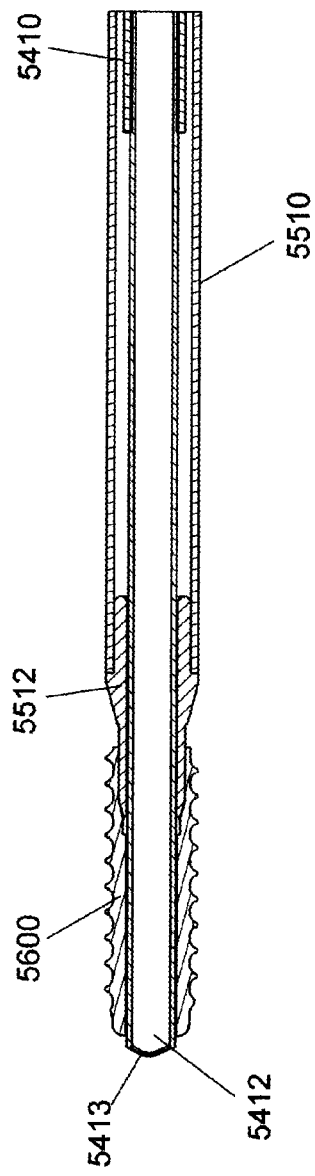
FIG. 104 is an expanded sectional view of the objects of FIG. 101 at location D-D.

Applying a downward force to slide control 5200 sufficient to compress spring 5230 brings opening 5218 in slide control mid portion 5212 into coaxial alignment with tubular mid portion 5410 and element 5456 mounted thereto such that distal portion 5472 of element 5456 may pass therethrough allowing outer driver assembly 5500 to advance distally relative to inner tensioning assembly 5400 to its distal limit as depicted in FIGS. 100 through 104. Spring 5454 is compressed as depicted in FIG. 103. When slide 5200 is positioned as shown, outer driver assembly 5500 may be advanced distally with resistance to this axial movement provided by force supplied by spring 5454. Outer driver assembly 5500 may also be simultaneously freely rotated relative to inner tensioning assembly 5400. Referring to FIGS. 98B and 98C, distal element 5458, washer 5462 and proximal portion 5476 of element 5456 together form a bearing, distal element 5456 and washer 5462 being formed of a metallic material and optionally having a suitable lubricant applied to their mating surfaces as well as on tubular mid portion 5410 of inner tensioning assembly 5400.

Implant placement system 5000 places implant 5600 in the same manner as system 1000 in that sutures passing through the graft are tensioned using a non-rotating distal tensioning element that protrudes distally beyond the implant a sufficient distance to allow the distal end of the distal tensioning element to reach the bottom of a prepared socket with the implant remaining proximal to the socket. Unlike system 1000, in which rotation of inner tensioning assembly 1400 is prevented by the surgeon's control of hub 1402, prevention of rotation of inner tensioning assembly 5400 is prevented by cooperative interaction between the distal end 5413 of distal element 5412 of inner tensioning member 5400 and the cortical bone at the bottom of the socket. The consistency of the cortical bone at the bottom of a socket is such that it may be deformed by distal end 5413 of distal element 5412 and by sutures passing into the cannulation of distal element 5412 due to axial force applied by the surgeon. This deformation increases the frictional resistance to rotation of distal element 5412 and inner tensioning assembly 5400 of which it is a part. This resistance to rotation may be further enhanced through the forming of suitable contours on distal end 5413 of distal element 5412 so as to create features that may penetrate the cortical bone or create localized depressions therein. These contours may include, for instance, protuberances, grooves, or curvilinear shapes. Like implant system 1000, system 5000 has cleats 5408 formed in inner tensioning assembly hub 5402 for maintaining the tension on sutures during placement of the implant. In other embodiments, cleats 5408 are not formed in hub 5402 and the suture tension is maintained through friction between the cortical bone at the bottom of the socket and distal end 5413 of distal tensioning element 5412 between which it is trapped.

When placing anchor 5600, the surgeon does not control inner tensioning assembly 5400 through hub 5402, but rather controls placement process exclusively through handle portion 5502 of outer driver assembly 5500 and slide control 5320.

When using implant placement system 5000, suture is loaded into tensioning inner assembly 5400 as depicted in FIGS. 20 and 21 for implant system 1000. Thereafter, anchor 5600 is placed as depicted in FIGS. 22, 25, 28, 31 and 32. In figures referenced in the following description, depicted elements of implant system 1000 designated as "1XXX" may be replaced by their corresponding elements of implant system 5000 designated as "5XXX". FIG. 22 schematically depicts a socket 32 formed by drilling or punching in bone 30, and a graft 20 to be affixed to bone 30. Sutures 1800 are passed through graft 20 in a usual manner; and the sutures loaded into system 5000 as previously described and depicted in FIGS. 20 and 21, such that the suture proximal ends are accessible to the surgeon. Subsequently, distal tubular portion 5412 of tensioning inner assembly 5400 is inserted into socket 32 as depicted in FIGS. 23 through 25, the distal end of tubular portion 5412 contacting the bottom surface of socket 32. Thereafter, referring to FIGS. 26 through 28, the surgeon grasps the proximal ends of sutures 1800 and withdraws them proximally so as to advance graft 20 towards socket 32. When graft 20 is in the desired position, the proximal ends of sutures 1800 are secured in cleats 5408 (FIG. 95) to maintain the graft position. So long as the proximal ends of sutures 1800 remain securely cleated and the distal end of tubular element 5412 is maintained in contact with the bottom of socket 32, the position of graft 20 will not change. The surgeon may adjust sutures 1800 as required to achieve optimal placement of graft 20. When this optimal placement of graft 20 has been achieved, while applying distal force to handle 5502 of implant system 5000 so as to maintain contact between the distal end off distal tubular element 5412 and the bottom of socket 32, the surgeon moves slide control 5300 to its second position (see FIG. 103) thereby allowing outer driver assembly 5500 with implant 5600 mounted thereto to be moved distally so as to bring implant 5600 to socket 32, and to be rotated so as to then thread implant 5600 into socket 32 so as to trap sutures 1800 between anchor 5600 and the wall of socket 32 in bone 30 as depicted in FIG. 31. When anchor 5600 is fully inserted in socket 32, the proximal ends of sutures 1800 are then released from cleats 5408 and system 5000 is withdrawn from the joint, leaving the repair site as depicted in FIG. 32. Subsequently sutures 1800 are trimmed adjacent to anchor 5600 and the anchor placement is complete. Upon withdrawal of implant placement system 5000 from the site, outer driver assembly 5500 is returned to its proximal position (FIGS. 95 through 99) by force supplied by spring 5454, chamfered end 5474 of distal portion 5472 of element 5456 and opening 5218 cooperatively acting to return control slide 5200 to its first position.

The initial compression applied to spring 5454 when assembled as shown in FIGS. 95 through 99, with outer driver assembly 5500 in its proximal-most position, is sufficient to ensure that, after tensioning sutures 1800 in socket 32 prior to placing implant 5600, when slide control 5320 is moved to its second position to allow outer driver assembly 5500 to move distally to bring the implant to the socket and to screw the implant into the socket, distal end 5413 of distal tensioning element 5412 remains firmly in contact with the cortical bone at the bottom of socket 32 so as to prevent rotation of inner tensioning assembly 5400.

In the method of implant placement previously described using placement system 5000, the tension in sutures 1800 and graft position are maintained by removably storing the suture proximal ends in cleats 5408 of inner tensioning assembly 5400. In an alternate method for placing anchor 5000, the tension in sutures 1800 and graft position are maintained by the surgeon applying tension to the proximal ends of sutures 1800, or by friction force applied to the portions of sutures 1800 trapped between distal end 5413 of distal tensioning element 5412 and the cortical bone at the bottom of socket 32, or by a combination of these two methods.

In an alternate embodiment, a loop of an elongate element such as, for instance, nitinol wire may be formed distal to the distal end 5413 of distal tensioning element 5412 (see FIG. 99) with the proximal ends of the elongate element removably secured in cleats 5408 of hub 5402. Sutures may be loaded into the nitinol loop, tensioned, and secured by an anchor, whereupon the elongate element is removed. This method of implant placement is described in detail in inventors' own U.S. Pat. No. 9,770,240 referenced above, entitled "Ceramic Implant Placement Systems And Superelastic Suture Retention Loops For Use Therewith", the contents of which have been previously incorporated by reference in their entirety.

Figure 105:
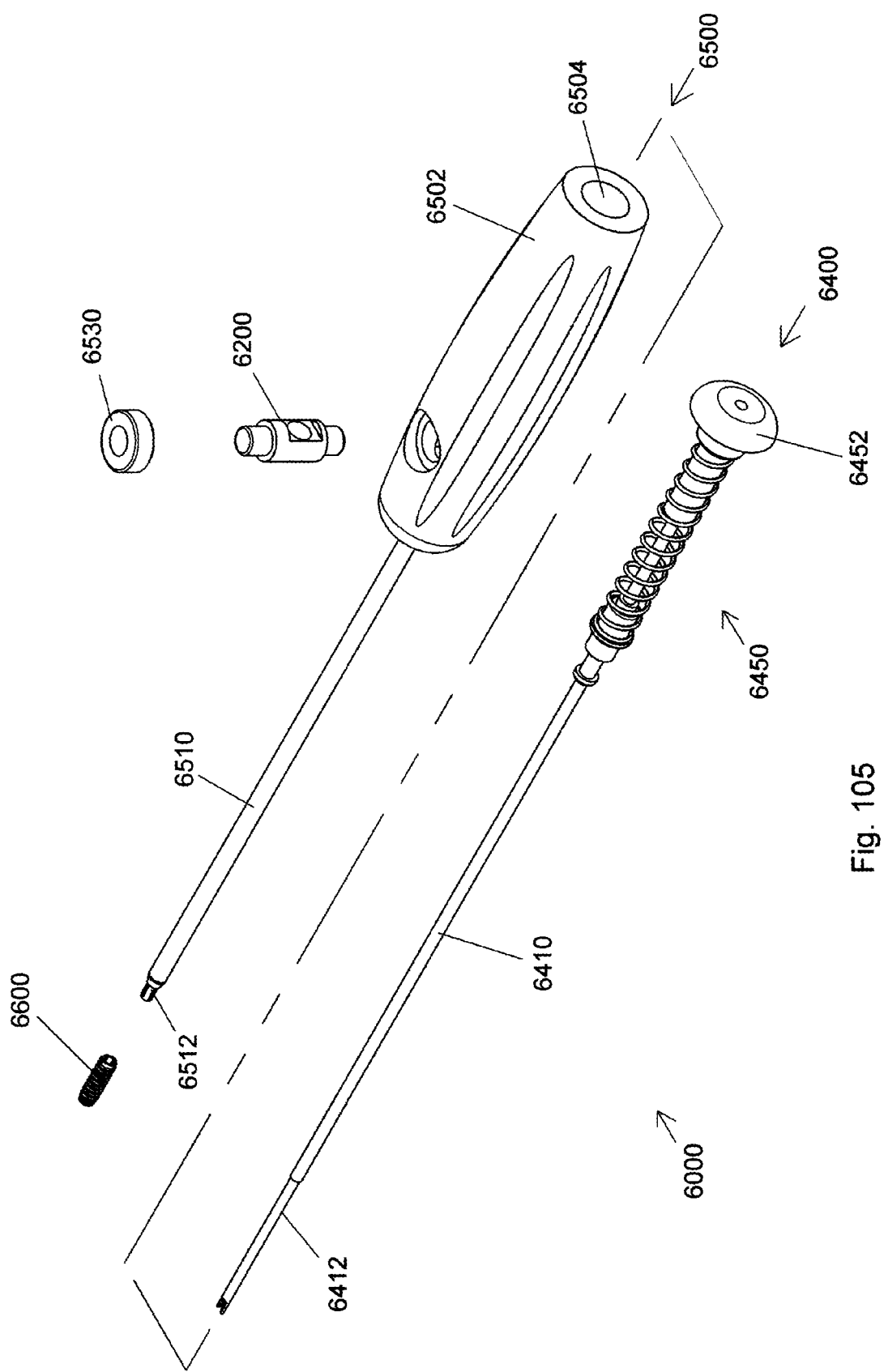
FIG. 105 is a perspective view of the exploded assembly of an alternate embodiment of an implant placement system in accordance with the present invention.
Figure 106A:
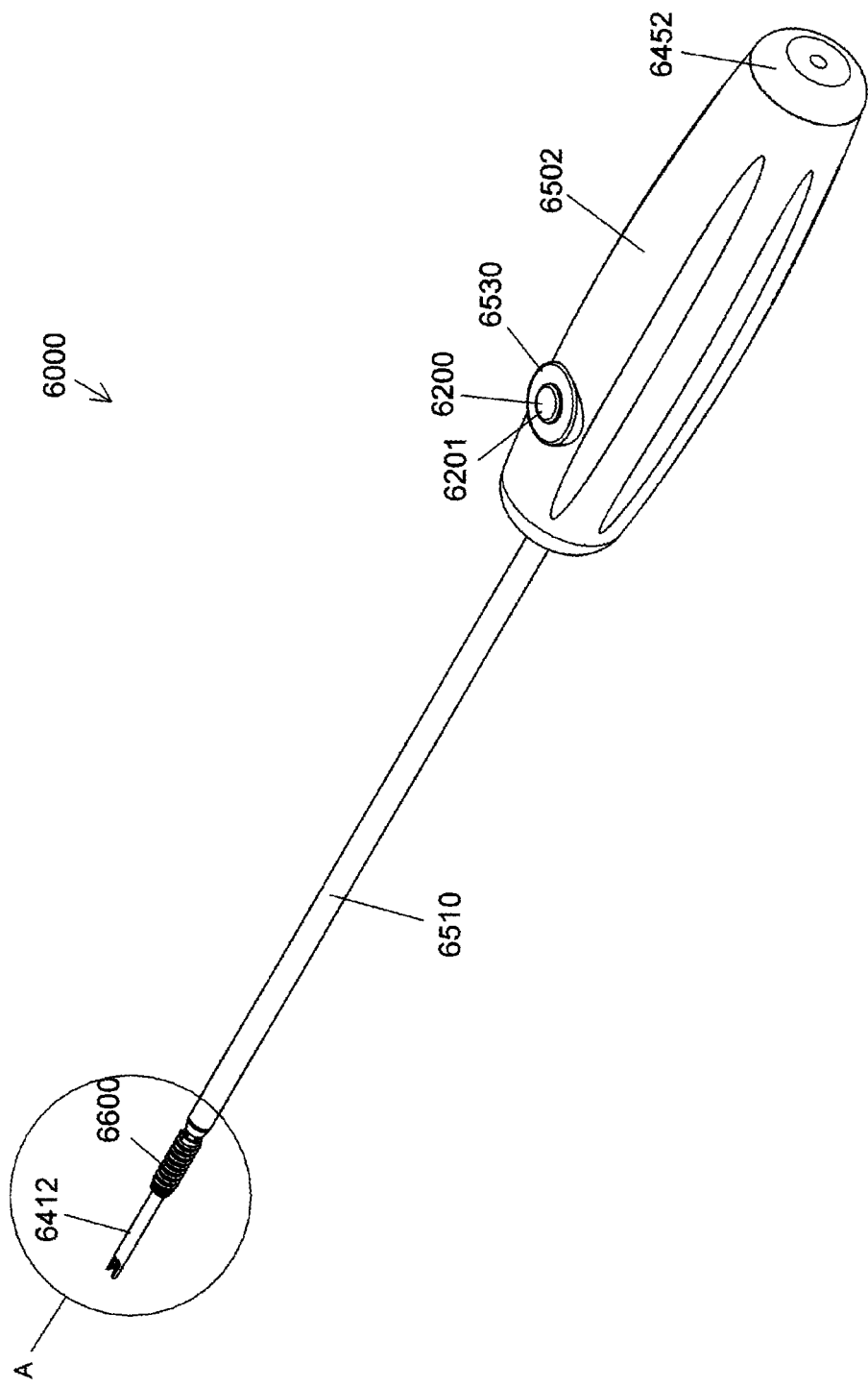
FIG. 106A is a perspective view of an alternate embodiment of an implant placement system of the present invention that is formed of the elements and assemblies of FIG. 105, with the distal portion of the inner tensioning assembly extended beyond the implant in preparation for implant placement.
Figure 106B:
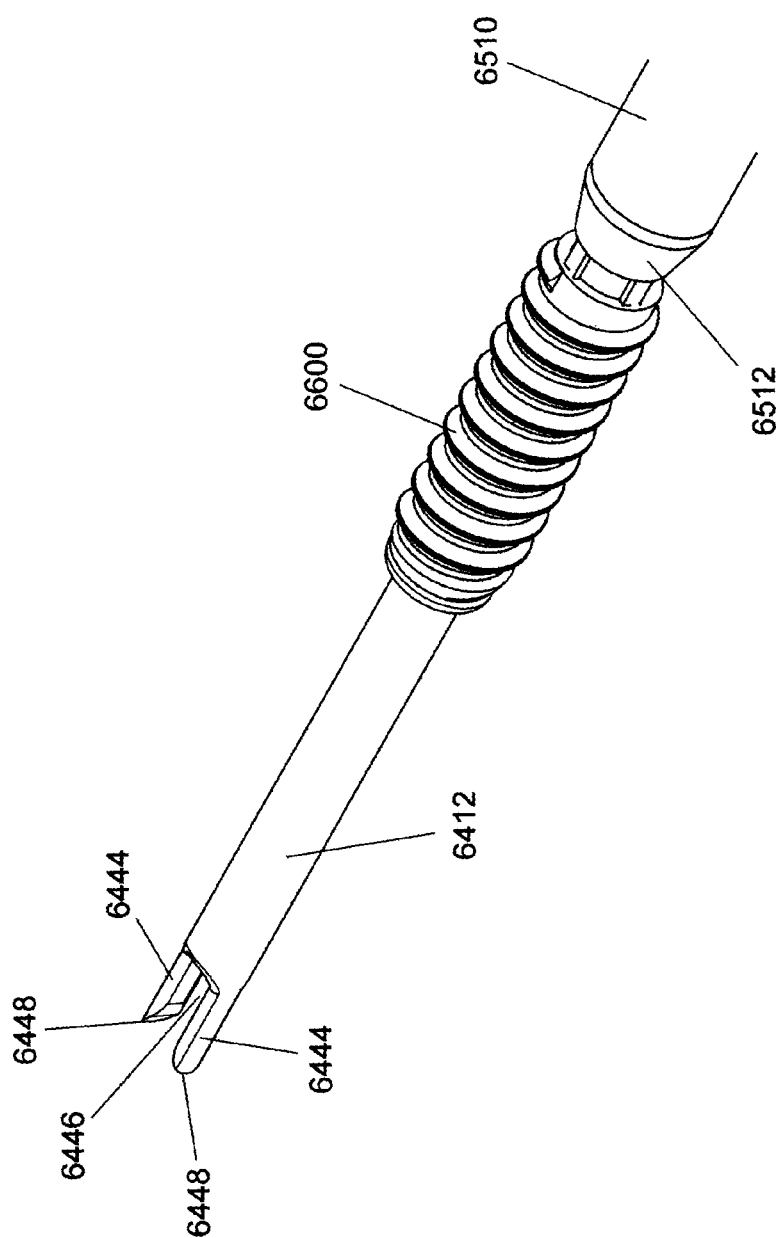
FIG. 106B is an expanded view of the objects of FIG. 106A at location A.
Figure 111:
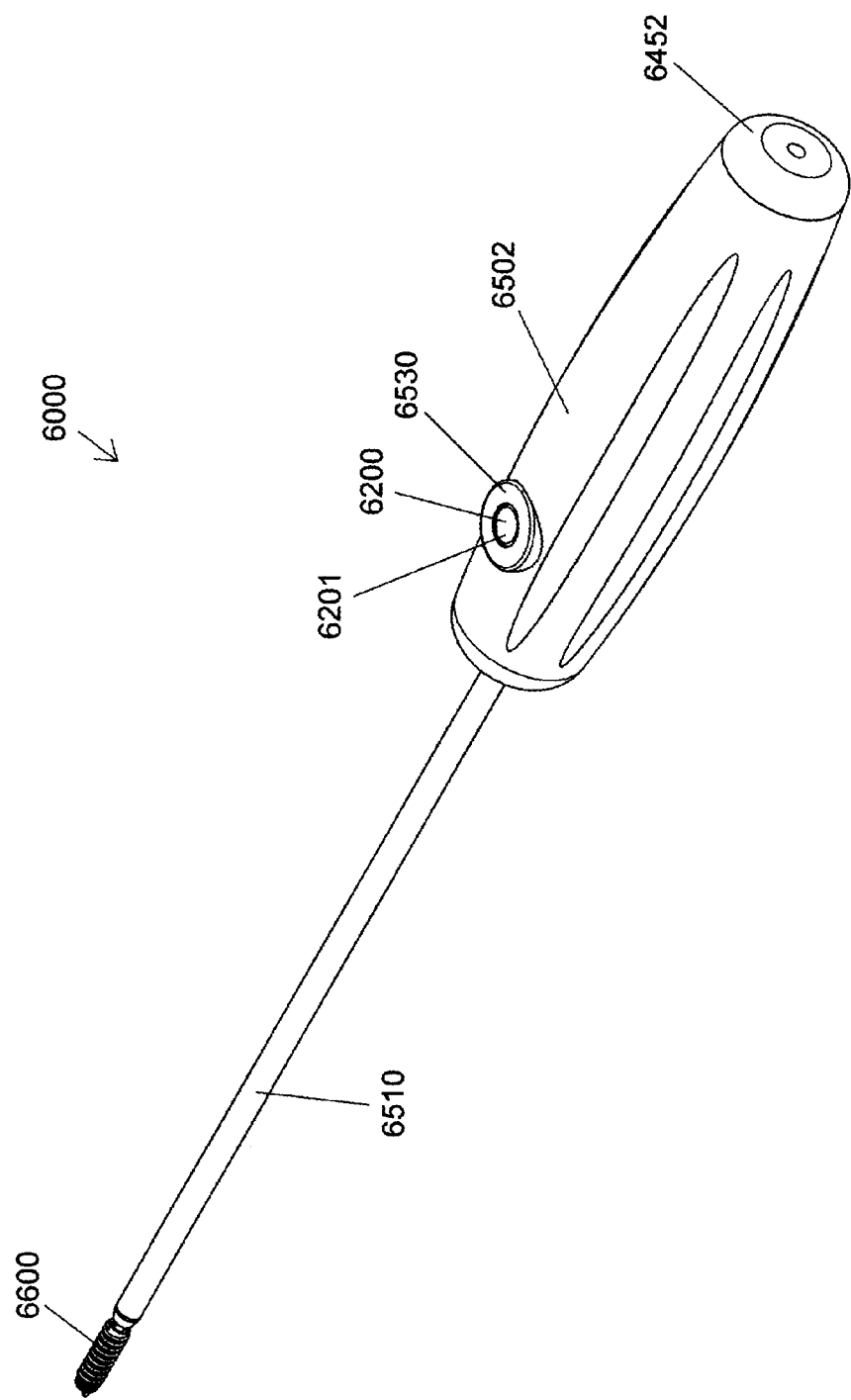
FIG. 111 is a perspective view of the implant placement system of FIG. 106, with the outer driver assembly and implant advanced on the inner tensioning assembly, as when an implant is fully placed in a socket.
Figure 112:
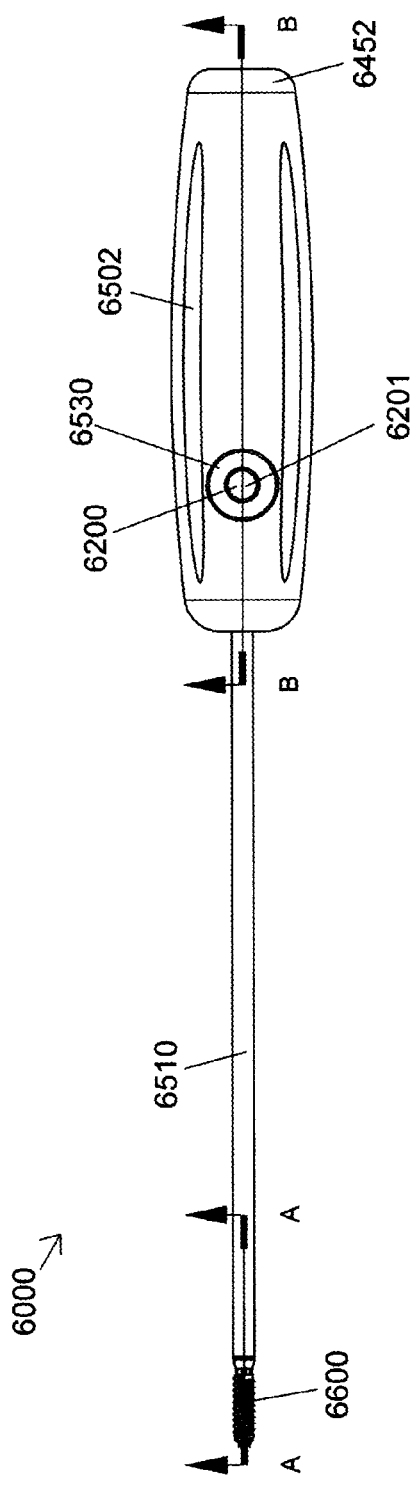
Figure 113:
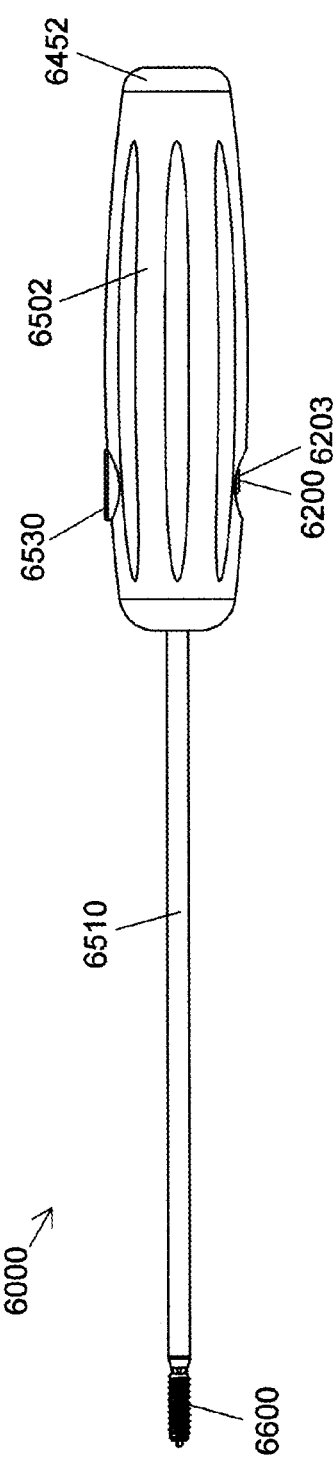
Figure 114:
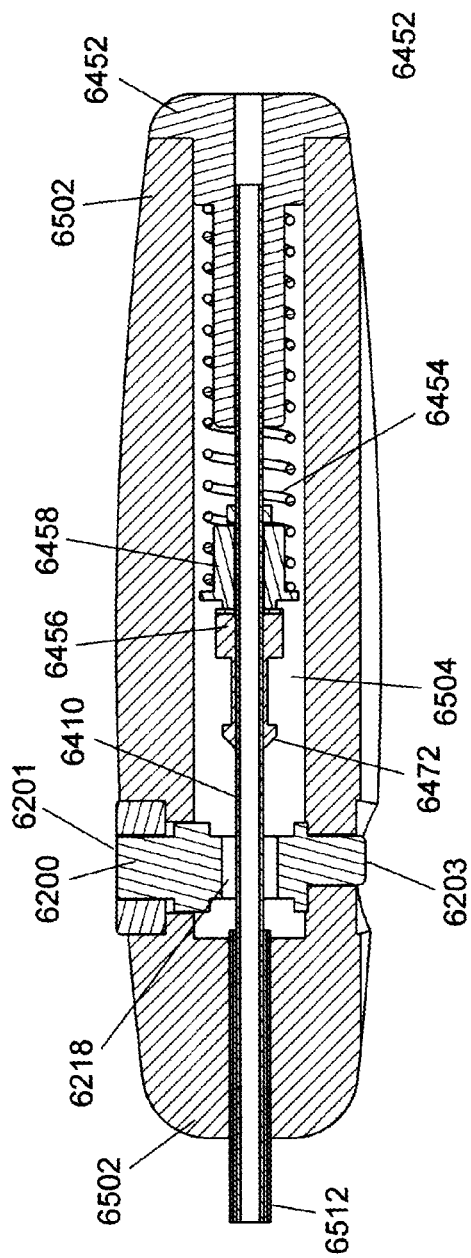
Figure 115:
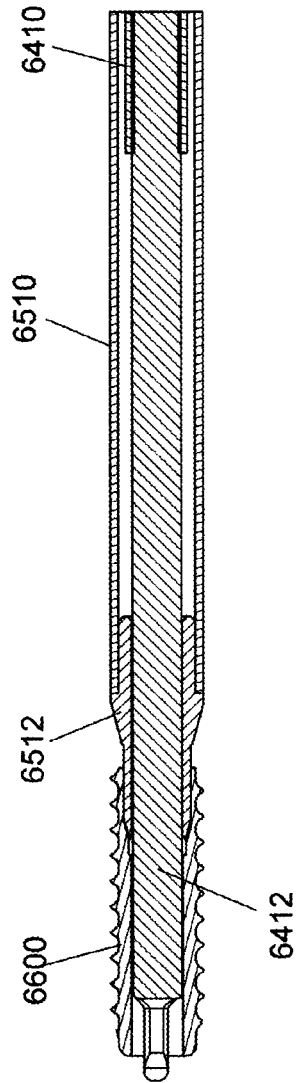

FIG. 105 shows an exploded assembly of the elements of an alternate embodiment implant placement system of the present invention. Implant placement system 6000 is identical in all aspects of form and function to implant placement system 5000 except as specifically described hereafter. For example, cannulated distal tensioning element 5412 of system 5000 is replaced by distal tensioning element 6412 which is alike to distal element 2412 (FIGS. 36 through 38) of implant placement system 2000. Spring 5230 (FIG. 94) is eliminated such that slide control 6200 may be positioned and remain in a first position in which axial motion of outer driver assembly 6500 is prevented (FIGS. 106A through 110), or may be placed and remain in a second position in which the outer driver assembly 6500 may be advanced distally against force supplied by spring 6454 (FIGS. 111 through 115). Hub 5402 of inner tensioning assembly 5400 is eliminated, the rotation of inner assembly 6400 being controlled not by the surgeon's hand on a proximal hub, but rather through interaction between the distal end of distal tensioning element 6412 and the cortical bone at the bottom of the prepared socket. Maintaining the position of the distal end of distal tensioning element 6412 at the bottom of the prepared socket is not accomplished through distal force applied to a hub like hub 2402 of the inner tensioning assembly 2400 as when using implant placement system 2000, but rather through distal force applied to handle 6502 of outer driver assembly 6500 and an elastic element acting between inner tensioning assembly 6400 and outer driver assembly 6500.

FIGS. 106A through 110 depict slide control 6200 in a first position with its topmost surface 6201 protruding above the top surface of retainer 6530. In this configuration, distal axial movement of outer tensioning assembly 6500 is prevented by interaction between slide control 6200 and element 6456 of inner tensioning assembly 6400 in the manner previously herein described with reference to implant placement system 5000. As with implant placement system 2000 (FIGS. 33 to 42), distal tensioning element 6412 has formed thereon distally extending portions 6444 separated by a gap 6446, distally extending portions 6444 having sharpened distal ends 6448, the distal end of distal tensioning element 6412 having the form of a fork. Sharpened distally extending portions 6444 are configured so as to be able to pierce tissue or cortical bone, and gap 6446 is configured so that sutures placed therein may be made to slide smoothly for the purpose of tensioning a graft.

With slide control in its second position as depicted in FIGS. 111 through 115, outer driver assembly 6500 of implant placement system 6000 may be moved distally so as to bring implant 6600 mounted thereto to a prepared socket after the position of a graft is established, and subsequently threaded into the socket. Top surface 6201 of slide control 6200 is coplanar with the upper surface of retainer 6530 while bottom surface 6203 of slide control 6500 protrudes beyond the adjacent surface portion of handle 6502 of outer driver assembly 6500.

To summarize, with slide control 6200 in its first position, axial movement of driver assembly 6500 is prevented. With slide control 6200 in its second position driver assembly 6500 rotates freely and may be moved distally relative to inner tensioning assembly 6400, the axial motion being resisted by spring 6454. In contrast to earlier described embodiments, slide control 6200 is not returned to its first position by a spring, but rather will remain in its second position until returned to its first position by the surgeon.

Figure 46:
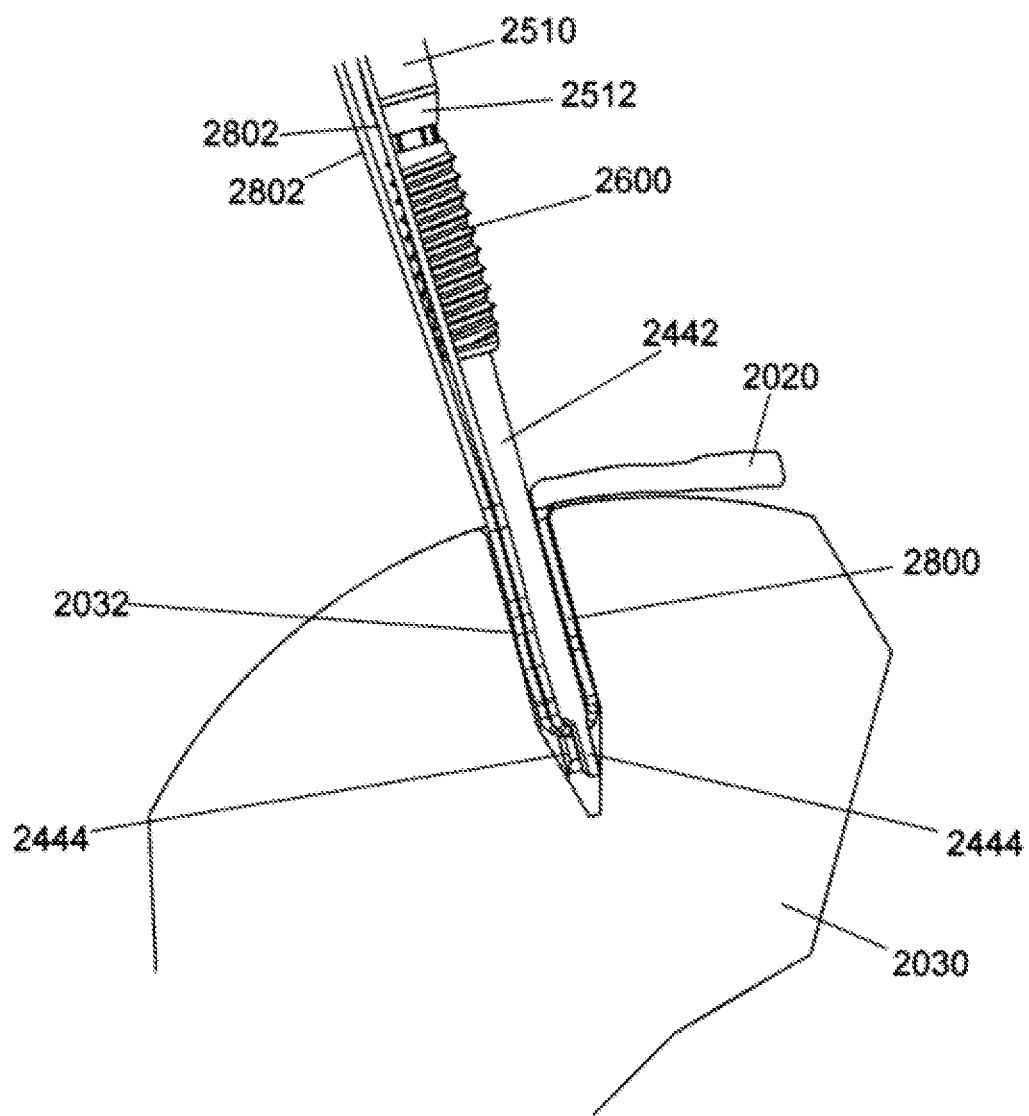
FIG. 46 is an expanded view of the distal portion of the objects of FIG. 45 that depicts the placement site.
Figure 48:
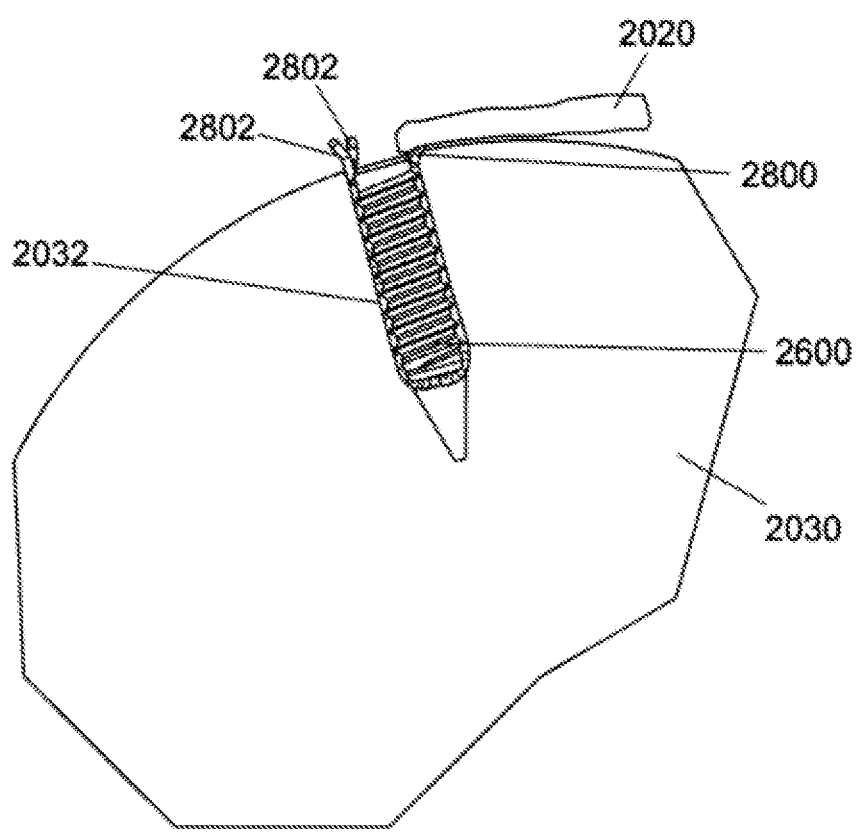
FIG. 48 is an expanded view of the site at completion of the anchor placement and removal of the system with the sutures trimmed.

The method for placing an implant in accordance with the principles of the present invention is the same as the method when using implant placement system 2000 and depicted in FIGS. 44 and 46 through 48 except as subsequently herein described. To that end, in figures referenced in the following description, depicted elements of implant system 2000 designated as "2XXX" may be replaced by their corresponding elements of implant system 6000 designated as "6XXX". Slide control 6200 of implant placement system 6000 is initially in its first position and the condition of system 6000 is as depicted in FIGS. 106A through 110. Sutures 2802 are captured in gap 6446 between distally extending portions 6444 at the distal end of distal tensioning element 6412 (see FIG. 106B) and inserted with distal tensioning element 6412 into socket 2032 as depicted in FIG. 44. Thereafter, as shown in FIG. 46, tension is applied to sutures 2802 to bring graft 2000 to the present position. The surgeon maintains this tension so as to maintain the graft position. The surgeon then moves slide control 6200 to its second position and advances outer driver assembly 6500 with implant 6600 mounted thereto distally to bring implant 6600 to socket 2032, and then threads implant 6600 into socket 2032 as shown in FIG. 47. Distal force applied to implant placement system 6000 via handle 6502 of outer driver assembly 6500 causes sufficient interference between distal end features of distal tensioning element 6412 to prevent rotation of inner tensioning assembly 6400 during subsequent threading of anchor 6600 into socket 2032. Compression of spring 6454 of inner tensioning assembly 6400 applies sufficient distal force to ensure that contact is maintained between the distal end of distal tensioning element 6412 and the cortical bone at the bottom of socket 2032. With implant 6600 threaded into position as depicted in FIG. 47, the condition of implant system 6000 is as depicted in FIGS. 111 through 115. FIG. 48 depicts the site at the completion of implant placement.

With slide control 6200 in its first position, axial movement of driver assembly 6500 of implant placement system 6000 is prevented. With slide control 6200 in its second position driver assembly 6500 rotates freely and may be moved distally relative to inner tensioning assembly 6400, the axial motion being resisted by spring 6454. As noted above, contra to earlier embodiments, slide control 6200 is not returned to its first position by a spring, but rather may remain in its second position thereby giving the surgeon the option of inserting distal tensioning element 6412 into a prepared socket and positioning the graft through the adjustment of suture tension while relying solely on the force supplied by spring 6454. The resisting force supplied to outer driver assembly 6500 by spring 6454 is sufficient to allow tensioning of sutures as previously herein described.

Implant placement system 6000 is depicted with inner assembly 6400 having distal tensioning element 6412 with its distally extending portion 6444. Inner assembly 6400 may be replaced by inner assembly 5400 with its cannulated distal tensioning element 5412 and hub 5402 without departing from the principles of the present invention.

In previously described embodiments of the present invention, the anchors placed were threaded and placed by torque applied by the driver. In other embodiments, the implants placed are interference plug-type anchors (often referred to as "push-in" implants) that are not threaded, but rather are configured for placement in a prepared socket by axial force supplied by the driver. Such implants are well known in the art and have a plurality of axially spaced conical portions formed on their cylindrical outer surface so as to allow ease of placement in the socket, while providing substantial resistance to axial removal.

An alternate embodiment of the present invention suitable for use with such "push-in" implants and incorporating a simplified construction is depicted in FIGS. 116 through 126. Implant placement system 7000 is identical in form and function to implant placement system 6000 except as specifically described hereafter. For example, control slide 6200 of implant placement system 6000 is eliminated so that outer driver assembly 7500 of placement system 7000 may be advanced distally in the same manner as outer driver assembly 6500 of implant placement system 6000 when control slide 6200 is in its second position. Implant 7600 is a push-in (interference plug) type anchor which does not have a helical thread formed on its outer surface, but rather a plurality of tapered portions (best seen in FIG. 121). Implant 7600 has a planar proximal-most surface. Distal element 7512 of outer driver assembly 6500 has a planer distal-most surface configured for transmitting axial force to implant 7600 during the placement of implant 7600. Push-in type implants and their use with embodiments of the present invention are described in U.S. Pat. No. 9,770,240 referenced and incorporated above. As noted elsewhere herein, push-in implants of the present invention may be formed of high strength ceramic materials.

Figure 116:
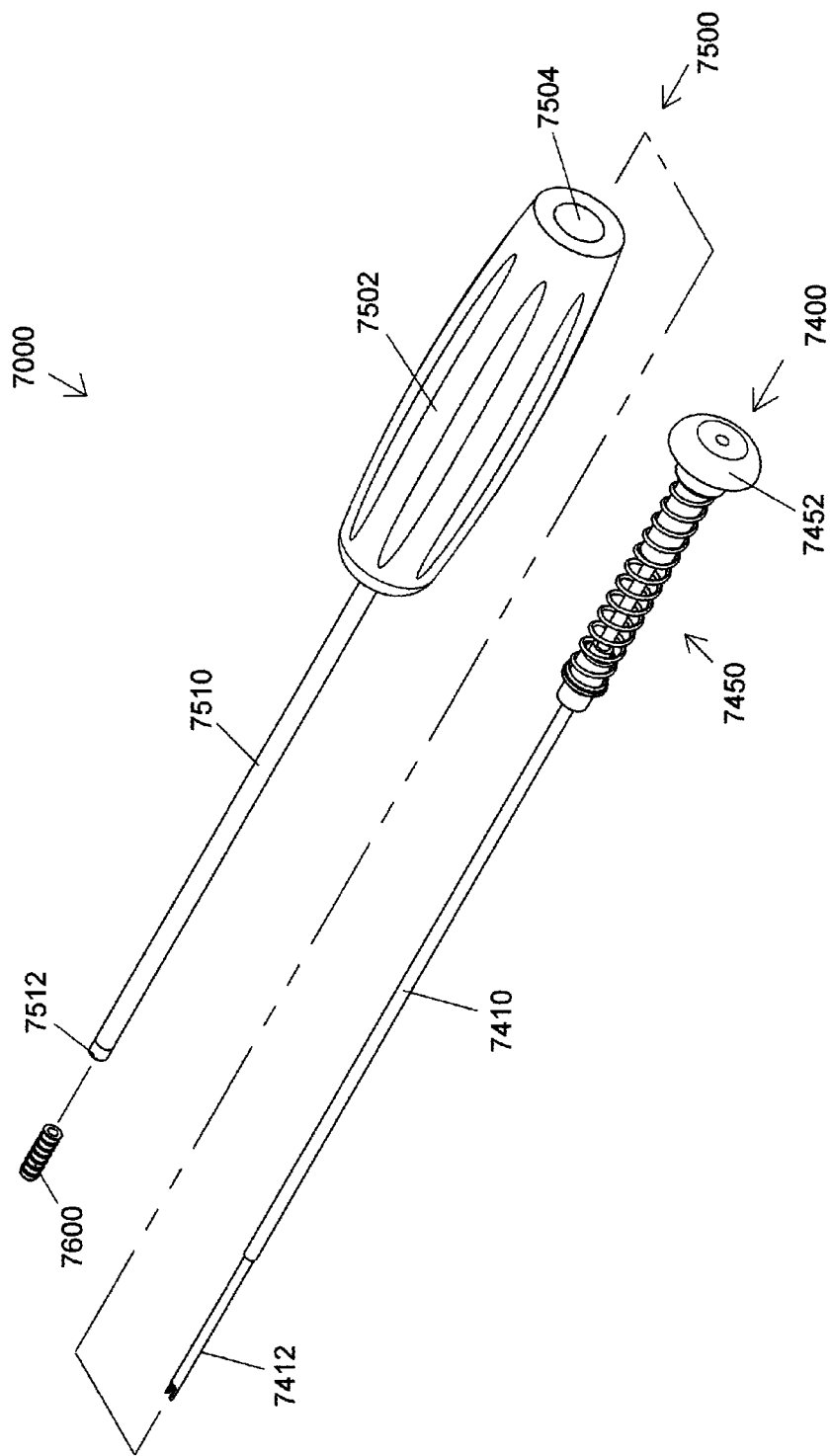
Figure 117:
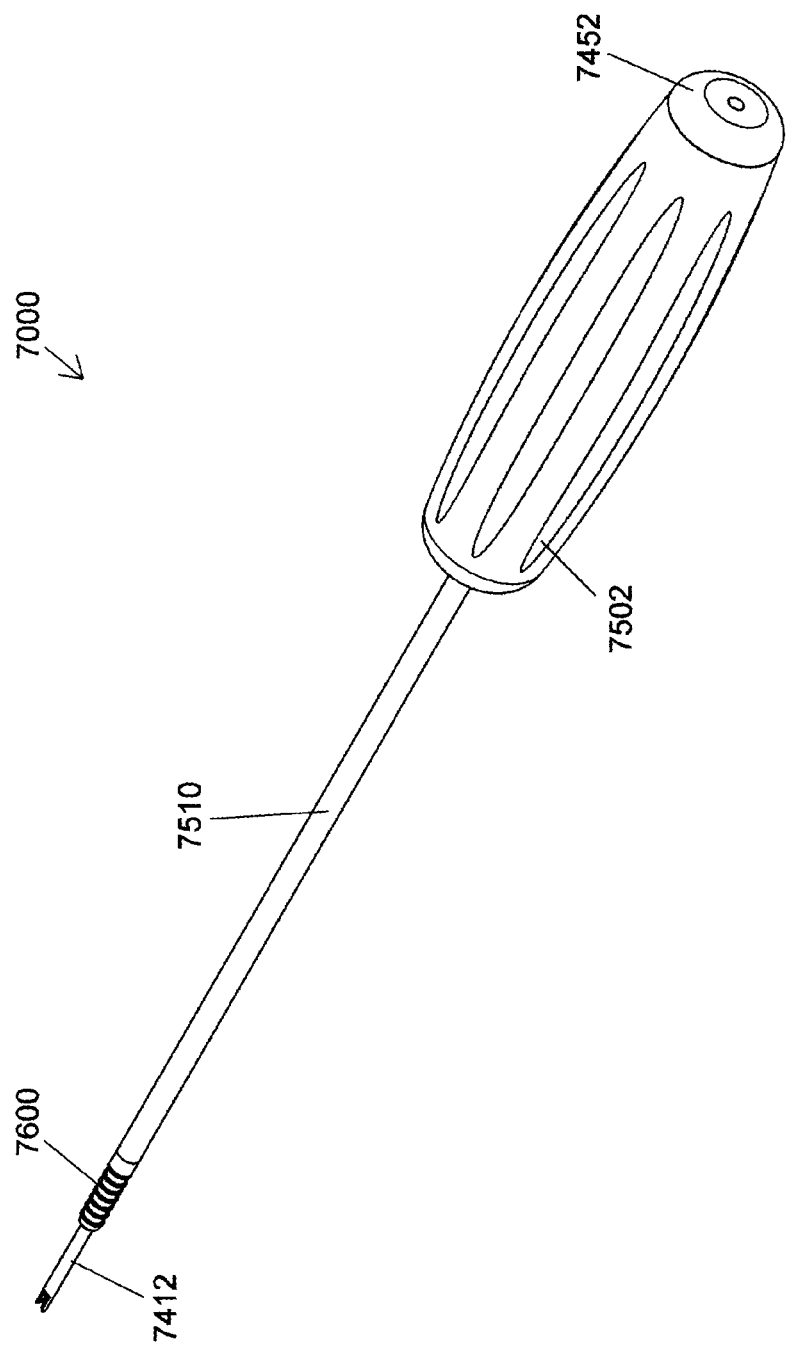
Figure 118:
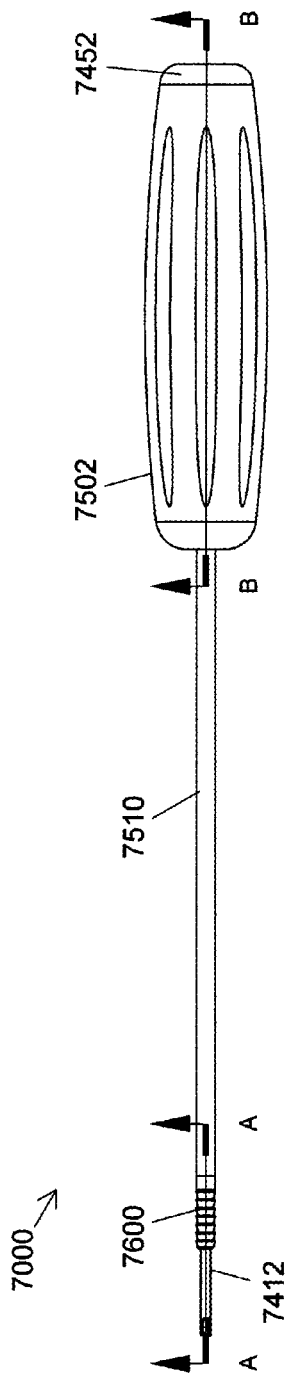
Figure 119:
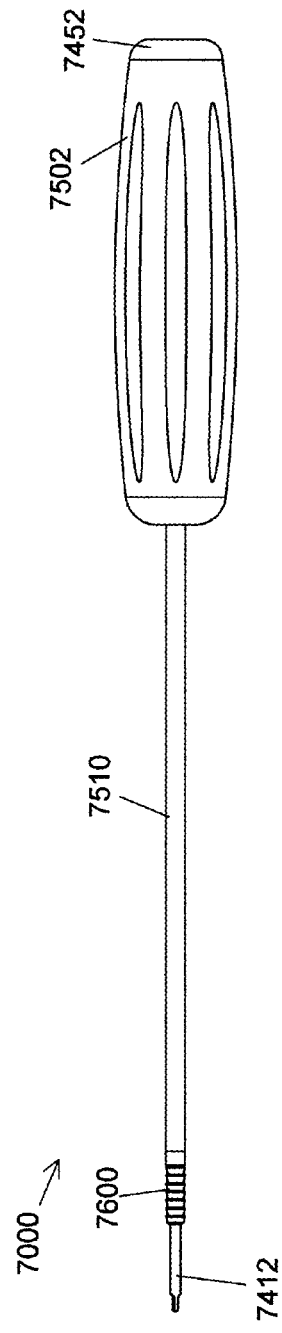
Figure 120:
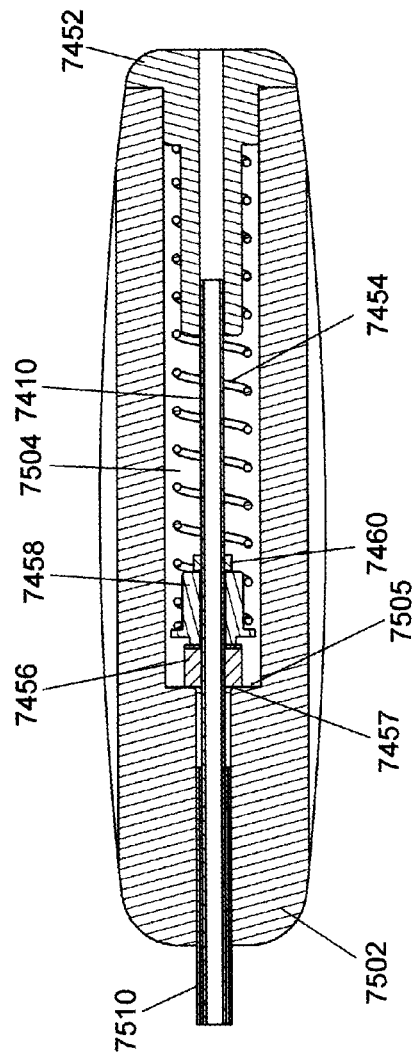
Figure 121:
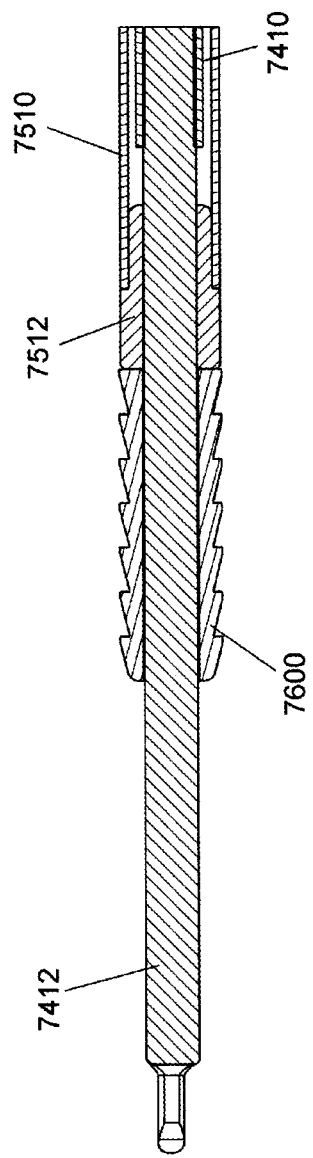

FIG. 116 is a perspective view of an exploded assembly of the elements of implant placement system 7000. Outer driver assembly 7500 is of a simple form with no external control means. FIGS. 117 to 121 depict implant placement system 7000 with outer driver assembly 7500 in its fully proximal position, maintained therein by spring 7454 of inner tensioning assembly 7400. As seen in FIG. 120, element 7456 does not have features for cooperative engagement with a slide control, but rather has a planar distal surface 7457. Cylindrical recess 7504 of outer driver portion handle 7502 has a distal-most surface 7505 which, together with distal surface 7457 of element 7456, establishes the proximal limit of travel of outer driver assembly 7500 relative to inner tensioning assembly 7400. As with implant placement systems 5000 and 6000, the force supplied by spring 7454 is sufficient to prevent distal travel of outer driver assembly 7500 during tensioning of sutures for positioning of a graft.

FIGS. 122 through 126 depict implant placement system 7000 with outer driver assembly at the distal limit of its travel as when implant 7600 is fully placed in a prepared socket. Upon removal of implant placement system 7000 from the site at the completion of placement of implant 7600, outer driver assembly 7500 returns to its proximal-most position as depicted in FIGS. 117 to 121.

Implant placement system 7000 is used in the same manner as system 6000 previously herein described except as subsequently described. For example, the surgeon is not required to move slide control 6200 to its second position prior to advancing implant 7600 to the prepared socket. The surgeon is thus able to place implant 7600 with a first hand supplying tension to the sutures for graft positioning, and a second hand, via handle 7502 of outer tensioning assembly 7500, inserting distal tensioning element 7412 into a prepared socket, and thereafter maintaining the position of element 7412 during positioning of a graft. When the graft is properly positioned, implant 7600 is incrementally driven axially into the prepared socket by repeatedly impacting proximal end cap 7452 with a mallet. When implant 7600 is fully inserted, placement system 7000 is removed from the site and the repair is completed.

While methods of use of implant systems 5000, 6000 and 7000 have been described with reference to placing an implant so as to maintain a graft position by the trapping of sutures between the implant and at least one wall of the socket, these systems may also be used for bio-tenodesis procedures as depicted in FIGS. 49 through 52, FIGS. 53 through 57, and FIGS. 58 through 63 as well as other embodiments contemplated by the present invention.

In systems 5000, 6000 and 7000 previously herein described, resistive force from a spring prevents the tensioning assembly from moving proximally during placement of an implant in a prepared socket following tensioning of a graft. In other embodiments, the resisting force is supplied not by a spring, but rather by friction supplied by elements within the implant system. This frictional resistance may be supplied by a single element for which the only function is supplying a resisting frictional force, or by existing elements within the system assembly, or by a combination of the two.

Alternate embodiment system 8000 uses frictional force to prevent proximal movement of the insertion/tensioning assembly during implant placement. System 8000 is like system 5000 in all aspects of form and function except as subsequently described. Referring to FIGS. 127 through 129, inner assembly 8400 is inner assembly 5400 (FIGS. 89 through 91) except that spring 5454, and associated elements 5458, 5460 and 5462 are eliminated. Friction producing element 8453 is mounted to the distal end of proximal element 8452. Element 8453 supplies frictional resistance to relative movement of the inner tensioning assembly 8400 relative to the outer driver assembly. The outer driver assembly is identical to outer assembly 5500 depicted in FIGS. 85 through 88.

Referring now to FIGS. 130 and 131 depicting system 8000 wherein distal element 8412 of tensioning/insertion assembly 8400 is extended distally beyond implant 8600 for tensioning sutures in preparation for implant placement, and FIGS. 132 and 133 wherein inner tensioning assembly 8400 is positioned as at the completion of implant placement. System 8000 is used in the same manner as system 5000 previously herein described. After passing sutures through a graft, the distal element 8412 is inserted into a prepared socket and the sutures tensioned for proper graft position and cleated. Thereafter, slide control 8200 is repositioned so as to allow the outer driver assembly to advance implant 8600 to the socket in preparation for placement. The friction force supplied by element 8453 acting on tubular middle portion 8410 of inner tensioning assembly 8400 is sufficient to maintain the position of the inner tensioning assembly and distal element 8412 such that the tension of the sutures is maintained and rotation of the inner tensioning assembly is prevented during anchor placement. When using implant placement system 5000, the outer driver assembly 5500 is returned to its proximal position by force supplied by spring 5454. When using implant placement system 8000 the surgeon must manually return the outer driver assembly to its proximal position by grasping distal element 8412 of inner tensioning assembly 8400 and pulling it back to its distally extended position. Thereafter another implant 8600 may be mounted to the system and placed as previously described.

Tensioning element 8453 may be formed of a metallic or polymeric material. In a preferred embodiment tensioning element 8453 is formed of a resilient polymeric material. Tensioning element 8453 may be of unitary construction, or may be an assembly. In some embodiments element 8453 is formed of an assembly of metallic elements. In other embodiments tensioning element 8453 is an assembly of rigid and resilient polymeric materials, the resilient polymeric material contacting middle portion 8410 of inner tensioning assembly 8400 so as to provide suitable frictional resistance therebetween.

While the use of tensioning element 8453 is described as applied to system 8000, which is a modification of system 5000 with its inner cannulated tensioning assembly 5400, tensioning element 8453 may be applied to systems 6000 and 7000 as well. Springs 6454 of system 6000 and 7454 of system 7000 with their associated elements may be eliminated and resistance to relative axial motion between the inner tensioning assembly and outer driver assembly supplied by a friction resistance element like element 8453 of system 8000.

Implant placement system 9000, depicted in FIGS. 134 through 139, is identical to system 6000 (FIGS. 105 through 115) in all aspects of form and function except as hereafter described. Specifically, spring 6454, and associated elements 6458, 6460 and 6462 are eliminated. Proximal element 6452 of inner assembly 6450 is modified as depicted in FIGS. 134 through 137. Lumen 9459 of proximal element 9452 has a proximal portion 9455 with a diameter larger than that of middle element 9410, and a distal portion 9457 in which the diameter is reduced such that the distal portion of lumen 9459 contacts middle element 9410 so as to create a frictional resistance to axial movement between the elements. A plurality of slots 9451 creates resilient, distally extending regions therebetween, the geometry of these regions determining the contact force exerted thereby on middle element 9410 and the resulting frictional resistance to relative movement therebetween. System 9000 is used in the same manner as system 6000 except that after placement of an implant, the surgeon the outer driver assembly is returned to its proximal position in preparation for placing another anchor by pulling distal element 9412 of inner tensioning assembly 9400 to its full distal extension. Thereafter another implant 9600 may be loaded onto the system 9000 in preparation for placement. The modifications made to system 6000 to form placement system 9000 may be advantageously made to systems 5000 and 7000 as well.

In systems 8000 and 9000, the friction-producing means is proximally located in the handle of the systems. In other embodiments, the friction-producing device may be located distally. For example, in system 10000, the distal portion of which is shown in FIGS. 140 through 142, annular ring 10011 provides frictional resistance to the advancement of implant 10600 and the associated outer driver assembly following tensioning of a suture and during implant placement. Annular ring 10011 is preferably formed from a suitable biocompatible polymeric material. Annular ring 10011 remains in the socket distal to implant 10600 at the completion of placement of implant 10600. Torque transmission from the distal end of implant 10600 to distal element 10412 of the inner tensioning assembly is minimal and insufficient to cause rotation of distal element 10412 during implant placement.

Figure 85:
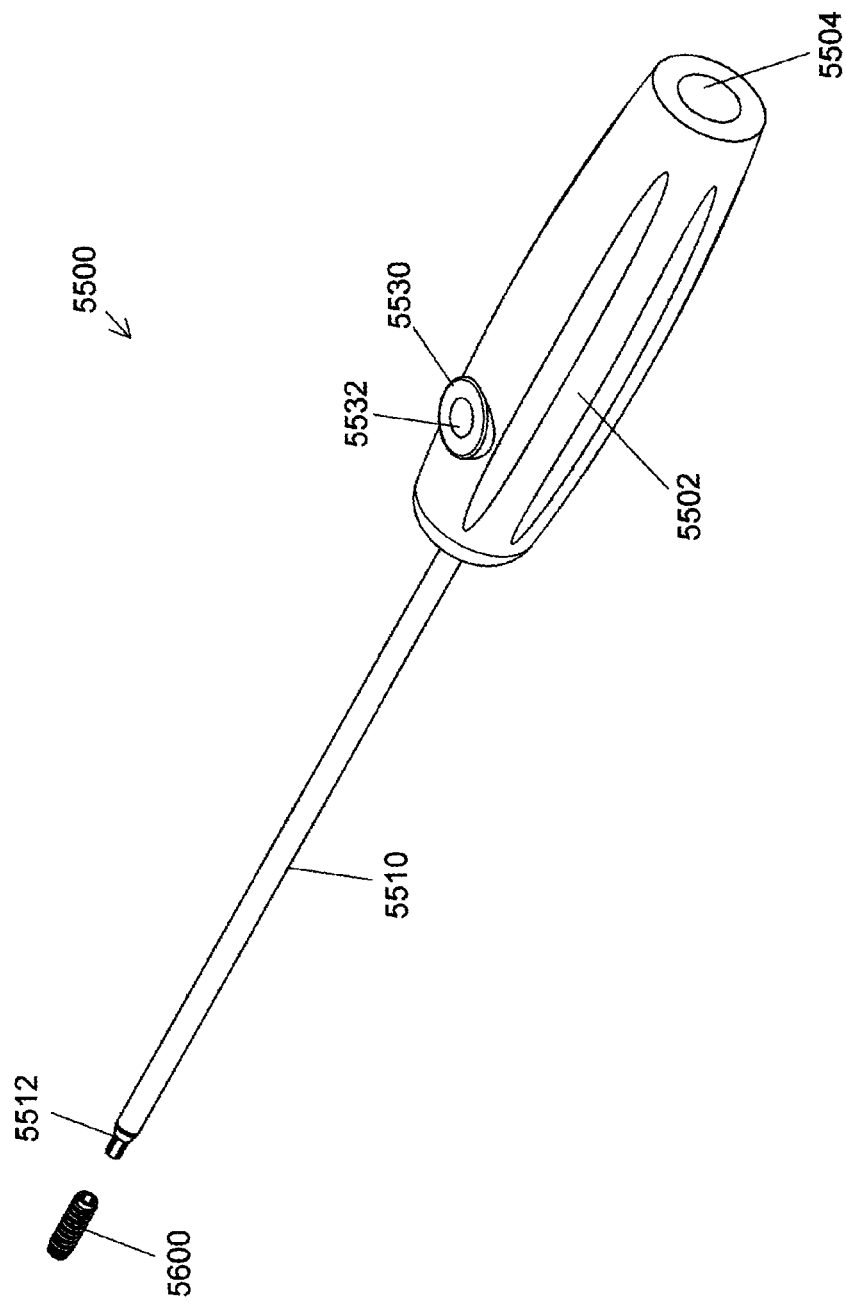
FIG. 85 is a perspective view of an outer driver assembly in an alternate embodiment of an implant placement system in accordance with the present invention.
Figure 86:
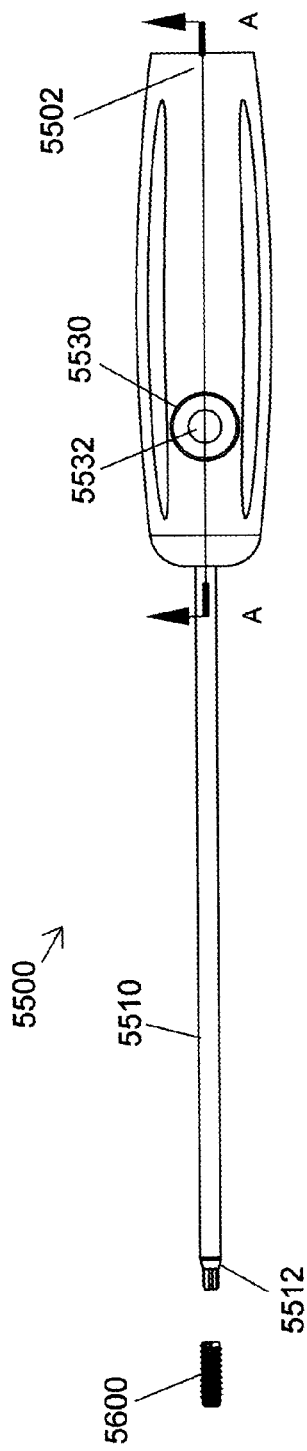
FIG. 86 is a plan view of the driver of FIG. 85.
Figure 87:
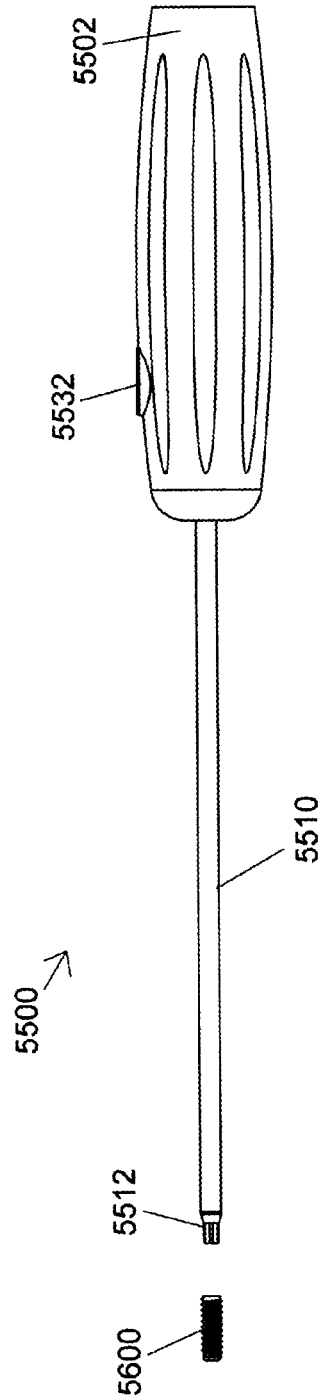
FIG. 87 is a side elevational view of the driver of FIG. 85.
Figure 88:
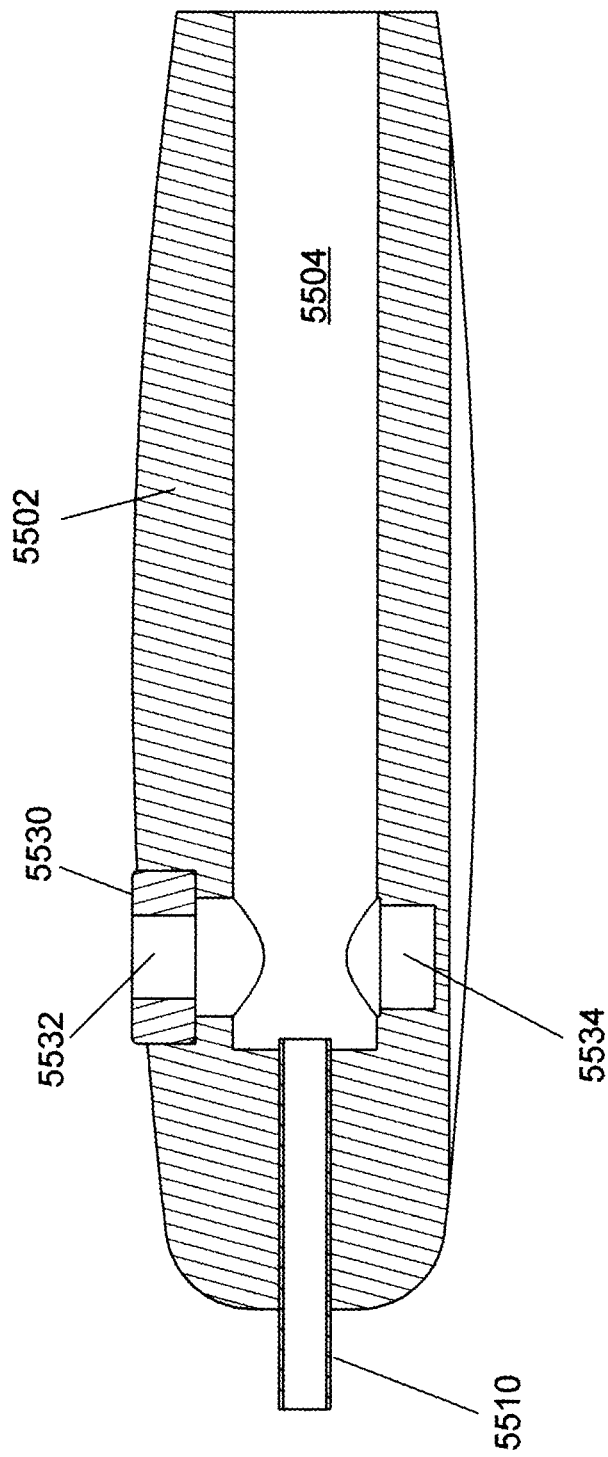
FIG. 88 is a sectional view of the objects of FIG. 86 at location A-A.
Figure 89:
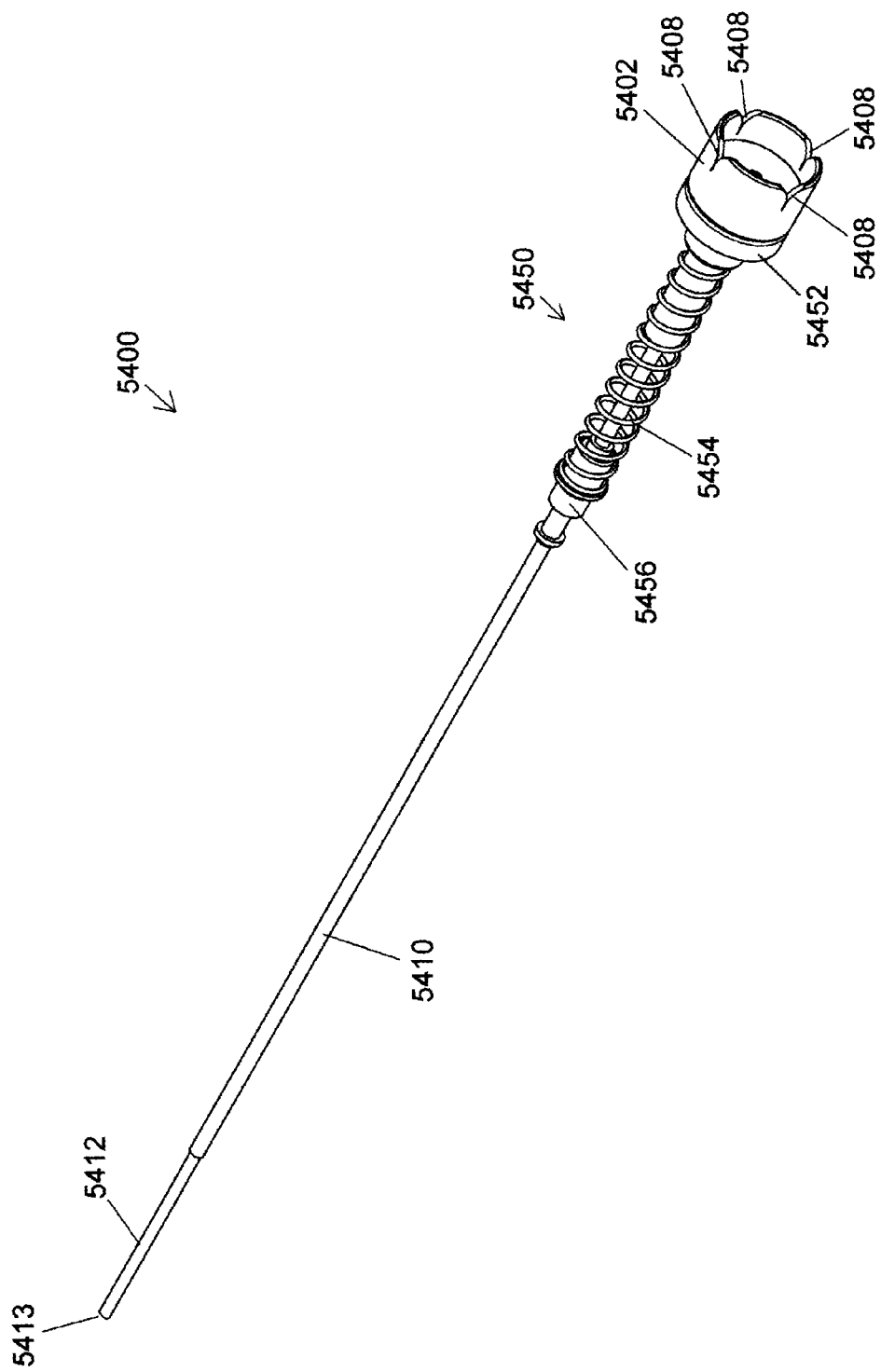
FIG. 89 is a perspective view of an inner tensioning assembly for an alternate embodiment of an implant placement system of the present invention.
Figure 90:
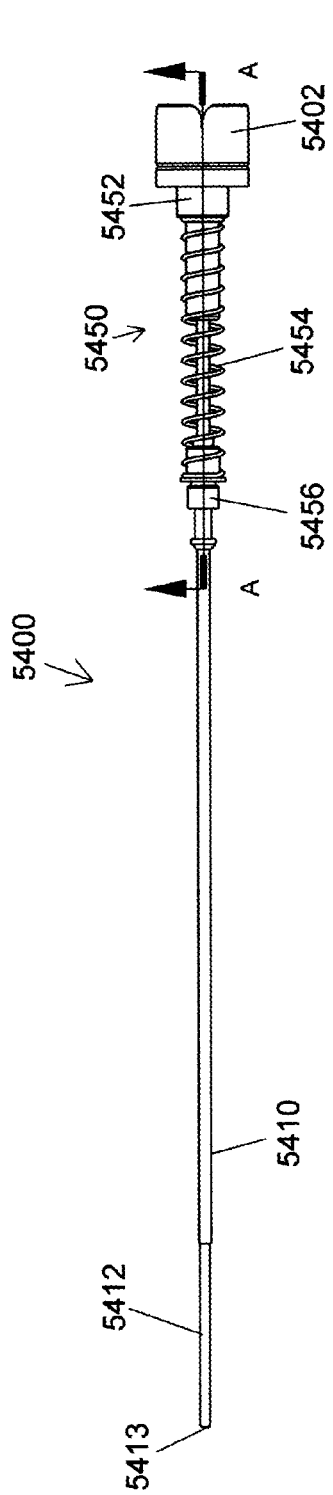
FIG. 90 is a plan view of the objects of FIG. 89.
Figure 91A:
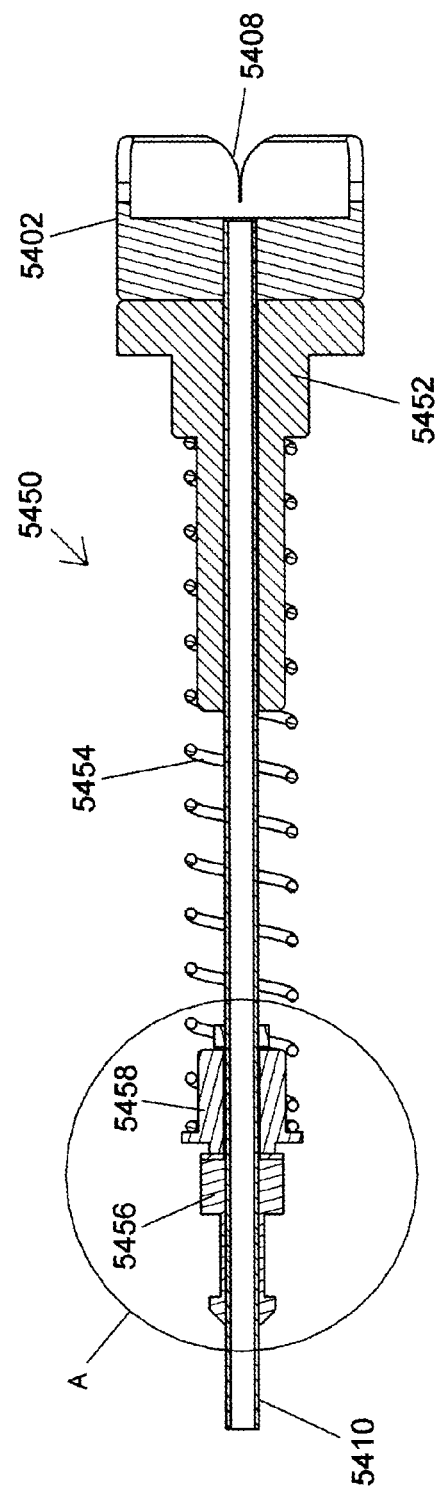
FIG. 91A is an expanded sectional view of the objects of FIG. 89 at location A-A.
Figure 91B:
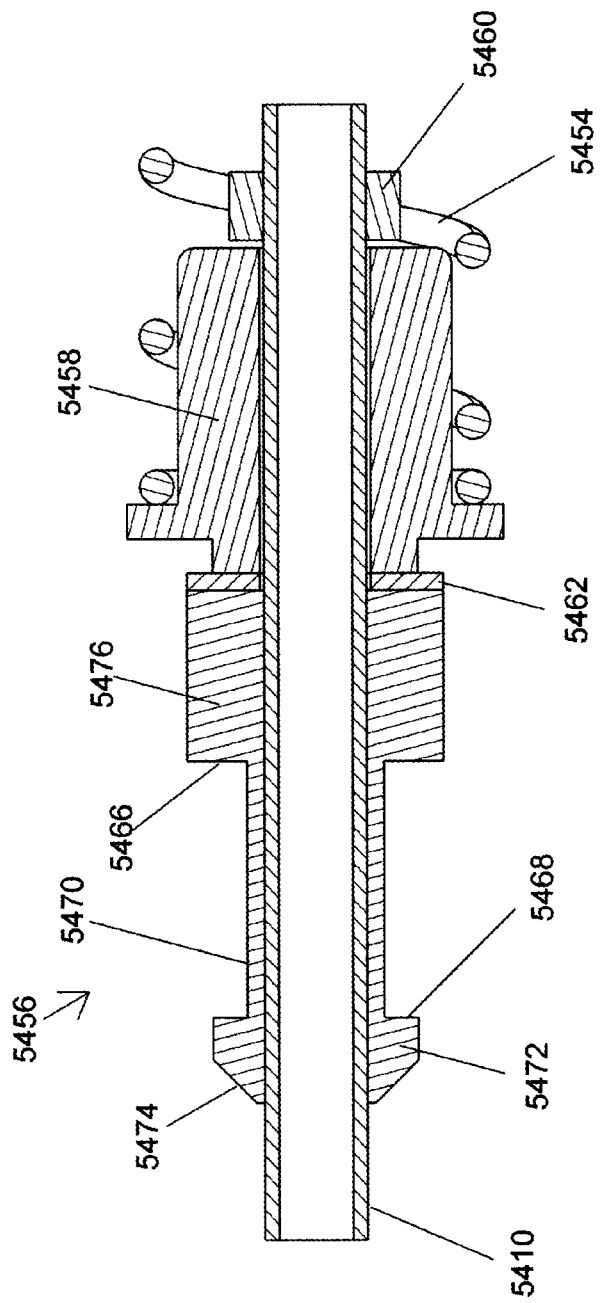
FIG. 91B is an expanded view of the objects of FIG. 91A at location A.

In other embodiments of the present invention, the frictional resistance to moving may be supplied by the distal element, for example by distal drive element 5512 of outer driver assembly 5500 of system 5000 in FIG. 85. In other embodiments, the frictional resistance force is distributed throughout the assembled components so that no single element provides the total frictional resistance.

Anchor placement system 2000, depicted in FIGS. 33 through 42, may be used as in FIGS. 43 through 52 wherein sutures are retained within channel 2446 between distally extending portions 2444 of distal element 2442 of tensioning device 2400, or as in FIGS. 53 through 63 wherein distally extending portions 2444 pierce the graft for insertion of the graft into the socket for anchor placement. In other embodiments of the present invention, the distal end of the distal element of the tensioning device is optimized for use in the manner of FIGS. 43 through 52 wherein sutures are retained at the distal end of the tensioning device.

For example, FIGS. 143 through 145 depict distal element 12442 that is alike in form and function to distal element 2442 (FIGS. 36 through 40) and all corresponding non-cannulated distal elements with distal fork portions previously herein described in all aspects except as specifically subsequently described herein. Specifically, distally extending portions 12444 has distal portions 12445 that extend medially at their distal ends so that channel 12446 formed between distally extending portions 12444 forms an eyelet having a gap 12447 in its distal end. Some current repair techniques for attaching a graft to a boney surface anchor utilize multiple strands of suture with a single implant. Accordingly, it may be desirable to affix as many as six sutures with a single implant. The length of distally extending portions 12444 may thus be extended thereby increasing the size of channel 12446 to accommodate a desired number of suture strands.

Another alternate embodiment 22000, the distal portion of which is depicted in FIGS. 146 through 148, has a resiliently deformable polymeric distal element 22443 affixed to the distal end of element 22442. Like distally extending portions 12444 of the distal portion of distal element 12442, distally extending portions 22444 of polymeric distal element 22443 are configured for the retention of sutures therebetween, the distal portions of extending portions 22444 curving inward to form a distal gap 22447 between their distal ends. Because distally extending portions 22444 are formed of a resiliently deformable polymeric material, maximum width 22445 across portions 22444 may exceed the diameters of the lumen of implant 22600, distally extending portions 22444 deforming inward to allow withdrawal of distal elements 22442 and 22443 from implant 22600 after placement, or for the reinsertion of these elements for implant removal and reinsertion. In a preferred embodiment, distal element 22443 is formed of PEEK or a similar resilient polymeric material. In other embodiments, distally extending elements 22444 are formed of a super-elastic metallic material such as nitinol.

The distally extending portions of the distal end of the distal tensioning element may be rigid, resilient, elastically or inelastically deformable, integral with the distal tensioning element, affixed to the distal end thereof or positioned within a lumen thereof, and formed of a metallic or non-metallic material. All fall within the scope of this invention.

FIGS. 149 and 150 depict a depth-limiting element 32001 formed of a suitable metallic or polymeric material for use with implant placement system 2000 (FIGS. 33 through 42) when used for attachment of a soft tissue graft to bone as depicted in FIGS. 53 through 57 and FIGS. 58 through 63.

Referring now to FIGS. 53 through 57, wherein graft 3020 is impaled on distally extending portions 3444 of distal element 3442 and thereafter inserted into socket 3032 prior to the placement of implant 3600, the force required to insert graft 3020 may be sufficient to cause failure of graft 3020 at the impalement site. Specifically, the distal end of distal element 3442 may excessively penetrate graft 3020 so as to tear graft 3020 such that graft 3020 slides proximally up distal element 3442 rather than being inserted into socket 3032. The depth of penetration of distal element 3442 into graft 3020 may be limited by depth limiting element 32001.

Referring to FIGS. 149 and 150, element 32001 has formed therein slots 32003 configured for removable mounting to distally extending portions 3444 of distal element 3442. Referring now to FIGS. 151 through 154, the distal portion of alternate embodiment system 32000 is identical in all aspects to system 3000 depicted in use in FIGS. 53 through 57 and 58 through 63 and in all aspects of form and function except that depth limiting element 32001 is removably affixed to distally extending portions 32444 of distal element 32442. As described and depicted in inventors' own U.S. Pat. No. 9,566,060 (formerly U.S. application Ser. No. 15/012,060 to which the instant applications claims priority as a continuation-in-part), in an alternate embodiment placement system 42000, the distal portion of which is depicted in FIGS. 155 and 156, distally extending portions 32444 of placement system 32000 may be replaced by a single distally extending portion 42444 configured for piercing of a soft tissue graft. Depth-limiting element 42001 is configured for removable mounting to the distal end of elongate distal element 42442.

Placement system 42000 may be used in the same manner for attaching a graft to a boney surface as system 3000 depicted in FIGS. 53 through 57. The method for fixation of graft 3020 to boney surface 3030 is alike in all aspects of form and function except as specifically herein described and depicted in FIGS. 157 through 161. Socket 3032 is formed in boney surface 3030 in a predetermined location. Depth-limiting element 42001 is removably affixed to the distal end of elongate distal portion 42442 of placement system 42000. As depicted in FIGS. 157 through 161, whip stitches 3021 have been placed in the distal portion of graft 3020. Whip stitches 3021 are optionally added to increase the resistance of the completed construct to failure due to tensile load and are not a required element of forming a construct in accordance with the principles of the present invention. Graft 3020 is impaled on the distally extending portion 42444 of distal element 42442 as shown in FIGS. 157 and 158, depth limiting element 42001 limiting the depth of penetration of distally extending portion 42444 into graft 3020. Thereafter, distal element 42442 is inserted into socket 3032 as shown in FIG. 159 with depth limiting element 42001 preventing additional penetration of graft 3032 due to the force applied during insertion. Anchor 42600 is placed as depicted in FIG. 160 trapping graft 3020 between anchor 42600 and the boney surface of the wall of socket 3032. Friction force between the inserted portion of graft 3020 and socket 3032 maintains the position of graft 3020 relative to socket 3032 and bone 3030. Optional whip stitches 3021 increase the resistance to movement of graft 3020 relative to socket 3032 when a tension force is applied to graft 3020. FIG. 161 depicts the site at completion of the anchor placement and removal of insertion system 42000. Depth limiting element 42001 remains in the construct adjacent to the distal end of implant 42600, between implant 42600 and graft 3020.

An alternative method for affixing a soft tissue graft to a boney surface using placement system 42000 is like the placement method depicted in FIGS. 58 through 63 in all aspects of form and function except as specifically described below and depicted in FIGS. 162 through 167. Depth-limiting element 42001 is removably affixed to the distal end of elongate distal portion 42442 of placement system 42000. As depicted in FIGS. 162 through 167, optional whip stitches 3021 have been formed in the distal portion of graft 3020. A preferred method of affixing graft 3020 to boney surface 3030 thereafter has the following steps. Socket 3032 is formed in boney surface 3030 at a predetermined location. Graft 3020 is impaled on the sharpened distally extending portion 42444 of distal element 42442 as shown in FIGS. 162 and 163, the sharpened distal end of distally extending portion 42444 penetrating the graft with the depth of penetration being limited by depth limiting element 42001. The site for penetration is selected such that when the distal portion of graft 3020 is inserted to the bottom of socket 3032 the distal end of graft 3020 protrudes above the rim of socket 3032. As seen in FIG. 164, graft 3020 is positioned above socket 3032 and inserted as shown in FIG. 165. Depth limiting element 42001 prevents penetration of graft 3020 by distal element 42442 during insertion due to the insertion force applied. Thereafter, anchor 42600 placed as shown in FIG. 166. FIG. 167 shows the completed repair. Graft 3020 is trapped between the exterior surface of anchor 3600 and first and second laterally opposed portions of the wall of socket 3032 and retained in position by friction therefrom. Depth-limiting element 42001 remains in the construct adjacent to the distal end of implant 42600, between implant 42600 and graft 3020.

FIGS. 168 and 169 depict the distal portion of an embodiment wherein distally extending portions 52444 of distal tensioning element 52442 are formed of the distal portion of elongate metallic element 52447 depicted in FIGS. 170 and 171. Elongate element 52447 has a distal end forming distally extending portions 52444, and parallel proximally extending elongate portions 52445 that are joined at proximal end 52449. When assembled for use as depicted in FIGS. 168 and 169, elongate element 52447 is positioned within the lumen of distal tensioning element 52442 with distally extending portions 52444 aligned with slots 52441 in the distal end of tensioning element 52442. The axial position of elongate element 52447 within distal tensioning element 52442 may be maintained by an elongate element such as a wire or suture with its distal end attached to proximal end 52449 of elongate element 52447, and its proximal end cleated to the hub of the tensioning element. Alternatively, the proximal end of elongate element 52447 may be attached to the proximal end of distal tensioning element 52442 by welding, brazing, adhesive or mechanical means. Distally extending portions 52444 elastically and/or inelastically deform inwardly to allow distal tensioning element 52442 to be withdrawn through the lumen of implant 52600.

INDUSTRIAL APPLICABILITY

As noted previously, there is a need in the art for simplified placement systems and methods for tissue graft anchors by which the surgeon may introduce one or more sutures into a prepared socket in the boney tissue, apply tension to the sutures to advance a soft tissue graft to a desired location, and then advance an anchor into the bone while maintaining suture tension. The present invention addresses this need by providing a system and method for the placement of an implant, especially a suture anchor, threaded, knotless or otherwise, that allows the surgeon to establish the graft position and, while maintaining that position, secure the anchor without changing the suture tension or causing a shift in the graft position and furthermore, when the anchor is threaded, without spinning of the suture. The present invention also provides off-axis socket drills and implant driving devices that enable implantation in remote and difficult to access boney surfaces using minimally invasive procedures. The present invention further provides embodiments in which the relative axial movement between the inner tensioning device and outer driver device is physically constrained, for example by means of springs, friction resisting elements, and the like, so as to allow for one-handed operation. Although described in detail with respect to ligament repairs, such as repair of a torn rotator cuff, it will be readily apparent to the skilled artisan that the utility of the present invention extends to other tissues and injuries.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. An implant placement system for affixing a soft tissue graft to a prepared socket in a boney surface via a cannulated anchoring implant, said system comprising:
   a. a cannulated driver device comprising a proximal handle portion, an elongate tubular distal portion that defines a longitudinal axis of the system and includes an open distal end configured to receive said implant, and at least one driver lumen extending from said proximal handle portion to said open distal end;
   b. an elongate insertion device that includes a rigid distal portion configured to receive first ends of one or more elongate sutures; and
   c. an axial control assembly having a first constrained configuration and a second free configuration;
   wherein:
      i. said insertion device is slidably received within said at least one lumen of said driver device;
      ii. when said axial control assembly is in said first constrained configuration, the distal portion of said insertion device extends distally past a distal end of said implant when coupled to said driver device so as to enable said insertion device distal portion to receive said suture first ends and relative axial movement between said driver device and said insertion device is precluded; and
      iii. when said axial control assembly is in said second free configuration, the driver device and implant move axially in a distal direction along the length of said rigid distal portion of said insertion device to thereby drive said implant into said socket while the insertion device is maintained in a fixed position.

2. The implant placement system of claim 1, wherein said axial control assembly includes a longitudinal spring contained within a proximal hub portion of said elongate insertion device.

3. The implant placement system of claim 2, wherein said longitudinal spring is held in a compressed configuration by one or more slidable control elements.

4. The implant placement system of claim 3, wherein said slidable control element extends through a lateral wall of said proximal hub portion and is transversely oriented to the longitudinal axis.

5. The implant placement system of claim 1, wherein said axial control assembly includes one or more friction producing elements that, in the first constrained configuration, apply a resistive frictional force to an exterior surface of said elongate insertion device so as to prevent proximal movement of said insertion device relative to said driver device.

6. The implant placement system of claim 5, wherein said resistive frictional force is applied to a proximal portion of said elongate insertion device.

7. The implant placement system of claim 6, wherein said resistive frictional force is applied to the proximal portion of said elongate insertion device in a circumferential fashion.

8. The implant placement system of claim 1, wherein said axial control assembly includes one or more friction producing elements that, in the first constrained configuration, apply a resistive frictional force to an exterior surface of said driver device sufficient to resist the distal advancement of both said driver device and said implant.

9. The implant placement system of claim 1, wherein said elongate insertion device include a hub portion at its proximal end.

10. The implant placement system of claim 1, wherein said implant comprises an interference plug-type anchor.

11. The implant placement system of claim 1, wherein said implant comprises a threaded anchor.

12. The implant placement system of claim 1, wherein said implant comprises a cannulated knotless suture anchor fabricated from a high strength ceramic material selected from the group consisting of alumina and zirconia.

13. The implant placement system of claim 1, wherein the distal end of said driver device and a proximal end of said implant are provided with mating features that enable secure attachment of said implant to said driver device.

14. The implant placement system of claim 1, wherein said rigid distal portion of said insertion device has at its distal end a sharpened fork portion characterized by two or more axially extending tines spaced apart to define one or more channels therebetween in which said one or more first ends of said one or more elongate sutures may be slidably received.

15. The implant placement system of claim 1, wherein said elongate insertion device further comprises an open proximal end, an open distal end, and at least one insertion lumen extending from said open proximal end to said open distal end.

16. The implant placement system of claim 15, wherein said system further comprises an elongate element formed from a suitably elastic metallic or polymeric material and having a first configuration characterized by first and second free proximal ends and a distal end in the form of a suture capturing loop configured to receive the first ends of one or more elongate sutures;
   wherein:
      i. said insertion device is slidably received within said at least one driver lumen such that the rigid distal portion extends out of the open distal end of said driver device and distally past the distal end of said implant when coupled to said driver device; and
      ii. said elongate element in said first configuration is slidably received within said at least one insertion lumen such that the suture capturing loop extends out of and distally past the open distal end of said insertion device so as to enable said suture capturing loop to receive said one or more suture first ends.

17. A method for affixing a soft tissue graft to a target boney surface, the method comprising the steps of:
   a. providing the implant placement system of claim 1 with a proximal end of said driver device handle portion engaged to said insertion device and the axial control assembly in said first constrained configuration, whereby relative axial movement between said driver device and said insertion device is precluded;

b. positioning an anchoring implant to the distal end of said driver device;

c. providing one or more elongate sutures, each of which has first and second ends, wherein said one or more second ends are attached to said soft tissue graft;

d. receiving each of said first ends in the distal end of said insertion device;

e. inserting the distal end of the insertion device into a suitably configured socket disposed in said target boney surface;

f. applying tension to the suture to draw the soft tissue graft to a desired position;

g. shifting said axial control assembly to said second free configuration; and h. distally advancing said driver device so as to drive the implant in the socket, whereby said implant serves to anchor said soft tissue graft to said target boney surface.

18. The method of claim 17, further comprising repeating steps (b) through (h) as required.

19. The method of claim 17, wherein said anchoring implant comprises an interference plug-type anchor, further wherein the distal end of said driver device and a proximal end of said interference plug-type anchor are provided with mating features that enable the transfer of axial force from the driver device to the anchoring implant.

20. The method of claim 17, wherein said anchoring implant comprises a threaded anchor, further wherein the distal end of said driver device includes torque transmitting features that, together with complementary torque receiving features formed in a proximal portion of the anchor, allow the transmission of torque to said anchoring implant.

* * * * *